United States Patent
Collins et al.

(10) Patent No.: US 9,388,425 B2
(45) Date of Patent: Jul. 12, 2016

(54) TUNABLE GENETIC SWITCH FOR REGULATING GENE EXPRESSION

(75) Inventors: James J Collins, Newton Center, MA (US); Tara L Deans, Clarksville, MD (US)

(73) Assignee: TRUSTEES OF BOSTON UNIVERSITY, Boston, MA (US)

(*) Notice: Subject to any disclaimer, the term of this patent is extended or adjusted under 35 U.S.C. 154(b) by 1402 days.

(21) Appl. No.: 12/446,300

(22) PCT Filed: Oct. 19, 2007

(86) PCT No.: PCT/US2007/081965
§ 371 (c)(1),
(2), (4) Date: Feb. 4, 2010

(87) PCT Pub. No.: WO2008/051854
PCT Pub. Date: May 2, 2008

(65) Prior Publication Data
US 2010/0175141 A1    Jul. 8, 2010

Related U.S. Application Data

(60) Provisional application No. 60/853,357, filed on Oct. 20, 2006.

(51) Int. Cl.
*C12N 15/11* (2006.01)
*C12N 15/85* (2006.01)
*C12N 15/63* (2006.01)

(52) U.S. Cl.
CPC .............. *C12N 15/85* (2013.01); *C12N 15/111* (2013.01); *C12N 15/63* (2013.01); *C12N 2310/14* (2013.01); *C12N 2320/30* (2013.01); *C12N 2800/30* (2013.01); *C12N 2830/005* (2013.01); *C12N 2830/006* (2013.01); *C12N 2830/50* (2013.01); *C12N 2840/102* (2013.01)

(58) Field of Classification Search
None
See application file for complete search history.

(56) References Cited

U.S. PATENT DOCUMENTS

| | | |
|---|---|---|
| 6,716,622 B2 | 4/2004 | Curiel |
| 7,183,262 B2 | 2/2007 | Li |
| 2001/0049828 A1 | 12/2001 | Orosz |
| 2002/0022018 A1 | 2/2002 | Curiel et al. |
| 2002/0065243 A1 | 5/2002 | Fung |
| 2003/0045495 A1 | 3/2003 | Li et al. |

FOREIGN PATENT DOCUMENTS

| | | | | |
|---|---|---|---|---|
| WO | WO2006/002538 | * | 1/2006 | ......... A61K 31/7105 |

OTHER PUBLICATIONS

Pluta et al in "Lentiviral vectors encoding tetracycline-dependent repressors and transactivators for reversible knockdown of gene expression: a comparative study" (BMC Biotechnology: published Jul. 16, 2007: vol. 7, No. 41, pp. 1-10).*

Zhang et al in "A more efficient RNAi inducible system for tight regulation of gene expression in mammalian cells and xenograft animals" (RNA: 2007: vol. 13, pp. 1375-1383, published Jul. 6, 2007).*

SCORE result downloaded Jan. 2013 for SEQ ID No. 1 to Maclachlan et al WO2006/002538.*

Yves et al in "Conditional inhibition of cancer cell proliferation by tetracycline-responsive, H1 promoter-driven silencing of PLK1" (Oncogene, 2005: vol. 24, pp. 2973-2980).*

Agha-Mohammadi, S., et al. (2000). Regulatable Systems: applications in gene therapy and replicating viruses. J. Clin. Invest. 105:1177-1183.

Atkinson, M.R., et al. (2003). Development of genetic circuitry exhibiting toggle switch or oscillatory behavior in *Escherichia coli*. Cell 113, 597-607.

Banaszynski, L.A., et al. (2006). A rapid, reversible, and tunable method to regulate protein function in living cells using synthetic small molecules. Cell 126, 995-1004.

Basu, S., et al. (2004). Spatiotemporal control of gene expression with pulse-generating networks. Proc. Natl. Acad. Sci. USA 101, 6355-6360.

Becskei, A., et al. (2000). Engineering stability in gene networks by autoregulation. Nature 405, 590-593.

Blake, W.J., et al. (2003). Noise in eukaryotic gene expression. Nature 422, 633-637.

Cavazzano-Calvo, M., et al. (2000). Gene therapy of human severe combined immunodeficiency (SCID)-X1 disease. Science. 288:669-72.

Danielian, P.S., et al. (1998). Modification of gene activity in mouse embryos in utero by a tamoxifen-inducible form of Cre recombinase. Curr. Biol. 8, 1323-1326.

Gould, J.D. (2002). Inducible diabetes and transgene expression in a single mouse: a tool to elucidate autoimmune mechanisms. Transgenic Research, 11(6); 583-585.

(Continued)

*Primary Examiner* — Catherine S Hibbert
(74) *Attorney, Agent, or Firm* — Nixon Peabody LLP

(57) ABSTRACT

The present invention relates generally the field of genetics, in particular methods, compositions and systems for controlling the inducible expression of transgenes, while eliminating background expression of transgene expression. The present invention relates to methods of use of the compositions and systems as disclosed herein for controlling the inducible expression of transgenes while eliminating background expression of transgene expression, such as use in, for example, the in generation of transgenic animals, use in therapeutic application and use in assays. In some embodiments, the present invention relates to a system of controlled expression of RNAi molecules which target binding sites in the untranslated regions of transgene, thereby the expression of the transgene is modulated and leakiness is reduced. The compositions and methods of the present invention can be used to for therapy, prophylaxis, research and diagnostics in diseases and disorders which afflict mammalian species, generation of transgenic animals, in the study of biological processes as well as for enhance performance of agricultural crops.

19 Claims, 12 Drawing Sheets

(56) References Cited

OTHER PUBLICATIONS

Elowitz, M.B., et al. (2000). A synthetic oscillatory network of transcriptional regulators. Nature 403, 335-338.
Elowitz, M.B., et al. (2002). Stochastic gene expression in a single cell. Science 297, 1183-1186.
Fire, A., et al. (1998). Potent and specific genetic interference by double-stranded RNA in Caenorhabditis elegans. Nature 391, 806-811.
Freundlieb, S., et al. (1999). A tetracycline controlled activation/repression system with increased potential for gene transfer into mammalian cells. J Gene Med. 1: 4-12.
Fung, E., et al. (2005). A synthetic gene-metabolic oscillator. Nature 435, 118-122.
Furth, P. A., et al. (1994). Temporal control of gene expression in transgenic mice by tetracycline responsive promoter. Proc. Natl. Acad Sci. USA 91, 9302-9306.
Gardner, T.S., et al. (2000). Construction of a genetic toggle switch in *Escherichia coli*. Nature 403, 339342.
Gossen, M., et al. (1992). Tight control of gene expression in mammalian cells by tetracycline-responsive promoters. Proc. Natl. Acad. Sci. USA 89, 5547-5551.
Gossen, M., et al. (1995). Transcriptional activation by tetracyclines in mammalian cells. Science 268(5218), 1766-1769.
Greenfield, L., et al. (1983). Nucleotide sequence of the structural gene for diphtheria toxin carried by corynebacteriophage beta. Proc. Natl. Acad. Sci. USA 80, 6853-6857.
Guet, C.C., et al. (2002). Combinatorial synthesis of genetic networks. Science 296, 1466-1470.
Guido, N.J., et al. (2006). A bottom-up approach to gene regulation. Nature 439, 856-860.
Guo, S., et al. (1995). par-1, a gene required for establishing polarity in C. elegans embroys, encodes a putative Ser/Thr kinase that is asymmetrically distributed. Cell 81, 611-620.
Hallahan, D.E., et al. (1995). Spatial and temporal control of gene therapy using ionizing radiation. Nature Medicine, 1 (8), 786-791.
Hauck W., et al. (1995). Transcriptional regulation of the carcinoembryonic antigen gene; identification of regulatory elements and multiple nuclear factors. J Biol Chem. 270:3602-3610.
Hooshangi, S., et al. (2005). Ultrasensitivity and noise propagation in a synthetic transcriptional cascade. Proc. Natl. Acad. Sci. USA 102, 3581-3586.
Imai, T., et al. (2001). Impaired adipogenesis and lipolysis in the mouse upon selective ablation of the retinoid X receptor alpha mediated by a tamoxifen-inducible chimeric Cre recombinase (Cre-ERT2) in adipocytes. Proc. Natl. Acad. Sci. USA 98, 224-228.
Isaacs, F.J., et al. (2003). Prediction and measurement of an autoregulatory genetic module. Proc. Natl. Acad. Sci. USA 100, 7714-7719.
Isaacs, F.J., et al. (2004). Engineered riboregulators enable post-transcriptional control of gene expression. Nat. Biotechnol. 22, 841-847.
Isalan, M., et al. (2005). Engineering gene networks to emulate *Drosophila* embryonic pattern formation. PLoS Biol. 3, e64.
Kobayashi, H., et al. (2004). Programmable cells: interfacing natural and engineered gene networks. Proc. Natl. Acad. Sci. USA 101, 8414-8419.
Kramer, B.P., et al. (2005). Hysteresis in a synthetic mammalian gene network. Proc. Natl. Acad. Sci. USA 102, 9517-9522.
Kramer, B.P., et al. (2004). An engineered epigenetic transgene switch in mammalian cells. Nat. Biotechnol. 22, 867-870.
Malphettes, L., et al. (2006). Improved transgene expression fine-tuning in mammalian cells using a novel transcription-translation network. J. Biotechnol. 124, 732-746.
Ornitz, D.M., et al. (1991). Binary system for regulating transgene expression in mice: targeting int-2 gene expression with yeast GAL4/UAS control elements. Proc. Natl. Acad. Sci. USA 88, 698-702.
Ozbudak, EM., et al. (2002). Regulation of noise in the expression of a single gene. Nat. Genet. 31, 69-73.
Paddison, P.J., et al. (2004). A resource for large-scale RNA-interference-based screens in mammals. Nature 428, 427-431.
Pedraza, J.M., et al. (2005). Noise propagation in gene networks. Science 307, 1965-1969.
Prywes, R., et al. (1988). Phosphorylation of serum response factor, a factor that binds to the serum response element of the c-FOS enhancer. Proc. Natl. Acad. Sci. USA 85, 7206-7210.
Rosenfeld, N., et al. (2002). Negative autoregulation speeds the response times of transcription networks. J. Mol. Biol. 323, 785-793.
Rosenfeld, N., et al. (2005). Gene regulation at the single-cell level. Science 307, 1962-1965.
Ryffel, B. (1997). Interleukin-12: role of interferon-gamma in IL-12 adverse effects. Clinical Immunology and Immunopathology 83(1):18-20.
Schultze, N., et al. (1996). Efficient control of gene expression by single step integration of the tetracycline system in transgenic mice. Nature Biotechnology 14(4), 499-503.
Scrable, H. (2002). Say when: reversible control of gene expression in the mouse by lac. Semin. Cell Dev. Biol. 13, 109-119.
Siegel, J.P., et al. (1991). Interleukin-2 toxicity. J. Clinical Oncology 9(4), 696-704.
Shinoura, N., et al. (1999). Relative level of expression of Bax and Bcl-XL determines the cellular fate of apoptosis/necrosis induced by the overexpression of Bax. Oncogene 18, 5703-5713.
Soriano, P. (1999). Generalized lacZ expression with the ROSA26 Cre reporter strain. Nat. Genet. 2170-71.
Szulc, J., et al. (2006). A versatile tool for conditional gene expression and knockdown. Nat. Methods 3, 109-116.
van Engeland, M., et al. (1998). Annexin V-affinity assay: a review on an apoptosis detection system based on phosphatidylserine exposure. Cytometry 31, 1-9.
Voellmy, R., et al., (1985). Isolation and functional analysis of a human 70,000-dalton heat shock protein gene segment. Proc. Natl. Acad. Sci. USA, 82:4949-4953.
Weischelbaum, R.R., et al. (1994) Gene therapy targeted by radiation preferentially radiosensitizes tumor cells. Cancer Res. 54:4266-4269.
Wolter, KG., et al. (1997). Movement of Bax from the cytosol to mitochondria during apoptosis. J. Cell Biol. 139, 1281-1292.
You, L., et al. (2004). Programmed population control by cell-cell communication and regulated killing. Nature 428, 868-871.
Yu, Z., Redfern, C. S., arid Fishman, G. I. (1998). Conditional transgene expression in the heart. Circ.Res. 79(4), 691-697.
Kim, D.H. et al., "Argonaute-1 directs siRNA-mediated transcriptional gene silencing in human cells." Nat Struct Mol Biol. 13(9):793-7, 2006.
Epanchintsev, A. et al., "Inducible microRNA expression by an all-in-one episomal vector system." Nucleic Acids Res. 34(18):e119, 2006.
Deans, T.L. et al., "A tunable genetic switch based on RNAi and repressor proteins for regulating gene expression in mammalian cells." Cell. 130(2):363-72, 2007.
Brown et al., "lac Repressor Can Regulate Expression from a Hybrid SV40 Early Promoter Containing a lac Operator in Animal Cells" Cell 49:603-612 (1987).
Hu et al., "The Inducible lac Operator-Repressor System Is Functional in Mammalian Cells" Cell 48:555-566 (1987).
Joki et al., "Activation of the Radiosensitive EGR-1 Promoter Induces Expression of the Herpes Simplex Virus Thymidine Kinase Gene and Sensitivity of Human Glioma Cells to Ganciclovir" Human Gene Ther. 6:1507-1513 (1995).
Kay et al., "Evidence for gene transfer and expression of factor IX in haemophilia B patients treated with an AAV vector" 24:257-261 (2000).
Kramer et al., "Semi-synthetic mammalian gene regulatory networks" Metab. Eng. 7:241-250 (2005).
Opperman et al., "Root-Knot Nematode-Directed Expression of a Plant Root-Specific Gene" Science 263:221-223 (1994).
Richards et al., "Transcriptional Regulatory Sequences of Carcinoembryonic Antigen: Identification and Use with Cytosine Deaminase for Tumor-Specific Gene Therapy" Human Gene Ther. 6:881-893 (1995).

(56) References Cited

OTHER PUBLICATIONS

Siegel et al., "Interleukin-2 Toxicity" J. Clin. Oncol. 9:694-704 (1991).

Spriggs et al., "Tumor Necrosis Factor: the molecules and their emerging roles in medicine" Beutler ed., Rave Press, New York, NY 383-406 (1992).

Sternberg et al., "Bacteriophage P1 Site-specific Recombination I. Recombination Between loxP Sites" J. Mol. Biol. 150:467-486 (1981).

Treisman et al., "Identification of a Protein-Binding Site That Mediates Transcriptional Response of the c-fos Gene to Serum Factors" Cell 46:567-574 (1986).

Yamaizumi et al., "One Molecule of Diphtheria Toxin Fragment A Introduced into a Cell Can Kill the Cell" Cell 15:245-250 (1978).

Agrawal et al. "RNA Interference: Biology, Mechanism, and Applications." Microbiology and Molecular Biology Reviews, Dec. 2003, p. 657-685.

* cited by examiner

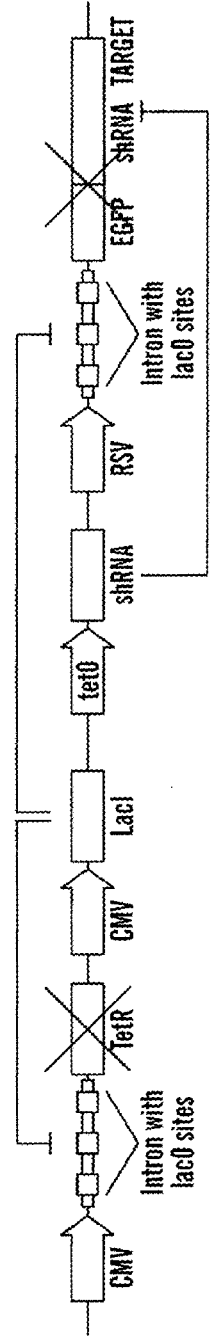
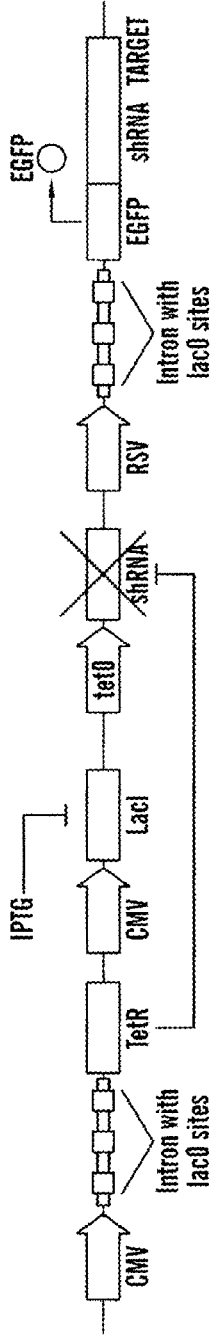
FIG. 1A
FIG. 1B

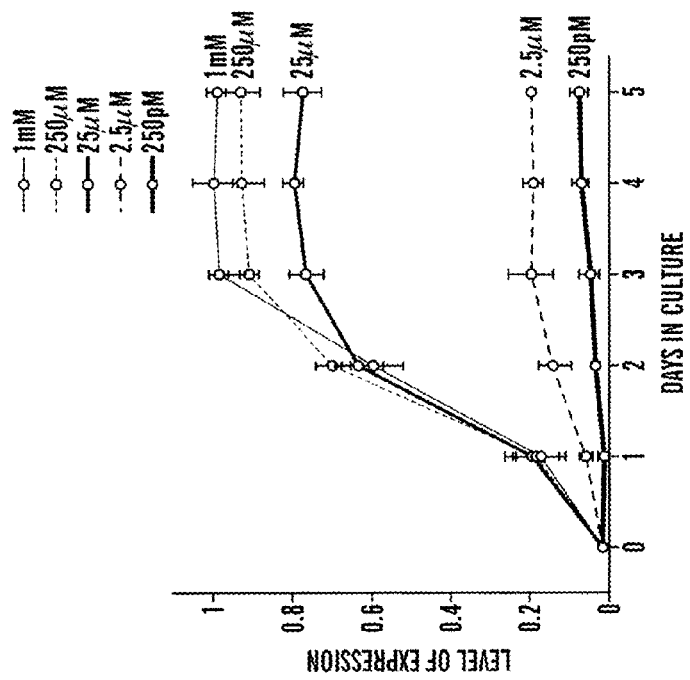
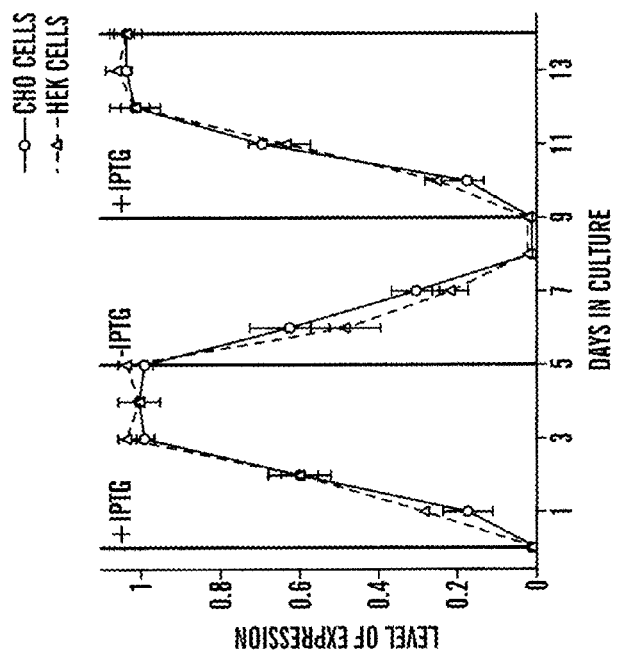
FIG. 3A
FIG. 3B

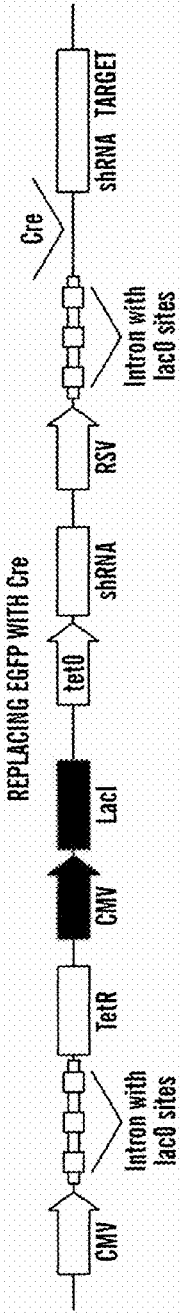
FIG. 5A
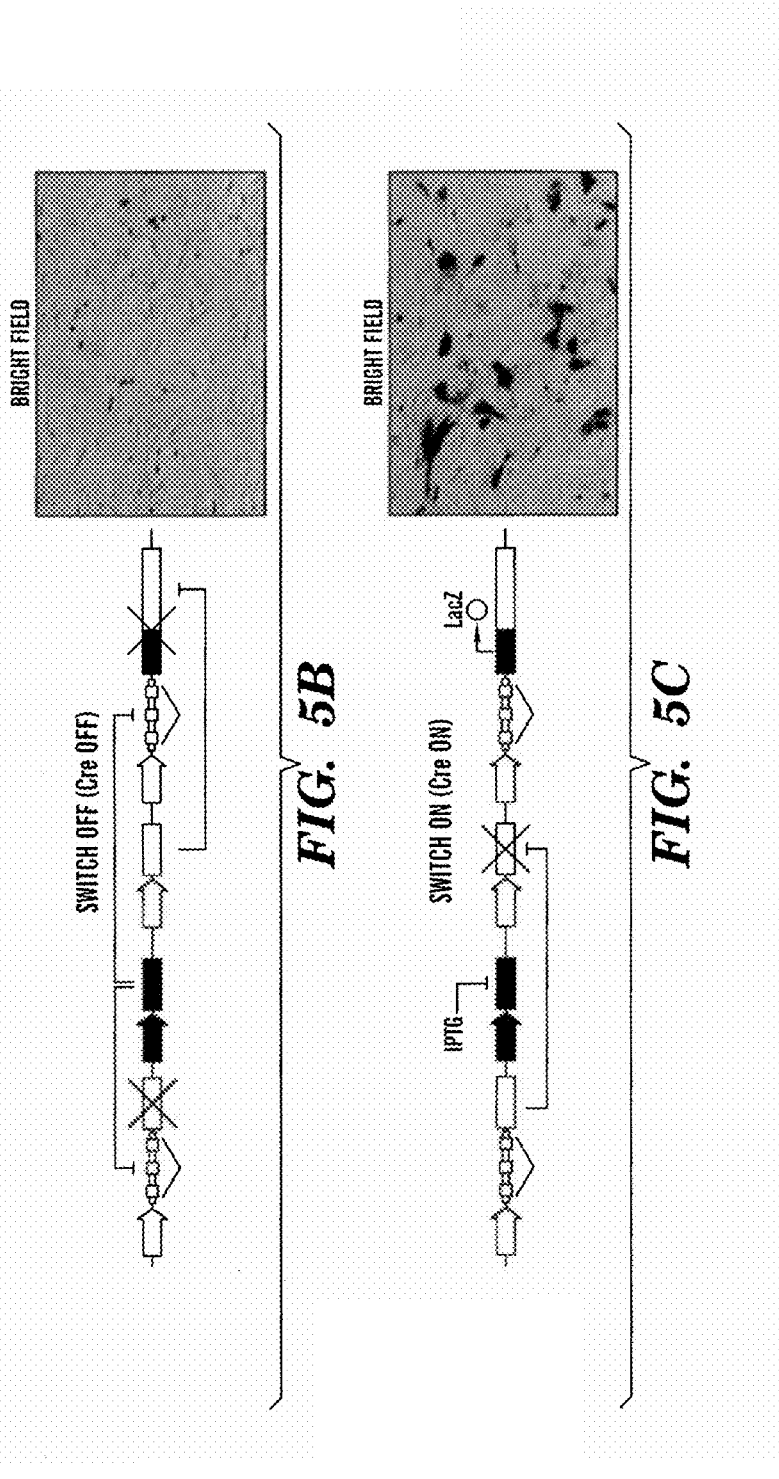
FIG. 5B
FIG. 5C

SEQUENCE LISTING

```
<160> NUMBER OF SEQ ID NOS: 4

<210> SEQ ID NO 1
<211> LENGTH: 19
<212> TYPE: DNA
<213> ORGANISM: Homo sapiens

<400> SEQUENCE: 1
ctacacaaat cagcgattt                                               19

<210> SEQ ID NO 2
<211> LENGTH: 19
<212> TYPE: DNA
<213> ORGANISM: Homo sapiens

<400> SEQUENCE: 2
atacaaagga tatcaggtg                                               19

<210> SEQ ID NO 3
<211> LENGTH: 2588
<212> TYPE: DNA
<213> ORGANISM: Homo sapiens

<400> SEQUENCE: 3
aggcgcgagg gctggctgct gggccgacga ggggcggtgc caggccgtgg gtccttagtc    60
aagtgacgcg aagcggccgg cctgggcgcc gactgcagag ccgggaggct ggtggtcatg   120
ccggggttcc tggttcgcat cctccctctg ttgctggttc tgctgcttct gggccctacg   180
cgcggcttgc gcaatgccac ccagaggatg tttgaaattg actatagccg ggactccttc   240
ctcaaggatg gccagccatt tcgctacatc tcaggaagca ttcactactc ccgtgtgccc   300
cgcttctact ggaaggaccg gctgctgaag atgaagatgg ctgggctgaa cgccatccag   360
acgtatgtgc cctggaactt tcatgagccc tggccaggac agtaccagtt ttctgaggac   420
catgatgtgg aatattttct tcggctggct catgagctgg gactgctggt tatcctgagg   480
cccgggccct acatctgtgc agagtgggaa atgggaggat tacctgcttg gctgctagag   540
aaagagtcta ttcttctccg ctcctccgac ccagattacc tggcagctgt ggacaagtgg   600
ttgggagtcc ttctgcccaa gatgaagcct ctcctctatc agaatggagg gccagttata   660
acagtgcagg ttgaaaatga atatgcagc tactttgcct gtgatttga ctacctgcgc    720 ttcctgcaga agcgctttcg ccaccatctg ggggatgatg tggttctgtt taccactgat   780
ggagcacata aacattcct gaaatgtggg gccctgcagg gcctctacac cacggtggac   840
tttggaacag gcagcaacat cacagatgct ttcctaagcc agaggaagtg tgagcccaaa   900
```

```
ggacccttga tcaattctga attctatact ggctggctag atcactgggg ccaacctcac    960
tccacaatca agaccgaagc agtggcttcc tccctctatg atatacttgc ccgtggggcg   1020
agtgtgaact tgtacatgtt tataggtggg accaattttg cctattggaa tggggccaac   1080
tcaccctatg cagcacagcc caccagctac gactatgatg ccccactgag tgaggctggg   1140
gacctcactg agaagtattt tgctctgcga acatcatcc agaagtttga aaaagtacca    1200
gaaggtccta tccctccatc tacaccaaag tttgcatatg gaaaggtcac tttggaaaag   1260
ttaaagacag tgggagcagc tctggacatt ctgtgtccct ctgggcccat caaaagcctt   1320
tatcccttga catttatcca ggtgaaacag cattatgggt tgtgctgta ccggacaaca    1380 cttcctcaag attgcagcaa cccagcacct ctctcttcac ccctcaatgg agtccacgat   1440
cgagcatatg ttgctgtgga tgggatcccc caggagtcc ttgagcgaaa caatgtgatc    1500
actctgaaca taacagggaa agctggagcc actctggacc ttctggtaga gaacatggga   1560
cgtgtgaact atggtgcata tatcaacgat tttaagggtt tggtttctaa cctgactctc   1620
agttccaata tcctcacgga ctggacgatc tttccactgg acactgagga tgcagtgcgc   1680
agccacctgg ggggctgggg acaccgtgac agtggccacc atgatgaagc ctgggcccac   1740
aactcatcca actacacgct cccggccttt tatatgggga acttctccat tcccagtggg   1800
atcccagact tgccccagga caccttatc cagtttcctg gatggaccaa gggccaggtc    1860
tggattaatg gctttaacct tggccgctat tggccagccc ggggccctca gttgaccttg   1920
tttgtgcccc agcacatcct gatgacctcg gccccaaaca ccatcaccgt gctggaactg   1980
gagtgggcac cctgcagcag tgatgatcca gaactatgtg ctgtgacgtt cgtggacagg   2040
ccagttattg gctcatctgt gacctacgat catccctcca aacctgttga aaaaagactc   2100 atgccccccac ccccgcaaaa aaacaaagat tcatggctgg accatgtatg atgatgaaag  2160
cctgtgtctt tgagggattc taccctgaac atacctcaca gatcctccct gtcatgccac   2220
atttcactga ttggaatgtg gaaatggaaa aggaatttag gatgtgcatt ttcacctgag   2280
gtttccctgc atccctgcag tgccaaagcc ccaccttcag ggaccacctg gaatgtgtga   2340
ggggctgaca gcacagtaac gtgcatacat atctgcaggg ctggaatgga agctttaaag   2400
gtggtagtga ttttatttt ggaagaatca tgttacccttt ttgttaaata aaatttgtac    2460
tcaaatgatg atgtcactgt ttttaatgtg caggtattga attatatggt ctgacttaaa   2520
tcataactag acttgagtgg gctgaataaa ccacttcact aacttgaagt tcaaaaggat   2580
ggaaaata                                                            2588
```

<210> SEQ ID NO 4
<211> LENGTH: 11870
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: modified_base
<222> LOCATION: (7633)
<223> OTHER INFORMATION: a, t, g, c, unknown or other

<400> SEQUENCE: 4

```
tcgcgcgttt cggtgatgac ggtgaaaacc tctgacacat gcagctcccg gagacggtca     60
cagcttgtct gtaagcggat gccggagca gacaagcccg tcaggcgcg tcagcgggtg      120 ttggcgggtg tcggggctgg cttaactatg cggcatcaga gcagattgta ctgagagtgc    180
```

```
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt atcctgctcc ctgcttgtgt      420
gttggaggtc gctgagtagt gcgcgagcaa aatttaagct acaacaaggc aaggcttgac      480
cgacaattgc atgaagaatc tgcttagggt taggcgtttt gcgctgcttc gcgatgtacg      540
ggccagatat acgcgtatct gaggggacta gggtgtgttt aggcgaaaag cggggcttcg      600
gttgtacgcg gttaggagtc ccctcaggat atagtagttt cgcttttgca tagggagggg      660
gaaatgtagt cttatgcaat actcttgtag tcttgcaaca tggtaacgat gagttagcaa      720
catgccttac aaggagagaa aaagcaccgt gcatgccgat tggtggaagt aaggtggtac      780
gatcgtgcct tattaggaag gcaacagacg ggtctgacat ggattggacg aaccactgaa      840
ttccgcattg cagagatatt gtatttaagt gcctagctcg atacaataaa cgccatttga      900
ccattcacca cattggtgtg caccagatct aagcttggac aaaactaccta cagagattta      960 aagctctaag gtaaatataa aatttactag gttgtgaat tgtgagcgct cacaattcca      1020
cagtcgaccc taggttgtgg aattgtgagc gctcacaatt ccacagtcga ccctaggttg     1080
tggaattgtg agcgctcaca attccacagt cgaccctagt gtataatgtg ttaaactacg     1140
gatccgtctc ccattaggcc tacaatggtg agacaagtag ccaacaggga agggttgcaa     1200
atatcatttg ggcacaccta tgataatatt gatgaagcag acagtattca gcaagtaact     1260
gagaggtggg aagctcaaag ccaaagtcct aatgtgcagt caggtgaatt tattgaaaaa     1320
tttgaggctc ctggtggtgc aaatcaaaga actgctcctc agggatccta attgtttgtg     1380
tattttagat tccaaccaag cttgcggccg ctcaggagct aaggaattga tcctctagag     1440
tcgacctgca gcacaaccat ggtgagcaag ggcgaggagc tgttcaccgg ggtggtgccc     1500
atcctggtcg agctggacgg cgacgtaaac ggccacaagt tcagcgtgtc cggcgagggc     1560
gagggcgatg ccacctacgg caagctgacc ctgaagttca tctgcaccac cggcaagctg     1620
cccgtgccct ggcccaccct cgtgaccacc ctgacctacg gcgtgcagtg cttcagccgc     1680
taccccgacc acatgaagca gcacgacttc ttcaagtccg ccatgcccga aggctacgtc     1740
caggagcgca ccatcttctt caaggacgac ggcaactaca agacccgcgc cgaggtgaag     1800
ttcgagggcg acaccctggt gaaccgcatc gagctgaagg gcatcgactt caaggaggac     1860
ggcaacatcc tggggcacaa gctggagtac aactacaaca gccacaacgt ctatatcatg     1920
gccgacaagc agaagaacgg catcaaggtg aacttcaaga tccgccacaa catcgaggac     1980
ggcagcgtgc agctcgccga ccactaccag cagaacaccc catcggcga cggccccgtg     2040 ctgctgcccg acaaccacta cctgagcacc cagtccgccc tgagcaaaga ccccaacgag     2100
aagcgcgatc acatggtcct gctggagttc gtgaccgccg ccgggatcac tctcggcatg     2160
gacgagctgt acaagtaaag cggccgcgac tctagatcat aatcagccat accacatttg     2220
tagaggtttt acttgcttta aaaaacctcc cacacctccc cctgaacctg aaacataaaa     2280
tgaatgcact acacaaatca gcgattttaa tggttacaaa taaagcaata gcatcacaaa     2340
tttcacaaat aaagcatttt tttcactgca agcttggcgt aatcatggtc atagctgttt     2400
cctgtgtgaa attgttatcc gctcacaatt ccacacaaca tacgagccgg aagcataaag     2460
tgtaaagcct ggggtgccta atgagtgagc taactcacat taattgcgtt gcgctcactg     2520
```

```
cccgctttcc agtcgggaaa cctgtcgtgc cagctgcatt aatgaatcgg ccaacgcgcg   2580
gggagaggcg gtttgcgtat tgggcgctct tccgctgcaa ctgttgggaa gggcgatcgg   2640
tgcgggcctc ttcgctatta cgccagctgg cgaaggggg  atgtgctgca aggcgattaa   2700
gttgggtaac gccagggttt tcccagtcac gacgttgtaa aacgacggcc agtgaattgt   2760
aatacgactc actatagggc gaattgggcc ttttctaca  caaatcagcg attttctctt   2820
gaaaaatcgc tgatttgtgt agcggtgttt cgtcctttcc acaagatata taactctatc   2880
aatgatagag tactttcaag ttacggtaag catatgatag tccattttaa aacataattt   2940
taaaactgca aactacccaa gaaattatta ctttctacgt cacgtatttt gtactaatat   3000
ctttgtgttt acagtcaaat taattctaat tatctctcta acagccttgt atcgtatatg   3060
caaatatgaa ggaatcatgg gaaataggcc ctcttcctgc ccgaccttgg cgcgcgctcg   3120
gcgcgcggtc acgctccgtc acgtggtgcg ttttgcctaa tcactagtga attctagtta   3180
ttaatagtaa tcaattacgg ggtcattagt tcatagccca tatatggagt tccgcgttac   3240
ataacttacg gtaaatggcc cgcctggctg accgcccaac gacccccgcc cattgacgtc   3300
aataatgacg tatgttccca tagtaacgcc aatagggact ttccattgac gtcaatgggt   3360
ggagtattta cggtaaactg cccacttggc agtacatcaa gtgtatcata tgccaagtac   3420
gccccctatt gacgtcaatg acggtaaatg gcccgcctgg cattatgccc agtacatgac   3480
cttatgggac tttcctactt ggcagtacat ctacgtatta gtcatcgcta ttaccatggt   3540
gatgcggttt tggcagtaca tcaatgggcg tggatagcgg tttgactcac ggggatttcc   3600
aagtctccac cccattgacg tcaatgggag tttgttttgg caccaaaatc aacgggactt   3660
tccaaaatgt cgtaacaact ccgccccatt gacgcaaatg ggcggtaggc gtgtacggtg   3720
ggaggtctat ataagcagag ctggtttagt gaaccgtcag atcggatcct ctagagtcga   3780
ccattgccgc caccatgaaa ccagtaacgt tatacgatgt cgcagagtat gccggtgtct   3840
cttatcagac cgtttcccgc gtggtgaacc aggccagcca cgtttctgcg aaaacgcggg   3900
aaaaagtgga agcggcgatg gcggagctga attacattcc caaccgcgtg gcacaacaac   3960
tggcgggcaa acagtcgttg ctgattgcg  ttgccacctc cagtctggcc ctgcacgcgc   4020
cgtcgcaaat tgtcgcggcg attaaatctc gcgccgatca actgggtgcc agcgtggtgg   4080
tgtcgatggt agaacgaagc ggcgtcgaag cctgtaaagc ggcggtgcac aatcttctcg   4140
cgcaacgcgt cagtgggctg atcattaact atccgctgga tgaccaggat gccattgctg   4200
tggaagctgc ctgcactaat gttccggcgt tatttcttga tgtctctgac cagacaccca   4260
tcaacagtat tattttctcc catgaagacg gtacgcgact gggcgtggag catctggtcg   4320
cattgggtca ccagcaaatc gcgctgttag cgggcccatt aagttctgtc tcggcgcgtc   4380
tgcgtctggc tggctggcat aaatatctca ctcgcaatca aattcagccg atagcggaac   4440
gggaaggcga ctggagtgcc atgtccggtt ttcaacaaac catgcaaatg ctgaatgagg   4500
gcatcgttcc cactgcgatg ctggttgcca acgatcagat ggcgctgggc gcaatgcgcg   4560
ccattaccga gtccgggctg cgcgttggtg cggatatctc ggtagtggga tacgacgata   4620
ccgaagacag ctcatgttat atcccgccgt taaccaccat caaacaggat tttcgcctgc   4680
tggggcaaac cagcgtggac cgcttgctgc aactctctca gggccaggcg gtgaagggca   4740
atcagctgtt gcccgtctca ctggtgaaaa gaaaaccac  cctggcgccc aatacgcaaa   4800
ccgcctctcc ccgcgcgttg gccgattcat taatgcagct ggcacgacag gtttcccgac   4860
tggaaagcgg gcagagcagc ctgaggcctc ctaagaagaa gaggaaggtt tgagcgcaac   4920
```

```
gcaattaatg taagttagct cactcattag gcaccccagg ctttacactt tatgcttccg   4980
acctgcagcc ccttggatct ttgtgaagga accttacttc tgtggtgtga cataattgga   5040
caaactacct acagagattt aaagctctaa ggtaaatata aaatttttaa gtgtataatg   5100
tgttaaacta ctgattctaa ttgtttgtgt attttagatc acagtcccaa ggctcatttc   5160
aggcccctca gtcctcacag tctgttcatg atcataatca gccataccac atttgtagag   5220
gttttacttg cttttaaaaaa cctcccacac ctcccccctga acctgaaaca taaaatgaat   5280
gcaattgttg ttgttaactt gtttattgca gcttataatg gttacaaata aagcaatagc   5340
atcacaaatt tcacaaataa agcatttttt tcactgcatt ctagttgtgg tttgtccaaa   5400
ctcatcaatg tatcttatca tgtctgggcc caagcttggc gtaatcatgg tcatagctgt   5460
ttcctgtgtg aaattgttat ccgctcacaa ttccacacaa catacgagcc ggaagcataa   5520
agtgtaaagc ctggggtgcc taatgagtga gctaactcac attaattgcg ttgcgctcac   5580
tgcccgcttt ccagtcggga aacctgtcgt gccagctgca ttaatgaatc ggccaacgcg   5640
cggggagagg cggtttgcgt attgggcgct cttccgcttc ctcgctcact gactcgctgc   5700
gctcggtcgt tcggctgcgg cgagcggtat cagctcactc aaaggcggta atacggttat   5760
ccacagaatc aggggataac gcaggaaaga acatgacatg tggccctcta gactcgacac   5820
gttttggccg aagttcctat tctctagaaa gtataggaac ttcgcggcca attctaccgg   5880
gtaggggagg cgcttttccc aaggcagtct ggagcatgcg ctttagcagc cccgctgggc   5940
acttggcgct acacaagtgg cctctggcct cgcacacatt ccacatccac cggtaggcgc   6000
caaccggctc cgttctttgg tggccccttc gcgccacctt ctactcctcc cctagtcagg   6060
aagttccccc ccgccccgca gctcgcgtcg tgcaggacgt gacaaatgga agtagcacgt   6120
ctcactagtc tcgtgcagat ggacagcacc gctgagcaat ggaagcgggt aggcctttgg   6180
ggcagcggcc aatagcagct ttgctccttc gctttctggg ctcagaggct gggaaggggt   6240
gggtccgggg gcgggctcag gggcgggctc aggggcgggg cgggcgcccg aaggtcctcc   6300
ggaggcccgg cattctgcac gcttcaaaag cgcacgtctg ccgcgctgtt ctcctcttcc   6360
tcatctccgg gcctttcgac ctgcagccaa tatgggatcg gccattgaac aagatggatt   6420
gcacgcaggt tctccggccg cttgggtgga ggctattcgg ctatgactgg gcacaaca   6480
gacaatcggc tgctctgatg ccgccgtgtt ccggctgtca gcgcagggc gcccggttct   6540
ttttgtcaag accgacctgt ccggtgccct gaatgaactg caggacgagg cagcgcggct   6600
atcgtggctg gccacgacgg cgttccttg cgcagctgtg ctcgacgttg tcactgaagc   6660
gggaagggac tggctgctat tgggcgaagt gccggggcag gatctcctgt catctcacct   6720
tgctcctgcc gagaaagtat ccatcatggc tgatgcaatg cggcggctgc atacgcttga   6780
tccggctacc tgcccattcg accaccaagc gaaacatcgc atcgagcgag cacgtactcg   6840
gatggaagcc ggtcttgtcg atcaggatga tctggacgaa gagcatcagg gctcgcgcc   6900
agccgaactg ttcgccaggc tcaaggcgcg catgcccgac ggcgaggatc tcgtcgtgac   6960
ccatggcgat gcctgcttgc cgaatatcat ggtggaaaat ggccgctttt ctggattcat   7020
cgactgtggc cggctgggtg tggcggaccg ctatcaggac atagcgttgg ctacccgtga   7080
tattgctgaa gagcttggcg gcgaatgggc tgaccgcttc ctcgtgcttt acggtatcgc   7140
cgctcccgat tcgcagcgca tcgccttcta tcgccttctt gacgagttct tctgagggga   7200
tccgctgtaa gtctgcagaa attgatgatc tattaaacaa taaagatgtc cactaaaatg   7260
```

```
gaagtttttc ctgtcatact tgttaagaa gggtgagaac agagtaccta catttttgaat    7320 ggaaggattg gagctacggg ggtggggtg gggtgggatt agataaatgc ctgctctta     7380 ctgaaggctc tttactattg ctttatgata atgtttcata gttggatatc ataatttaaa    7440
caagcaaaac caaattaagg gccagctcat tcctcccact catgatctat agatctatag    7500
atctctcgtg ggatcattgt ttttctcttg attcccactt tgtggttcta agtactgtgk    7560
ttyccaaatg tgtcagtttc atagcctgaa gaacgagatc agcagcctct gttccaacat    7620
acacttcatt ctncagtatt gttttgccaa gttctaattc catcagaagc ttatcgatac    7680
ccgtcgaggg aagttcctat tctctagaaa gtataggaac ttcgtcgagc ggccgccagt    7740
gtgatggatt cgaccagaca tgataagata cattgatgag tttggacaaa ccacaactag    7800
aatgcagtga aaaaaatgct ttatttgtga aatttgtgat gctattgctt tatttgtaac    7860
cattataagc tgcaataaac aagttctgct ttaataagat ctgaattccc gggatccgct    7920
gtacgcggac ccactttcac atttaagttg tttttctaat ccgcatatga tcaattcaag    7980
gccgaataag aaggctggct ctgcaccttg gtgatcaaat aattcgatag cttgtcgtaa    8040
taatggcggc atactatcag tagtaggtgt ttccctttct tctttagcga cttgatgctc    8100
ttgatcttcc aatacgcaac ctaaagtaaa atgccccaca gcgctgagtg catataatgc    8160
attctctagt gaaaaacctt gttggcataa aaaggctaat tgattttcga gagtttcata    8220
ctgtttttct gtaggccgtg tacctaaatg tacttttgct ccatcgcgat gacttagtaa    8280
agcacatcta aaactttttag cgttattacg taaaaaatct tgccagcttt cccttctaa     8340 agggcaaaag tgagtatggt gcctatctaa catctcaatg gctaaggcgt cgagcaaagc    8400
ccgcttattt ttttacatgcc aatacaatgt aggctgctct acacctagct tctgggcgag    8460
tttacgggtt gttaaaccttt cgattccgac ctcattaagc agctctaatg cgctgttaat    8520
cactttactt ttatctaatc tagacatatc aattcgccct atagtgagtc gtattacaat    8580
tctttgccaa aatgatgaga cagcacaata accagcacgt tgcccaggag ctgtaggaaa    8640
aagaagaagg catgaacatg gttagcagag gggcccgttc tttacgatgc cattgggata    8700
tatcaacggt ggtatatcca gtgatttttt tctccatttt agcttcctta gctcctgagc    8760
ggccgcaagc ttggttggaa tctaaaatac acaaacaatt aggatccctg aggagcagtt    8820
ctttgatttg caccaccagg agcctcaaat ttttcaataa attcacctga ctgcacatta    8880
ggactttggc tttgagcttc ccacctctca gttacttgct gaatactgtc tgcttcatca    8940
atattatcat aggtgtgccc aaatgatatt tgcaaccctt ccctgttggc tacttgtctc    9000
accattgtag gcctaatggg agacggatcc gtagtttaac acattataca ctagggtcga    9060
ctgtggaatt gtgagcgctc acaattccac aacctaggt cgactgtgga attgtgagcg    9120
ctcacaattc cacaacctag gtcgactgt ggaattgtga gcgctcacaa ttccacaacc    9180
tagtaaattt tatatttacc ttagagcttt aaatctctgt aggtagtttg tccaagctta    9240
gatcctgcag gtcgactcta gaggatccga tctgacggtt cactaaacca gctctgctta    9300
tatagacctc ccaccgtaca cgcctaccgc ccatttgcgt caatggggcg gagttgttac    9360
gacattttgg aaagtcccgt tgattttggt gccaaaacaa actcccattg acgtcaatgg    9420
ggtggagact tggaaatccc cgtgagtcaa accgctatcc acgccattg atgtactgcc    9480 aaaaccgcat caccatggta atagcgatga ctaatacgta gatgtactgc caagtaggaa    9540
agtcccataa ggtcatgtac tgggcataat gccaggcggg ccatttaccg tcattgacgt    9600
caataggggg cgtacttggc atatgataca cttgatgtac tgccaagtgg gcagtttacc    9660
```

```
gtaaatactc cacccattga cgtcaatgga aagtccctat tggcgttact atgggaacat    9720
acgtcattat tgacgtcaat gggcgggggt cgttgggcgg tcagccaggc gggccattta    9780
ccgtaagtta tgtaacgcgg aactccatat atgggctatg aactaatgac cccgtaattg    9840
attactatta ataactagaa ttcactggcc gtcgttttac aacgtcgtga ctgggaaaac    9900
cctggcgtta cccaacttaa tcgccttgca gcacatcccc ctttcgccag ctggcgtaat    9960
agcgaagagg cccgcaccga ttaagccggc catgtgagca aaaggccagc aaaaggccag   10020
gaaccgtaaa aaggccgcgt tgctggcgtt tttccatagg ctccgccccc ctgacgagca   10080
tcacaaaaat cgacgctcaa gtcagaggtg gcgaaacccg acaggactat aaagatacca   10140
ggcgtttccc cctggaagct ccctcgtgcg ctctcctgtt ccgaccctgc cgcttaccgg   10200
atacctgtcc gcctttctcc cttcgggaag cgtggcgctt tctcatagct cacgctgtag   10260
gtatctcagt tcggtgtagg tcgttcgctc caagctgggc tgtgtgcacg aaccccccgt   10320
tcagcccgac cgctgcgcct tatccggtaa ctatcgtctt gagtccaacc cggtaagaca   10380
cgacttatcg ccactggcag cagccactgg taacaggatt agcagagcga ggtatgtagg   10440
cggtgctaca gagttcttga agtggtggcc taactacggc tacactagaa gaacagtatt   10500
tggtatctgc gctctgctga agccagttac cttcggaaaa agagttggta gctcttgatc   10560
cggcaaacaa accaccgctg gtagcggtgg ttttttttgt tgcaagcagc agattacgcg   10620
cagaaaaaaa ggatctcaag aagatccttt gatcttttct acggggtctg acgctcagtg   10680
gaacgaaaac tcacgttaag ggattttggt catgagatta tcaaaaagga tcttcaccta   10740
gatccttttta aattaaaaat gaagttttaa atcaatctaa agtatatatg agtaaacttg   10800
gtctgacagt taccaatgct taatcagtga ggcacctatc tcagcgatct gtctatttcg   10860
ttcatccata gttgcctgac tccccgtcgt gtagataact acgatacggg agggcttacc   10920
atctggcccc agtgctgcaa tgataccgcg agacccacgc tcaccggctc cagatttatc   10980
agcaataaac cagccagccg aagggccgga gcgcagaagt ggtcctgcaa ctttatccgc   11040
ctccatccag tctattaatt gttgccggga agctagagta agtagttcgc cagttaatag   11100
tttgcgcaac gttgttgcca ttgctacagg catcgtggtg tcacgctcgt cgtttggtat   11160
ggcttcattc agctccggtt cccaacgatc aaggcgagtt acatgatccc ccatgttgtg   11220
caaaaaagcg gttagctcct tcggtcctcc gatcgttgtc agaagtaagt tggccgcagt   11280
gttatcactc atggttatgg cagcactgca taattctctt actgtcatgc catccgtaag   11340
atgcttttct gtgactggtg agtactcaac caagtcattc tgagaatagt gtatgcggcg   11400
accgagttgc tcttgcccgg cgtcaatacg ggataatacc gcgccacata gcagaacttt   11460
aaaagtgctc atcattggaa aacgttcttc ggggcgaaaa ctctcaagga tcttaccgct   11520
gttgagatcc agttcgatgt aacccactcg tgcacccaac tgatcttcag catcttttac   11580
tttcaccagc gtttctgggt gagcaaaaac aggaaggcaa aatgccgcaa aaaagggaat   11640
aagggcgaca cggaaatgtt gaatactcat actcttcctt tttcaatatt attgaagcat   11700
ttatcagggt tattgtctca tgagcggata catatttgaa tgtatttaga aaataaaca   11760
aataggggtt ccgcgcacat ttccccgaaa agtgccacct gacgtctaag aaaccattat   11820
tatcatgaca ttaacctata aaataggcg tatcacgagg ccctttcgtc              11870
```

TUNABLE GENETIC SWITCH FOR REGULATING GENE EXPRESSION

CROSS REFERENCE TO RELATED APPLICATIONS

This application is a 371 National Phase Entry Application of co-pending International Application PCT/US2007/081965 filed Oct. 19, 2007, which designated the U.S., and claims the benefit under 35 U.S.C. 119(e) of U.S. Provisional Patent Application Ser. No. 60/853,357 filed Oct. 20, 2006, the contents of which are incorporated herein by reference in their entirety.

GOVERNMENT SUPPORT

This invention was made with Government support under GM070583 awarded by the National Institutes for Health (NIH). The Government of the Untied States has certain rights in the invention.

FIELD OF THE INVENTION

The present invention relates generally to the field of genetics, in particular methods, compositions and systems for controlling the inducible expression of transgenes, while eliminating background expression of transgene expression. The present invention relates to methods of use of the compositions and systems as disclosed herein for controlling the inducible expression of transgenes while eliminating background expression of transgene expression, for use in, for example, the generation of transgenic animals, therapeutic application and assays and study of biological processes.

BACKGROUND

Synthetic biology is an emerging field that aspires to design and build functioning biological circuits, including gene expression systems, using well-characterized biomolecular components and genetic modules (Atkinson et al., 2003; Basu et al., 2004; Becskei and Serrano, 2000; Blake et al., 2003; Elowitz and Leibler, 2000; Elowitz et al., 2002; Fung et al., 2005; Gardner et al., 2000; Guet et al, 2002; Guido et al., 2006; Hooshangi et al., 2005; tsaacs et al., 2003, 2004; satan et al., 2005; Kobayashi et al., 2004; Kramer et al., 2004, 2005; Kramer and Fussenegger, 2005; Malphettes and Fussenegger, 2006; Ozbudak et al., 2002; Pedraza and van Oudenaarden, 2005; Rosenfeld et al., 2002, 2005; You et al., 2004). Generating high-fidelity and inducible gene expression systems that can operate in an intact organism would assist experimental studies of cellular function, development, and disease.

Several techniques exist to regulate gene expression; however, each carries its own caveat in function. It was discovered that both the tetR and lacI *Escherichia coli* repressor systems function in mammalian cell tissue culture and in mice (Brown et al., 1987; Gossen and Bujard, 1992; Hu and Davidson, 1987; Scrable, 2002), which proved to be a great advance in the understanding of cellular function. Other similar techniques have been used, including the inducible Gal4/UAS system, to control gene expression at the transcriptional level (Ornitz et al., 1991). While these techniques offer good repression, they exhibit leakiness that precludes the gene of interest from being completely turned off. Studies performed with double-stranded RNA in the nematode *Caenorhabditis elegans* revealed a sequence-specific RNA-mediated pathway for turning off gene expression (Fire et al., 1998; Guo and Kemphues, 1995). This process, known as RNA interference (RNAi), has been adapted for use in tissue culture and mammals with the introduction of small interfering RNAs (siRNAs) and short-hairpin RNAs (shRNAs). RNAi has revolutionized biological research; however, targeting locations on mRNAs for robust knock-down is empirical and often requires screening very large numbers of selected mRNA sequences (Paddison et al., 2004). Additionally, off-target effects can affect genes not related to the gene of interest. A commonly used method to activate or inactivate gene expression in mice involves the use of site-specific cre recombinase (cre). cre, which was derived from bacteriophage P1, mediates the deletion of a DNA sequence flanked by a pair of cre recognition sequences, called IoxP sites (Sternberg and Hamilton, 1981). A disadvantage of this approach is that it is dependent on the coexpression of the transgene cre, which causes a permanent genetic event, restricting any regulation of gene expression. This approach can be made inducible with the application of cre-ERTM or ERT2 fusion proteins; however, the inducing ligand, tamoxifen, can be toxic at the dosage levels required for recombination (Danielian et al., 1998; Imai et al., 2001). The caveats associated with these systems for regulating gene expression make it difficult to study many fundamental questions concerning cellular processes and disease.

Further, one of the major obstacles in various field of biotechnology (including but not limited to gene therapy and plant biotechnology) is the difficulty to achieve cell or tissue specificity. Transcription is an essential process for every living organism to convert abstract genetic information into physical reality.

The promoter is a major component to drive transcription. Some promoters are active in every tissue termed constitutive promoters, such as for e.g. actin promoters, while other promoters are only active in limited tissues. It is quite often that a given promoter is predominantly active in one tissue type but weakly expressed in some other tissues and allows some level of basal or background expression and are termed "leaky promoters" herein. Use of such leaky promoters is undesirable for agriculture and pharmaceutical application because the unintended expression of gene-of-interest resulted from leaky promoters and risk of detrimental effects to crops or patients. It certainty would not meet requirement of regulatory agency.

Unfortunately, for most of the present expression systems the expression of the introduced transgene is not limited to the target site, such as a tumor site, as the available promoters such as tissue-specific promoters or tumor-specific promoters are leaky and therefore the transgene is expressed in other tissue and thereby limits the use and efficiency of such approaches. While tissue specific promoters may add a further degree of control of transgene expression and selectivity, few of these have been validated in vivo and all have some degree of non-specific activation or "leakiness". A versatile mechanism for controllable gene expression is therefore highly desired for gene therapy. A mechanism for controlling gene expression should ideally include both spatial and temporal control of gene expression.

For example a major problem in chemotherapy and radiation therapy for cancer is the difficulty in achieving tumor-specific cell killing. The inability of radiation or cytotoxic chemotherapeutic agents to distinguish between tumor cells and normal cells necessarily limits the dosage that can be applied. As a result, disease relapse due to residual surviving tumor cells is frequently observed, and thus there exists a clear need for alternative non-surgical strategies. Development of gene therapy techniques is approaching clinical realization for the treatment of neoplastic and metabolic diseases, and numerous genes displaying anti-tumor activity have been identified. However, the usefulness of gene therapy methods has been limited due to systemic toxicity of antitumor polypeptides encoded by gene therapy constructs (Spriggs & Yates (1992) in Bentler, ed., Tumor Necrosis Factor: The Molecules and Their Emerging Roles in Medicine, pp. 383-406 Raven Press, New York, N.Y.; Sigel & Puri (1991) J Clin Oncol 9:694-704; Ryffel (1997) Immunopathol 83:18-20). Problems with current state-of-the art gene therapy strategies include the inability to limit gene expression of the therapeutic gene specifically in the target cells. Non-specific gene expression of the therapeutic gene can lead to toxicity and undesired phenotypes in cells that are not the intended targets.

For example, manipulation of the p53 gene suppresses the growth of both tumor cells and normal cells, and intravenous administration of tumor necrosis factor alpha (TNFα) induces systemic toxicity with such clinical manifestations as fever and hypertension. While attempts have been made to overcome these problems, by using strategies utilizing tissue-specific promoters to limit gene expression to specific tissues and the use of heat (Voellmy R., et al., Proc. Natl. Acad. Sci. USA, 82:4949-4953 (1985)) or ionizing radiation inducible enhancers and promoters (Trainman, R. H., et al., Cell 46: 567-574 (1986); Prowess, R., et al., Proc. Natl. Acad. Sci. USA 85, 7206-7210 (1988)) to enhance expression of the therapeutic gene in a temporally and spatially controlled manner, these approaches have limited applicability die to residual background expression and inaccessibility of the heat of ionizing radiation to reach the target tissue.

Furthermore, controllable, tissue specific expression of transgenes is a primary goal in transgenic animals that serve as experimental models of disease. Early attempts at controlling transgene expression in transgenic mice have often employed transgenes that had been operably linked to tetracycline-responsive promoters or to rapamycin-responsive promoters.

The first tetracycline-controlled promoter was constructed by fusing the operator sequence of the *E. coli* tetracycline-resistance gene (tetO) to the minimal promoter sequence of the human cytomegalovirus immediate-early gene (hCMV IE), (Gossen, M. and Bujard, H., Tight control of gene expression in mammalian cells by tetracycline-responsive promoters. Proc. NatL Acad Sci. USA 89(12), 5547-5551, 1992.) A promoter such as a tetO/hCMV is activated when it binds to a fusion protein constructed from the tetracycline-controlled transactivator (tTA), which contains a tetO binding protein tetracycline repressor (tetR), plus a transcription activator, virion protein 16 (VP 16), from herpes simplex virus. In the absence of tetracycline, this fusion protein binds to the tetO/hCMV promoter and activates transcription of the exogene. In the presence of tetracycline, exogene transcription is blocked because tetracycline binds to the transactivator (tTA) and interferes with its binding to the tetO/hCMV promoter. Since tetracycline down-regulates transgene expression, this is called the "tet-Off" promoter system. However, the tet-Off promoter system is associated with leaky gene expression which complicates the use of this system for basic research or pharmaceutical application. Furth and colleagues first used the tet-Off tetracycline-controlled promoter in transgenic mice that expressed the reporter transgene, luciferase, under control of the tetO/hCMV promoter. When tetracycline was absent, luciferase expression was observed in numerous tissues. When tetracycline was provided subcutaneously, the luciferase activity was significantly reduced to low, but still detectable, background levels, thus inducing "leakiness" of the tet-off promoter.

This leaky transgene expression was observed with two different plasmid delivery systems, the paired plasmid system of Furth (Furth, P. A., St. Onge, L., Boger, H., Gruss, P., Gossen, M., Kistner, A., Bujard, H., and Henninghausen, L., Temporal control of gene expression in transgenic mice by tetracycline responsive promoter. Proc. Natl. Acad Sci. USA 91(20), 9302-9306, 199) and the combined system of Nathalis (Schultze, N., Burki, Y., Lang, Y., Certa, U., and Bluethmann, H., Efficient control of gene expression by single step integration of the tetracycline system in transgenic mice. Nature Biotechnology 14(4), 499-503, 1996.).

Similarly, leaky transgene expression has also been observed in transgenic models that utilized the tet-Off system linked to a tissue specific promoter, the cardiac-specific, α-myosin heavy chain promoter (α-mhc) (Yu, Z., Redfern, C. S., and Fishman, G. I., Conditional transgene expression in the heart. Circ. Res. 79(4), 691-697, 1998). In these studies, the leaky transgene expression was observed in various tissues, such as kidney, skeletal muscle, pancreas, and live. Even stronger leaky gene expression was observed in cardiac tissues.

The tetO/hCMV genetic system has also been modified to allow tetracycline to induce, rather then inhibit, transgene expression. Such a modified system employs the reverse tetracycline-controlled transactivator (rtTA), comprised of a mutated tetO binding protein, rtetR (tetracycline repressor, rtTA) linked to VP16 (Gossen, M., Freundlieb, S., Bender, G., Muller, G., Hillen, W., and Bujard, H., Transcriptional activation by tetracyclines in mammalian cells. Science 268(5218), 1766-1769, 1995). When tetracycline is absent, the rtTA cannot bind to the tetO in the tetracycline-controlled promoter. When tetracycline is present, it binds to the rtTA which allows the rtTA to bind to the tetO in the promoter and up-regulate transcription of the exogene. Since tetracycline induces gene expression, this is called the "tet-On" promoter system.

While leaky gene expression is less prevalent in transgenic mice in which the transgene is under control of the tet-On promoter as compared to the mice in which the transgene is under control of the tet-Off promoter. However, use of the tet-On promoter is not able to eliminate residual leaky gene expression. In addition, transgenic mice whose transgenes are responsive to rapamycin have also been shown to express detectable background levels of transgene transcription in the absence of rapamycin. Such "leaky" transgene transcription seriously compromises studies with these transgenic mice.

Accordingly, it is desirable to have new methods and systems for producing transgenic animals, particularly transgenic mice, which have little to no background transgene transcription, particularly in specific tissues.

In a similar approach to the tet system, ionizing radiation has been used to activate a radiosensitive promoter, e.g. the EGR-1 promoter (Weischelbaum et al. (1994) Cancer Res 54:4266-4269; Hallahan et al. (1995) Nat Med 1(8):786-791; Joki et al. (1995) Hum Gen Ther 6:1507-1513). Another alternative design relies on endogenous control of gene expression. For example, the CEA promoter is selectively expressed in cancer cells (Hauck & Stanners (1995) J Biol Chem 270:3602; Richards et al. (1995) Human Gene Ther 6:881-893).

In the past, several approaches have been attempted to solve leakiness problem in plant gene expression without much success. By conducting a series of deletion of promoter sequence, one might eliminate the sequence in the promoter region which contributes to the leaky expression. For example, a deleted version of TbRB7 promoter drives GUS reporter gene expression in nematode feeding cells in the root upon nematode infection. Leaky expression, however, in flower tissue is still unsolved (Opperman C H et al., Science 263:221-223, (1994)). By making a chimeric promoter, i.e. a minimal promoter (e.g. 35S promoter) plus tissues-specific regulatory elements, one might restrict gene expression in desired tissues. However, if tissue-specific regulatory elements are leaky, the chimeric promoter will be leaky as well.

Several other methods to control leakiness of transgene expression have been explored, although each has their limitations. For example, U.S. patent application No: 2003/0045495 disclosed a modified inducible systems for selective expression of therapeutic genes by hyperthermia, although its utility is limited as hypothermia is also difficult to be applied to discrete cells or small tissue areas. Similarly, U.S. patent application No: 2001/0049828 discloses a method and system for controlling the expression of transgene products in specific tissues in a transgenic animal, which is based on an interaction of various transactivators in a transgenic mouse system. The transgene expression is controlled by antisense which is under control of the transactivator and tissue-specific promoters, thereby suppressing expression in certain tissues. However, this system is severely limited by its requirement of the antisense gene to be targeted to an endogenous gene sequence, for example the antisense targets the transgene being expressed and this could lead to non-specific effects if the antisense target gene is expressed endogenously in the cell, or in circumstances where the target gene is a member of a gene family also expressed in the cell. Accordingly, the use of this system is limited by being highly complicated and relying on several expression constructs and transgenic transcription factors. Similarly, U.S. patent application No:2002/0065243 discloses a system whereby an antisense to a tet repressor is expressed under the control of a constitutive promoter. Another system as disclosed in U.S. patent application No: US2002/0022018 describes tissue-specific deletion or destruction of the expression by tissue-specific expression of a Cre recombinase. As a result of Cre recombinase expression, the transgene floxed by LoxP sites in that tissue will be cut by the action of the Cre recombinase. Consequently, unwanted transgene as well as viral gene expression are prevented. However, due to leakiness of the promoter driving Cre expression, expression is expected to be lowered also in the target tissue itself, thereby decreasing overall efficiency of this approach.

Gene transfer involves the transfer of foreign genetic material into a cell such that the foreign material or transgene is expressed. This process is used in applications such as, for example: gene therapy, production of recombinant biologicals, genetic diagnosis, and drug screening. But despite recent reports of success in the most challenging of these fields, in vivo gene therapy of human diseases (Kay et al., 2000; Cavazzano-Calvo et al., 2000), the construction of new expression vectors has occupied the attention of the many workers eager to achieve high levels of gene expression in a regulated manner (reviewed in Agha-Mohammadi and Lotze, 2000).

In most cases, the ultimate goal of gene transfer is to introduce an expression vector that provides for production of a gene product for a period sufficient for a therapeutic or prophylactic effect, which period may be relatively short (e.g., a few hours to a few days) or may be for long periods (e.g., several weeks to one or more years). One important aspect of gene-based therapy could involve regulating expression in such a manner that gene expression is restricted spatially and temporally to cells or tissues that are affected by a disease. Such regulation requires that the gene be delivered to the target cell or tissue in a substantially latent state, so that it does not change or significantly affect the phenotype of the target in the absence of disease. Where and when the disease is active, it would be desirable that the latent gene should then be induced (e.g., spatially, temporally, or both) in a manner that will counteract disease symptoms and, conversely, ceases expression as the disease symptoms subside. To simplify, this requires that the gene be regulated by a tight on/off switch that can respond to a stimuli to switch the expression of the gene on/off.

A critical feature of such regulated gene expression is called the silencer-inducer ratio: expression of the transgene measured under inducing conditions divided by the amount of expression without induction (i.e., basal expression). Basal expression is a level of gene expression under non-inducing conditions and is a measure of the promoters "leakiness". This ratio should be high (e.g., at least about 25- to 1,000-fold) and sufficiently regulatable by appropriate control of inducing conditions. Another critical feature is substantially silenced (or repressed) gene expression in the non-induced state.

This requirement for a tight on-off switch in regulating expression of a transgene is widely acknowledged and the absence of such regulation is considered to be one of the major limitations for many gene transfer applications. Regulated expression of transgenes, both positive and negative, has been described in prokaryotes (e.g., the Lac operon) and in mammals (e.g., Tetrepressor and activator, progesterone or ecdysone receptor) (reviewed in Agha-Mohammadi and Lotze, 2000). Each of these systems involves binding of an extrinsic modulator to a protein involved in transcription: tetracycline or doxycycline in the Tet regulatory system; RU486 or rapamycin in the progesterone and FKBP regulatory systems, respectively. The latter two systems require multiple vectors to deliver the target gene and the different regulatory components. In all of these systems, allosteric changes determine the DNA binding affinities of positive- and negative-acting transcriptional factors and thereby control an on-off switch (Freundlieb et al., 1999). However, these systems are all limited due to levels of "leakiness" of the promoters. 1251 Accordingly, there remains substantial need for improvement of methods and systems for inducing gene expression in a highly controllable manner, while maintaining control of promoter leakiness to ensure no background transgene expression, particularly for therapeutic uses and gene expression in specific tissues.

SUMMARY OF THE INVENTION

The present invention relates to methods, compositions and systems for controlling the inducible expression of transgenes, in particular expression in specific tissues and in transgenic animals, such as for example a transgenic mouse, while eliminating background expression of the transgene products. The present invention relates to a tight on/off switch in regulating gene expression with minimal or no leakiness of transgene expression in the off state.

The inventors have discovered a method and system for a tightly controlled highly inducible gene expression system. For example, the inventors have discovered a method to eliminate or significantly reduce the leakiness of transgene expression from an inducible gene expression system n the non-induced state. In some embodiments, the inventors have discovered methods to minimize background transgene expression from a promoter, where background expression is limited to less than 5%, to less than 3%, preferably to less than 2%, and preferably to less than 1%, and less than 0.5%, less than 0.1% and even more preferably where background transgene is completely eliminated in the non-induced state.

In some embodiments of the present invention, the methods and systems as disclosed herein relate to a nucleic acid encoding the RNAi agent which targets a non-endogenous RNAi target site, e.g. a synthetic RNAi target site, located within the non-coding region of the heterologous target gene. In some embodiments, the expression of the RNAi agent is controlled by a repressible promoter, such as, for example but not limited to a repressible promoter regulated by a Tet repressor (Tet$^R$) protein. In some embodiments, the nucleic acid encoding the first repressor protein is controlled by a second repressor promoter, such as for example but not limited to a LacO promoter. In alternative embodiments, the first repressor protein is controlled by an inducible promoter. In some embodiments, second repressor promoter or inducible promoter also controls the expression of the heterologous target gene.

In one embodiment, the RNAi agent is operatively linked to a repressor promoter such as the TetO promoter, and the expression of the Tet repressor protein (TetR) is operatively linked to a second repressor promoter, the LacO promoter. In some embodiments, the expression of the Lac repressor protein (LacI) is operatively linked to a promoter, such as a tissue specific promoter or a constitutive promoter. In such embodiments, the expression of LacI will repress expression of nucleic acids operatively linked to the LacO promoter, and thus expression of LacI will repress expression of the Tet$^R$ protein. In such embodiments, lack of Tet$^R$ will result in expression of proteins operatively linked to the TetO promoter, thus resulting in the expression of the RNAi agent and gene silencing of the heterologous target gene. In some embodiments, the nucleic acid of the heterologous target gene is also operatively linked to the LacO promoter.

In further embodiments, LacI can be inhibited or inactivated by externally applied agents, such as, for example IPTG or derivatives or analogues thereof. In such embodiments, inhibition of LacI by IPTG results in expression from genes operatively linked to the LacO promoter, thus resulting in expression of the heterologous target gene, and the expression of, for example, the Tet$^R$, where the Tet$^R$ then represses gene expression from the TetO promoter to inhibit the expression of the RNAi agent and prevent gene silencing of the heterologous target gene. In alternative embodiments, the absence of an externally applied agents such as IPTG, will result in active LacI and repression of genes operatively linked to the LacO promoter, resulting in repression of heterologous target gene expression and Tet$^R$ expression. Repression of Tet$^R$ allows expression from genes operatively linked to the TetO, such as RNAi expression which can function to gene silence any background expression of the heterologous target gene.

In alternative embodiments, the nucleic acid encoding the repressible protein to the repressible promoter (which is operatively linked and controls the expression of the RNAi agent) is operatively linked to an inducible promoter. In such embodiments, an externally applied agent to the inducible promoter activates the expression of the encoded repressor protein, which in turn represses expression from the repressor promoter to downregulate the encoded RNAi. In some embodiments, the heterologous gene target and the nucleic acid encoding the repressor protein are both operatively linked to the inducible promoter. In such embodiments, the externally applied agent induces the expression of the heterologous gene target and the repressor protein which down regulates the expression of the RNAi to attenuate RNAi mediated gene silencing of the heterologous gene target.

One aspect of the present invention relates to a system for the expression of a heterologous target gene in a mammalian cell, the system comprising a nucleic acid sequence encoding an RNA interference molecule (RNAi) agent and a nucleic acid RNAi target sequence, wherein the RNAi target sequence is not endogenous to the cell and is located within the non-coding region of the nucleic acid sequence encoding a heterologous gene, wherein the nucleotide sequence encoding the heterologous target gene is operatively linked to a first repressor promoter or operator sequence, wherein the nucleotide sequence encoding the RNAi agent is operatively linked to a second repressor promoter sequence, wherein the second repressor promoter sequence is controlled by a second repressor molecule, wherein the nucleic acid sequence encoding the second repressor molecule is operatively linked to a second promoter and a first repressor promoter sequence, wherein the first repressor promoter or operator sequence is controlled by a first repressor molecule, wherein the nucleic acid sequence encoding the first repressor molecule is operatively linked to a first promoter, wherein the first repressor molecule is inhibited by a small molecule; and wherein the presence of the small molecule relieves repression of the first repressor promoter sequence thereby expression of the heterologous gene and induced expression of the second repressor molecule represses the expression of the RNAi agent, thereby permitting expression of the heterologous target gene.

Another aspect of the present invention relates to a continuous or non-continuous nucleic acid construct comprising; (i) a nucleotide sequence encoding a heterologous target gene wherein the heterologous target gene is operatively linked to a first repressor promoter sequence; (ii) a nucleic acid sequence encoding an RNA interference (RNAi) agent wherein the nucleotide sequence encoding the RNAi agent is operatively linked to a second repressor promoter sequence, (iii) a nucleic acid RNAi target sequence which is a non-endogenous target sequence, and is recognized by the RNAi agent, wherein the RNAi target sequence is located in a non-coding region of the nucleic acid sequence encoding a heterologous target gene, (iv) a second repressor sequence wherein the second repressor promoter sequence is controlled by a second repressor molecule, (v) a nucleic acid sequence encoding the second repressor molecule which is operatively linked to a second promoter and a first repressor promoter sequence, (vi) a first repressor promoter sequence which is controlled by a first repressor molecule, and (v) a nucleic acid sequence encoding the first repressor molecule which is operatively linked to a first promoter, wherein the first repressor molecule is inhibited by a small molecule.

In some embodiments, an RNAi agent is an antisense polynucleotide, shRNA, miRNA, siRNA, stRNA, ribozyme or double stranded RNA (dsRNA) or derivatives thereof.

In another embodiment, the non-coding region relates to the 3'UTR, 5'UTR or intron sequence of the heterologous target gene.

In some embodiments, the first repressor promoter sequence is a Lac operator sequence (LacO) and the first repressor molecule is Lac Repressor (LacI). In some embodiments, the second repressor promoter sequence is a Tet operator sequence (TetO) and the second repressor molecule is Tet Repressor (TerR). In some embodiments, the small molecule is IPTG or an analogue, derivative or variant thereof.

In some embodiments, a first promoter and/or second promoters are constitutive promoters or fragments or derivatives thereof. In alternative embodiments, a first promoter and/or second promoters are tissue-specific or cell-specific promoters, or fragments or derivatives thereof.

In some embodiments, a first repressor molecule is LacI, or a variant or fragment thereof. In some embodiments, a first repressor promoter sequence comprises at least one LacO site, or a variants or fragments thereof. In some embodiments, a small molecule is IPTG or a derivative or analogue thereof.

In some embodiments, a second repressor molecule is TetR, or a variant or fragment thereof. In some embodiments, the first repressor promoter sequence comprises at least one tet operator site (TetO) or a variant or fragment thereof.

In some embodiments, a RNA interference (RNAi) agent useful in the methods as disclosed herein includes, for example but is not limited to antisense nucleotide acid, oligonucleotide, siRNA, shRNA, mRNA, ribozyme, avimirs or variants or derivatives thereof. In some embodiments, a RNAi agent is a shRNA molecule.

In some embodiments, a RNA interference (RNAi) agent useful in the methods as disclosed herein is substantially complementary to a non-endogenous nucleotide sequence, for example a fragment of a bacterial gene such as E. coli β-galactosidase sequence, luciferase gene or viral sequence, where such nucleotide sequences are not normally found in the cell in which the heterologous target gene is to be expressed. For example, in some embodiments, the RNAi agent is substantially complementary to SEQ ID NO:1 or SEQ ID NO:2 or a variant or homologue thereof.

In some embodiments, a heterologous target gene is a marker gene or a fragment thereof. Alternatively, in some embodiments, the nucleic acids and systems as disclosed herein further comprises a marker gene or a fragment thereof operatively linked to the first repressor promoter sequence. In some embodiments, a heterologous target gene can be any gene, including for example but not limited to, cre recombinase (Cre), pro-apoptotic genes, cytotoxin molecules, immunotoxin molecules and fragment or derivative thereof. In some embodiments, a cytotoxic molecule can be, for example but not limited to plant halotoxins, plant hemitoxins, bacterial toxins, antrax toxins, diptherial toxins (DT), pseudomonal endotoxins, sterptolysin O, saporin (SAP), pokeweek antiviral protein (PAP), bryodin 1, bouganin and gelonin and fragments or variants thereof. In some embodiments, a heterologous target gene is a molecule that sensitizes the cell to one or more secondary agents, for example heterologous gene that sensitizes the cell to one or more secondary agents such as, for example; β-glutonidase, hypoxanethine-guiane phosphoribosynitransferas, β-lactamase, caroxblesterase HCE1, peroxidase enxyme. In some embodiments, a heterologous target gene is an anti-apoptotic gene, or a fragment or variant thereof.

In some embodiments, the nucleotide construct or system as disclosed herein can optionally further comprises a nucleotide sequence encoding at least one marker gene which is operatively linked to the expression of the heterologous target gene wherein gene expression of the marker gene identifies cells also expressing the target gene. In some embodiments, the nucleotide construct optionally further comprises a nucleotide sequence encoding at least one marker gene, wherein the expression of the marker gene is operatively linked to the first repressor promoter sequence, wherein gene expression of the marker gene identifies cells also expressing the target gene. In some embodiments, the nucleotide construct or system as disclosed herein can optionally further comprises at least one nucleotide sequence selected from the group of; internal ribosome target site (IBES) and/or multiple cloning nucleotide sequence site.

In some embodiments, the nucleotide construct or system as disclosed herein can optionally further comprise a promoter, for example but not limited to, enhancers, 5' untranslated regions (5'UTR), 3' untranslated regions (3'UTR), and repressor sequences; constitutive promoters, inducible promoter; tissue specific promoter, cell-specific promoter or variants thereof. Examples of tissue-specific promoters which can be used as first or second promoter include, but are not limited to, albumin, lymphoid specific promoters, T-cell promoters, neurofilament promoter, pancreas specific promoters, milk whey promoter; hox promoters, α-fetoprotein promoter, human LIMK2 gene promoters, FAB promoter, insulin gene promoter, transphyretin, alpha.1-antitrypsin, plasminogen activator inhibitor type 1 (PAI-1), apolipoprotein myelin basic protein (MBP) gene, GFAP promoter, OPSIN promoter, NSE, Her2, erb2, and fragments and derivatives thereof. Examples of other promoters which can be used as first or second promoter include, but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and variants thereof.

Another aspect of the present invention relates to a cell comprising continuous or non-continuous nucleic acid construct comprising (i) a nucleotide sequence encoding a heterologous target gene wherein the heterologous target gene is operatively linked to a first repressor promoter sequence; (ii) a nucleic acid sequence encoding an RNA interference (RNAi) agent wherein the nucleotide sequence encoding the RNAi agent is operatively linked to a second repressor promoter sequence, (iii) a nucleic acid RNAi target sequence which is a non-endogenous target sequence, and is recognized by the RNAi agent, wherein the RNAi target sequence is located in a non-coding region of the nucleic acid sequence encoding a heterologous target gene, (iv) a second repressor sequence wherein the second repressor promoter sequence is controlled by a second repressor molecule, (v) a nucleic acid sequence encoding the second repressor molecule which is operatively linked to a second promoter and a first repressor promoter sequence, (vi) a first repressor promoter sequence which is controlled by a first repressor molecule, and (v) a nucleic acid sequence encoding the first repressor molecule which is operatively linked to a first promoter, wherein the first repressor molecule is inhibited by a small molecule. In some embodiments, the cell is a mammalian cell, for example a human cell. In some embodiments, the cell is in vitro, or in vivo or in some embodiments, the cell is ex vivo. In some embodiments, the cell is present in a transgenic animal, for example a transgenic mouse.

Another aspect of the present invention relates to a transgenic animal model comprising a continuous or non-continuous nucleic acid construct comprising (i) a nucleotide sequence encoding a heterologous target gene wherein the heterologous target gene is operatively linked to a first repressor promoter sequence; (ii) a nucleic acid sequence encoding an RNA interference (RNAi) agent wherein the nucleotide sequence encoding the RNAi agent is operatively linked to a second repressor promoter sequence, (iii) a nucleic acid RNAi target sequence which is a non-endogenous target sequence, and is recognized by the RNAi agent, wherein the RNAi target sequence is located in a non-coding region of the nucleic acid sequence encoding a heterologous target gene, (iv) a second repressor sequence wherein the second repressor promoter sequence is controlled by a second repressor molecule, (v) a nucleic acid sequence encoding the second repressor molecule which is operatively linked to a second promoter and a first repressor promoter sequence, (vi) a first repressor promoter sequence which is controlled by a first repressor molecule, and (v) a nucleic acid sequence encoding the first repressor molecule which is operatively linked to a first promoter, wherein the first repressor molecule is inhibited by a small molecule. In some embodiments, the transgenic animal model comprises a heterologous target gene encoding Cre recombinase or a variant of fragment thereof.

Another aspect of the present invention relates to a method to treat or prevent a disease in a subject, the method comprising administering to a subject an effective amount of a cell comprising the nucleic acid construct as disclosed herein.

In alternative embodiments, the present invention relates to a method to treat or prevent a disease in a subject, the method comprising administering to a subject an effective amount of a nucleic acid construct comprising (i) a nucleotide sequence encoding a heterologous target gene wherein the heterologous target gene is operatively linked to a first repressor promoter sequence; (ii) a nucleic acid sequence encoding an RNA interference (RNAi) agent wherein the nucleotide sequence encoding the RNAi agent is operatively linked to a second repressor promoter sequence, (iii) a nucleic acid RNAi target sequence which is a non-endogenous target sequence, and is recognized by the RNAi agent, wherein the RNAi target sequence is located in a non-coding region of the nucleic acid sequence encoding a heterologous target gene, (iv) a second repressor sequence wherein the second repressor promoter sequence is controlled by a second repressor molecule, (v) a nucleic acid sequence encoding the second repressor molecule which is operatively linked to a second promoter and a first repressor promoter sequence, (vi) a first repressor promoter sequence which is controlled by a first repressor molecule, and (v) a nucleic acid sequence encoding the first repressor molecule which is operatively linked to a first promoter, wherein the first repressor molecule is inhibited by a small molecule.

Another aspect of the present invention relates to a method to identify a threshold of the level of gene expression of a heterologous target gene to regulate a biological process in a cell, the method comprising expressing the heterologous target gene in the cell using the system or nucleic acid of any of the claims 1 to 33, and contacting the cell with an effective amount of an inducer agent, whereby the level of heterologous target gene expression that induces or inhibits a biological process is the threshold level of gene expression of the heterologous target gene to regulate a biological process.

Another aspect of the present invention relates to a method and system wherein a nucleic acid encoding the RNAi agent which targets a RNAi target site located within a non-coding region of the heterologous target gene, where the expression of the RNAi is controlled by a repressible promoter, such as, for example but not limited to a repressible promoter such as LacO, which regulated by a LacI repressor protein. In some embodiments, the nucleic acid encoding the repressor protein, such as LacI is operatively linked to a constitutive promoter or a tissue-specific promoter. In such embodiments, in a non-induced state, expression of the LacI repressor binds to the LacO repressor promoter inhibiting the expression of the operatively linked RNAi agent. Thus, in a normal state the expression of the RNAi agent is in the "off" state and does not gene silence the heterologous target gene, and by addition of externally applied agents, such as IPTG, results in the inhibition or inactivation of LacI and subsequently allows expression of genes operatively linked to the LacO promoter such as the expression of the RNAi agent. Accordingly, such embodiments are useful in tight control of inducible gene expression where it is desirable to switch off a constitutively expressed heterologous target gene.

In some embodiments, the heterologous target gene is also negatively regulated to the LacO promoter, meaning that in the presence of LacI, the expression of the heterologous target gene occurs, whereas when LacI is inactivated or inhibited, the expression of the heterologous target gene does not occur.

BRIEF DESCRIPTION OF FIGURES

FIG. 1 shows a schematic diagrams of the synthetic gene network. Panel 1A shows a schematic of the uninduced state (LTRi-EGFP genetic switch in the off state), LacI repressor proteins are constitutively expressed and bind to the lac operator (lacO) sites in the transgene module. This causes transcriptional repression of EGFP. The LacI repressor proteins also bind to the lac operator sites in the TetR repressor module, which causes transcriptional repression of TetR. With the repression of TetR, shRNA is transcribed by the U6 promoter and complementarily binds to the synthetic target sequence located in the 3' UTR of the EGFP mRNA. Any EGFP leakage of the transcript is targeted by the RNAi module, resulting in undetectable EGFP expression. Panel 1B shows a schematic of the induced state (LTRi-EGFP genetic switch in the on state), isopropyl-β-thiogalactopyranoside (IPTG) binds to the LacI proteins and produces a conformational change in the repressor proteins. This causes them to no longer bind to the lac operator sites, which allows for the transcription of EGFP and TetR. The Tet repressor proteins bind to the tet operator site located in the U6 promoter of the RNAi module, which represses the transcription of the shRNA. The resulting effect is robust expression of EGFP.

FIG. 5 shows the use of the Genetic Switch to Tightly Control Cre Expression. Panel 5A shows a schematic diagram of LTRi-cre. Rosa26 cells were transiently transfected with LTRi-cre. Panel 5B (left) shows a schematic diagram of LTRi-cre in the off state. Panel 5B (right), shows a bright-field microscope image of cells with LTRi-cre in the off state. Panel 5C (left), shows a schematic diagram of LTRi-cre in the on state. Panel 5C (right), shows a bright-field microscope image of cells with LTRi-cre in the on state.

DETAILED DESCRIPTION OF THE INVENTION

Figure 2A:
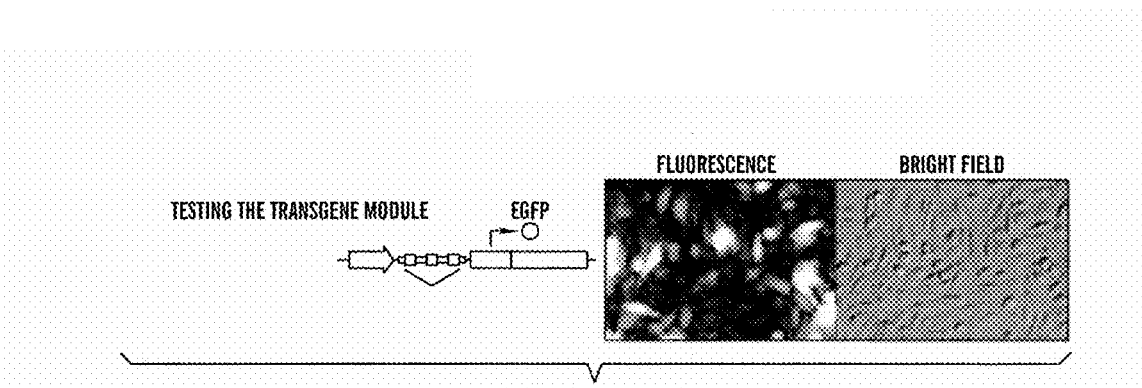
FIG. 2 shows the construction and Testing the Genetic Switch in a Modular Fashion. In panels 2A to 2D, the first column includes a schematic diagram of the tested module, while the second and third columns include fluorescence and bright-field microscope images, respectively, of cells containing the tested module. Panel 2A shows the transgene module served as our positive control (corresponding to maximum EGFP expression). Panel 2B, the RNAi module was added to the transgene module to characterize its functionality. Microscope images show that RNAI alone is incapable of suppressing EGFP expression to undetectable levels. Panel 2C shows the LacI repressor module was added to the transgene module to characterize its functionality. Microscope images show that transcriptional repression alone is incapable of suppressing EGFP expression to undetectable levels. Panel 2D shows the /ac/ repressor and RNAi modules were added together to the transgene module to characterize their combined functionality. Microscope images show that there is effectively no EGFP expression when the transcriptional and posttranscriptional mechanisms are coupled together. Panel 2E shows quantification of the expression of EGFP, we repeated the experiments described in 2A to 2D using flow cytometry. All EGFP expression levels were normalized to the maximum EGFP expression level. Each bar represents the mean EGFP expression in eight independent experiments. In this and all other figures, error bars represent standard deviations.

As disclosed herein, the inventors have discovered methods and systems for tight controlled, inducible expression of a heterologous gene. As disclosed herein, the inventors have generated a system comprising a nucleic acid encoding the RNAi agent which targets a RNAi target site located within the non-coding region of the heterologous target gene, thereby reducing background expression of the heterologous target gene even when the heterologous target gene is operatively linked to a leaky promoter.

Use of the current inducible gene expression systems, for example such as the Tet-on or Tet-off system are limited due to leakiness of transgene expression, and use of other gene expression systems using tissue-specific promoters to direct transgene expression are also limited due to leakiness of transgene expression. Promoter leakiness typically results in at least 10% undesired gene expression. In general, undesired gene expression from leaky promoters may vary from 10% to about 30%. Undesired transgene expression (even as little as 20% or 10% of gene expression) due to promoter leakiness can lead to undesirable phenotype and significantly minimizes the use of such promoters for a variety of applications, such as for example but not limited to, therapeutic use.

To address this problem, the inventors have developed within the context of synthetic biology a tunable mammalian genetic switch. The inventors have discovered a method to essentially eliminate "leakiness" of transgene expression in an inducible gene expression system by developing a synthetic gene network, also referred to herein as a "switch" that couples repressor proteins with an RNAi design involving shRNA which is sometimes referred to herein as "LTRi" which stands for Lac-Tet-RNAi. In some embodiments of the present invention, gene expression is turned on by adding an inducer agent, such as isopropyl-β-thiogalactopyranoside (IPTG), which controls the repressor elements at the transcriptional level, while simultaneously turning off the RNAi component to allow the transgene transcript to be retained and translated. Furthermore, the inventors have discovered the system is modular in nature, allowing for the regulation of any gene, including heterologous and other recombinant genes.

An essential, inventive feature of the present invention as disclosed herein relates to the incorporation of an "RNAi agent" which targets a RNAi target site located within the non-coding region of transgene to be expressed, for example a heterologous target gene, where the RNAi agent gene silences any expression of the transgene, to eliminate expression even in instances when the inducible or tissue-specific promoter is "leaky." One can control this system by how the RNAi is operatively linked to the system. For example, the RNAi agent can, in the absence of an inducer be in the "on" position, thus gene silencing the heterologous target gene in a non-induced state. Conversely, the RNAi agent can be normally be in the "off" position, thereby silencing the expression of a heterologous target gene only in the induced state.

In one embodiment of the present invention, the expression of the RNAi agent is negatively regulated by the inducer agent, i.e. when the inducer agent is present, the expression of the "RNAi agent" is switched off, thereby enabling transgene expression. Accordingly, the inventors have discovered a method and system for tightly controlled highly inducible gene expression system. For example, the inventors have discovered a methods to reduce the leakiness of transgene expression from an inducible gene expression system. In some embodiments, the inventors have discovered methods to minimize background transgene expression from a promoter, where background expression is limited to less than 5%, to less than 3%, preferably to less than 2%, and preferably to less than 1%, less than 0.5%, less than 0.1% and even more preferably where background transgene is completely eliminated.

The inventors have demonstrated a system of inducible gene expression with no background transgene expression by using the LTRi genetic switch as disclosed herein to regulate EGFP (LTRi-EGFP) in Chinese hamster ovary (CHO) cells and human embryonic kidney 293 (HEK293) cells. The inventors have discovered that the system offers >99% repression of the transgene expression in the "off" state (i.e. in the absence of the inducer agent) as compared to other inducible gene expression systems or positive controls.

In addition to sustaining a tight off state, (i.e. no expression for leakiness of the promoter), the inventors demonstrate that LTRi allows for tunable, reversible control of gene expression. The inventors used LTRi to control the expression of the highly toxic a chain of diphtheria toxin, DTA (LTRi-DTA) in order to demonstrate the system's modularity and level of gene silencing. The inventors demonstrated that cells with LTRi-DTA in the off state survive despite the presence of the DTA gene, and the cells can be triggered to die following induction with the induced agent, such as IPTG.

To demonstrate the potential for other in vivo experimental applications, the inventors demonstrate the LTRi switch can be used to control the expression of Cre recombinase (LTRi-cre) in Rosa26 primary mouse cells. Similar to the LTRi-DTA results, the inventors demonstrate that cells with LTRi-cre in the off state exhibit no expression of the cre transgene, and genetic recombination is observed only following induction of the switch with the inducer agent, IPTG.

To demonstrate that LTRi is capable of regulating a biological process, the inventors placed bax, a proapoptotic gene, under the control of LTRi (LTRi bax). Bax is a member of the Bcl-2 family of proteins that has been associated with apoptotic death both in cell culture and in intact animals (Aneja et al., 2006; Pastorino et al., 1998; Shinoura et al., 1999). The overexpression of Bax has been shown to cause apoptosis by disrupting the mitochondrial transmembrane potential and releasing cytochrome c from the mitochondria (Katiyar et al., 2005; van Engeland et al., 1998). By tuning the level of Bax in primary mouse cells, the inventors have discovered this system can be used to determine a threshold level of Bax which is required to induce apoptosis.

Accordingly, the inventors discovery as disclosed herein establishes a system for tight, tunable, reversible control of mammalian gene expression which has a variety of uses, including but not limited to, use of the LTRi system to explore the functional role of developmental genes and mechanisms of biological switches, as well as in assays to identify the threshold responses to changes in gene expression, and for therapeutic utility for a tight, tunable, reversible control of mammalian gene expression in gene therapy, for example but not limited to the expression of genes for cancer therapeutics etc.

In some embodiments, the expression of the RNAi agent is controlled by a repressible promoter, such as, for example but not limited to a repressible promoter regulated by a Tet repressor (Tet$^R$) protein. In some embodiments, the nucleic acid encoding the first repressor protein is controlled by a second repressor promoter, such as for example but not limited to a LacO promoter. In alternative embodiments, the first repressor protein is controlled by an inducible promoter. In some embodiments, second repressor promoter or inducible promoter also controls the expression of the heterologous target gene.

In one embodiment, the RNAi agent is operatively linked to a repressor promoter such as the TetO promoter, and the expression of the Tet repressor protein (TetR) is operatively linked to a second repressor promoter, the LacO promoter. In some embodiments, the expression of the Lac repressor protein (LacI) is operatively linked to a promoter, such as a tissue specific promoter or a constitutive promoter. In such embodiments, the expression of LacI will repress expression of nucleic acids operatively linked to the LacO promoter, and thus expression of LacI will repress expression of the Tet$^R$ protein. In such embodiments, lack of Tet$^R$ will result in expression of proteins from the TetO promoter, thus expression of the RNAi and gene silencing of the heterologous target gene. In some embodiments, the nucleic acid of the heterologous target gene is also operatively linked to the LacO promoter.

In further embodiments, LacI can be inhibited or inactivated by externally applied agents, such as, for example IPTG or derivatives or analogues thereof. In such embodiments, inhibition of LacI by IPTG results in expression from the LacO promoter, resulting in expression of the heterologous target gene and expression of the Tet$^R$, where the Tet$^R$ represses gene expression from the TetO promoter and inhibits the expression of the RNAi agent and prevents gene silencing of the heterologous target gene. In alternative embodiments, the absence of an externally applied agents such as IPTG, will result in active LacI and repression of genes operatively linked to the LacO promoter, resulting in repression of heterologous target gene expression and Tet$^R$ expression. Repression of Tet$^R$ allows expression from genes operatively linked to the TetO, such as RNAi expression which can function to gene silence any background expression of the heterologous target gene.

DEFINITIONS

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof.

The term "alter" or "modulate" are used interchangeably herein refers to the expression of a nucleotide sequence in a cell means that the level of expression of the nucleotide sequence in a cell after applying a method of the present invention is different from its expression in the cell before applying the method.

As used herein, "gene silencing" or "gene silenced" in reference to an activity of a RNAi molecule, for example a siRNA or miRNA refers to a decrease in the mRNA level in a cell for a heterologous target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%. As used herein, the "reduced" or "gene silencing" refers to lower, preferably significantly lower, more preferably the expression of the nucleotide sequence is not detectable.

As used herein, the term "RNAi" refers to any type of interfering RNA, including but are not limited to, siRNAi, shRNAi, stRNAi, endogenous microRNA and artificial microRNA. For instance, it includes sequences previously identified as siRNA, regardless of the mechanism of downstream processing of the RNA (i.e. although siRNAs are believed to have a specific method of in vivo processing resulting in the cleavage of mRNA, such sequences can be incorporated into the vectors in the context of the flanking sequences described herein). The term "siRNA" also refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 10-50 nucleotides in length (e.g., each complementary sequence of the double stranded siRNA is about 10-22 nucleotides in length, and the double stranded siRNA is about 10-22 base pairs in length, preferably about 19-22 base nucleotides, preferably about 17-19 nucleotides in length, e.g., 10, 11, 12, 13, 14, 15, 16, 17, 18, 19, 20, 21, or 22 nucleotides in length).

As used herein "shRNA" or "small hairpin RNA" (also called stem loop) is a type of siRNA. In one embodiment, these shRNAs are composed of a short, e.g. about 10 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

A "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and the term is used consistently with its known meaning in the art. The actual primary sequence of nucleotides within the stem-loop structure is not critical to the practice of the invention as long as the secondary structure is present. As is known in the art, the secondary structure does not require exact base-pairing. Thus, the stem may include one or more base mismatches. Alternatively, the base-pairing may be exact, i.e. not include any mismatches. In some instances the precursor microRNA molecule may include more than one stem-loop structure. The multiple stem-loop structures may be linked to one another through a linker, such as, for example, a nucleic acid linker or by a microRNA flanking sequence or other molecule or some combination thereof. The actual primary sequence of nucleotides within the stem-loop structure is not critical as long as the secondary structure is present. As is known in the art, the secondary structure does not require exact base-pairing. Thus, the stem may include one or more base mismatches. Alternatively, the base pairing may not include any mismatches.

As used herein the term "hairpin RNA" refers to any self-annealing double stranded RNA molecule. In its simplest representation, a hairpin RNA consists of a double stranded stem made up by the annealing RNA strands, connected by a single stranded RNA loop, and is also referred to as a "panhandle RNA". However, the term "hairpin RNA" is also intended to encompass more complicated secondary RNA structures comprising self-annealing double stranded RNA sequences, but also internal bulges and loops. The specific secondary structure adapted will be determined by the free energy of the RNA molecule, and can be predicted for different situations using appropriate software such as FOLDRNA (Zuker and Stiegler (1981) Nucleic Acids Res 9(1):133-48; Zuker, M. (1989) Methods Enzymol. 180, 262-288).

The term "agent" refers to any entity which is normally absent or not present at the levels being administered, in the cell. Agent may be selected from a group comprising; chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, "a reduction" of the level of a gene, included a decrease in the level of a protein or mRNA means in the cell or organism. As used herein, "at least a partial reduction" of the level of an agent (such as a RNA, mRNA, rRNA, tRNA expressed by the target gene and/or of the protein product encoded by it) means that the level is reduced at least 25%, preferably at least 50%, relative to a cell or organism lacking the RNAi agent as disclosed herein. As used herein, "a substantial reduction" of the level of an agent such as a protein or mRNA means that the level is reduced relative to a cell or organism lacking a chimeric RNA molecule of the invention capable of reducing the agent, where the reduction of the level of the agent is at least 75%, preferably at least 85%. The reduction can be determined by methods with which the skilled worker is familiar. Thus, the reduction of the transgene protein can be determined for example by an immunological detection of the protein. Moreover, biochemical techniques such as Northern hybridization, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) to detect transgene protein or mRNA. Depending on the type of the reduced transgene, its activity or the effect on the phenotype of the organism or the cell may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254).

As used herein, the term "amino acid sequence" refers to a list of abbreviations, letters, characters or words representing amino acid residues. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "antisense" as used herein refers to a nucleotide sequence that is inverted relative to its normal orientation for transcription and so it can hybridize to the target gene mRNA molecule through Watson-Crick base pairing. An antisense strand may be constructed in a number of different ways, provided that it is capable of interfering with the expression of a target gene. For example, the antisense strand can be constructed by inverting the coding region (or a portion thereof) of the target gene relative to its normal orientation for transcription to allow the transcription of its complement, (e.g., RNAs encoded by the antisense and sense gene may be complementary). Furthermore, the antisense oligonucleotide strand need not have the same intron or exon pattern as the target gene, and noncoding segments of the target gene may be equally effective in achieving antisense suppression of target gene expression as coding segments. In the context of gene silencing the term "antisense" is understood to mean a nucleic acid having a sequence complementary to a target sequence, for example a messenger RNA (mRNA) sequence the blocking of whose expression is sought to be initiated by hybridization with the target sequence.

The term "gene" as used herein refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine and on the 3'-side by one of the three triplets which specify stop codons (i.e., TAA, TAG, TGA). In addition to containing introns, genomic forms of a gene may also include sequences located on both the 5'- and 3'-end of the sequences which are present on the RNA transcript, which are termed "5' untranslated regions" or 5'UTR and 3' untranslated regions (3'UTR) respectively. These sequences are also referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

The term "complementary" or "complementarity" as used herein refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. A "complement" of a nucleic acid sequence as used herein refers to a nucleotide sequence whose nucleic acids show total complementarity to the nucleic acids of the nucleic acid sequence.

The term "double-stranded RNA" molecule, "RNAi molecule", or "dsRNA" molecule as used herein refers to a sense RNA fragment of a nucleotide sequence and an antisense RNA fragment of the nucleotide sequence, which both comprise nucleotide sequences complementary to one another, thereby allowing the sense and antisense RNA fragments to pair and form a double-stranded RNA molecule. In some embodiments, the terms refer to a double-stranded RNA molecule capable, when expressed, is at least partially reducing the level of the mRNA of the heterologous target gene. In particular, the RNAi molecule is complementary to a synthetic RNAi target sequence located in a non-coding region of the heterologous target gene.

As used herein, "RNA interference", "RNAi, and "dsRNAi" are used interchangeably herein refer to nucleic acid molecules capable of gene silencing.

The term "exon" as used herein refers to the normal sense of the term as meaning a segment of nucleic acid molecules, usually DNA, that encodes part of or all of an expressed protein.

The term "expression" as used herein refers to the biosynthesis of a gene product, preferably to the transcription and/or translation of a nucleotide sequence, for example an endogenous gene or a heterologous gene, in a cell. For example, in the case of a heterologous nucleic acid sequence, expression involves transcription of the heterologous nucleic acid sequence into mRNA and, optionally, the subsequent translation of mRNA into one or more polypeptides. Expression also refers to biosynthesis of a RNAi molecule, which refers to expression and transcription of an RNAi agent such as siRNA, shRNA, and antisense DNA but does not require translation to polypeptide sequences.

The term "expression construct" and "nucleic acid construct" as used herein are synonyms and refer to a nucleic acid sequence capable of directing the expression of a particular nucleotide sequence, such as the heterologous target gene sequence in an appropriate host cell (e.g., a mammalian cell). If translation of the desired heterologous target gene is required, it also typically comprises sequences required for proper translation of the nucleotide sequence. The coding region may code for a protein of interest but may also code for a functional RNA of interest, for example antisense RNA, dsRNA, or a nontranslated RNA, in the sense or antisense direction. The nucleic acid construct as disclosed herein can be chimeric, meaning that at least one of its components is heterologous with respect to at least one of its other components.

The term "foreign gene" or "heterologous gene" are used interchangeably herein refers to any nucleic acid (e.g., gene sequence) which is introduced into the genome of a cell. Heterologous gene sequences may include gene sequences found in that cell so long as the introduced gene to be expressed at different levels as compared to the level naturally occurring in the host cell and/or contains some modification (e.g., a point mutation, the presence of a selectable marker gene, etc.) relative to the naturally-occurring gene, or is not expressed at the same level normally in the cells as compared to the level which is being induced.

The term "gene" as used herein refers to a coding region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF) as well as, where applicable, intervening sequences (i.e., 3'UTR, 5"UTR, introns) between individual coding regions (i.e., exons). The term "structural gene" as used herein is intended to mean a DNA sequence that is transcribed into mRNA which is then translated into a sequence of amino acids characteristic of a specific polypeptide.

The term "gene product(s)" as used herein refers to include RNA transcribed from a gene, or a polypeptide encoded by a gene or translated from RNA.

The terms "genome" or "genomic DNA" as used herein refers to the heritable genetic information of a host organism. Genomic DNA comprises the DNA of the nucleus (also referred to as chromosomal DNA) but also the DNA of the plastids (e.g., chloroplasts) and other cellular organelles (e.g., mitochondria). The terms genome or genomic DNA typically refers to the chromosomal DNA of the nucleus.

The terms "heterologous target gene" as used herein refers to the nucleic acid to be expressed. A heterologous target gene can be present in the cell but not at the levels being expressed, or the nucleic acid sequence has been modified by experimental manipulations, such as example, modification being a substitution, addition, deletion, inversion or insertion of one or more nucleotide residues, for example modified by non-natural, synthetic or "artificial" methods such as, for example mutagenesis or the nucleic acid is not located in its natural or native genetic environment. Such methods for nucleic acid modification have been described (U.S. Pat. No. 5,565,350; WO 00/15815). Natural genetic environment refers to the natural chromosomal locus in the organism of origin, or to the presence in a genomic library. In the case of a genomic library, the natural genetic environment of the nucleic acid sequence is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. In some instances, a heterologous target gene is not endogenous to or not naturally associated with the cell into which it is introduced, but has been obtained from another cell. Heterologous target genes also includes an endogenous DNA sequence, which contains some modification, non-naturally occurring multiple copies of a endogenous DNA sequence, or a DNA sequence which is not naturally associated with another DNA sequence physically linked thereto. Generally, although not necessarily, heterologous target genes encodes RNA and proteins that are not normally produced by the cell into which it is expressed.

The term "endogenous" nucleotide sequence refers to a nucleotide sequence, which is present in the genome of the cell under normal conditions, i.e. a nucleotide sequence which present normally in the cell and is not introduced into the cell or by other genetic manipulation strategies. A nucleic acid sequence referred to as a "non-endogenous" or "synthetic" sequence refers to a sequence, where the entire sequence is not found in the cell to which the nucleic acid is introduced. In some embodiments, the RNAi target site is a non-endogenous or synthetic sequence, meaning the entire sequence is not found within the cell that the nucleic acid construct is introduced into.

The term an "essential" gene is a gene encoding a protein such as e.g. a biosynthetic enzyme, receptor, signal transduction protein, structural gene product, or transport protein that is essential to the growth or survival of the organism or cell.

The term "homologous DNA Sequence" as used herein refers to a DNA sequence naturally associated with a host cell or another DNA sequence.

The term "leakiness" or "leaky" as used in reference to "promoter leakiness" refers to some level of expression of the transgene which is operatively linked to the promoter, even when the promoter is not intended to result in transgene expression (i.e. when the promoter is in the "off" state, a background level of expression of the transgene which is operatively linked to such promoter exists). As an illustrative example using a tissue-specific promoter, a "leaky promoter" is one in which expression of a transgene occurs in tissue where a tissue-specific promoter is not active, i.e. expression occurs in a non-specific tissue. Stated in another way using a kidney-specific promoter as an example; if at least some level of transgene expression occurs in at least one tissue other than the kidney, where the transgene is operatively linked to a kidney specific promoter, the kidney specific promoter would be considered a leaky promoter. In another example using inducible promoters, for example a Tet-on promoter, a leaky promoter is where some level of transgene expression (which is operatively linked to the Tet-on promoter) still occurs in the absence of the inducer agent, tetracycline. Typically, most inducible promoters and tissue-specific promoters have approximately 10%-30% or 10-20% unintended or background transgene expression when the promoter is not active, for example, the background of leakiness of transgene expression is about 10%-20% or about 10-30%.

The term "mammal" or "mammalian" are used interchangeably herein, are intended to encompass their normal meaning. While the invention is most desirably intended for efficacy in humans, it may also be employed in domestic mammals such as canines, felines, and equines, as well as in mammals of particular interest, e.g., zoo animals, farmstock, transgenic animals, rodents and the like.

The term "mature protein" as used herein refers to a protein which is normally synthesized in pre-form, such as, for example, a pre-protein comprising a protein plus additional protein components, such as targeting or signal peptides, which direct translocation to a specific cellular organelle. Post-translation processing of the pre-protein results in the mature protein, for example cleavage of the pre-protein components. In some instances, a pre-protein can comprise a biologically inactive protein, which on post-translation processing renders an active protein.

The term "minimal promoter" as used herein refers to the minimal nucleic acid regions of promoter elements while also maintaining a functional promoter.

The term "non-coding" refers to sequences of nucleic acid molecules that do not encode part or all of an expressed protein. Non-coding sequences include but are not limited to introns, promoter regions, 3' untranslated regions (3'UTR), and 5' untranslated regions (5'UTR).

The term "RNAi target sequence" or "RNAi target site" as used herein is a portion of a nucleic acid that is identified, to be complementary nucleic acid to the RNAi agent as disclosed herein.

The term "coding region" as used herein, refers to a portion of the nucleic acid, which is transcribed and translated in a sequence-specific manner to produce into a particular polypeptide or protein when placed under the control of appropriate regulatory sequences. The coding region is said to encode such a polypeptide or protein.

The terms "nucleic acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or doublestranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used inter-changeably herein with "gene", "cDNA, "mRNA", "oligonucleotide," and "polynucleotide". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. shRNAs also can comprise non-natural elements such as non-natural bases, e.g., ionosin and xanthine, nonnatural sugars, e.g., 2'-methoxy ribose, or non-natural phosphodiester linkages, e.g., methylphosphonates, phosphorothioates and peptides. The term "nucleic acid" or "oligonucleotide" or "polynucleotide" are used interchangeably herein and refers to at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe for a probe that can hybridize to the target sequence under stringent hybridization conditions. Thus, a nucleic acid also encompasses a probe that hybridizes under stringent hybridization conditions.

The term "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthene hypoxanthine, isocytosine and isoguanine. Nucleic acids can be obtained by chemical synthesis methods or by recombinant methods.

A nucleic acid will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog can be located for example at the 5'-end and/or the 3'-end of the nucleic acid molecule. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e. g. 7 deaza-adenosine; O and N-alkylated nucleotides, e.g. N6-methyl adenosine are suitable. The 2' OH— group can be replaced by a group selected from H, OR, R, halo, SH, SR, $NH_2$, NHR, $NR_2$ or CN, wherein R is C—C6 alkyl, alkenyl or alkynyl and halo is F, Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs can be made.

The term "heterologous target sequence" or "heterologous target gene" as used herein, refers to any nucleotide sequence, the manipulation of which may be deemed desirable for any reason (e.g., confer improved qualities), by one of ordinary skill in the art. Such nucleotide sequences include, but are not limited to, coding sequences of heterologous genes or structural genes (e.g., reporter genes, selection marker genes, drug resistance genes, growth factors, etc.), and non-coding regulatory sequences which do not encode an mRNA or protein product, (e.g., promoter sequence, polyadenylation sequence, termination sequence, enhancer sequence, RNAi molecules etc.). A nucleic acid sequence of interest may preferably encode for a heterologous gene, for example a valuable trait, for example but not limited to, a heterologous gene encoding a toxin protein, or fragment thereof for use in cancer therapeutics etc. A "heterologous target gene" or "transgene" of the present invention can be associated with a pathological condition. For example, the expression of such a heterologous target gene may decrease a symptom associated with a disease, disorder or malignancy or pathogen, e.g., a viral gene, or a tumor associated gene, or a defective gene (e.g., an abnormal cancer-causing gene), or an autoimmune disease-associated gene. The target gene may also be a heterologous gene expressed in a recombinant cell or a genetically altered organism. By determining or modulating, for example, increasing the level or function of the gene, valuable information and therapeutic benefits in medicine, veterinary medicine, and biology may be obtained.

The terms "target", "target gene" and "target nucleotide sequence" are used equivalently herein and refers to a target gene can be any gene of interest present in an organism. A target gene may be endogenous or introduced. For example, a target gene is a gene of known function or is a gene whose function is unknown, but whose total or partial nucleotide sequence is known. Alternatively, the function of a target gene and its nucleotide sequence are both unknown. A target gene can be a native gene of the eukaryotic cell or can be a heterologous gene which has previously been introduced into the eukaryotic cell or a parent cell of said eukaryotic cell, for example by genetic transformation. A heterologous target gene can be stably integrated in the genome of the eukaryotic cell or is present in the eukaryotic cell as an extrachromosomal molecule, e.g. as an autonomously replicating extrachromosomal molecule. A target gene can include polynucleotides comprising a region that encodes a polypeptide or polynucleotide region that regulates replication, transcription, translation, or other process important in expression of the target protein; or a polynucleotide comprising a region that encodes the target polypeptide and a region that regulates expression of the target polypeptide; or non-coding regions such as the 5' or 3' UTR or introns. A target gene may refer to, for example, an mRNA molecule produced by transcription a gene of interest.

The term "oligonucleotide" as used herein refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

The term "operable linkage" or "operably linked" are used interchangeably herein, are to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of the linked nucleic acid sequence. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. In some embodiments, arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly can be any distance, and in some embodiments is less than 200 base pairs, especially less than 100 base pairs, less than 50 base pairs. In some embodiments, the nucleic acid sequence to be transcribed is located behind the promoter in such a way that the transcription start is identical with the desired beginning of the chimeric RNA of the invention. Operable linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. In some embodiments, the expression construct, consisting of a linkage of promoter and nucleic acid sequence to be expressed, can exist in a vector integrated form and be inserted into a plant genome, for example by transformation.

The term "nucleic acid construct" as used herein refers to a nucleic acid at least partly created by recombinant methods. The term "DNA construct" is referring to a polynucleotide construct consisting of deoxyribonucleotides. The construct can be single or double stranded. The construct can be circular or linear. A person of ordinary skill in the art is familiar with a variety of ways to obtain one of a DNA construct. Constructs can be prepared by means of customary recombination and cloning techniques as are described, for example, in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands.

The terms "polypeptide", "peptide", "oligopeptide", "polypeptide", "gene product", "expression product" and "protein" are used interchangeably herein to refer to a polymer or oligomer of consecutive amino acid residues.

The terms "promoter," "promoter element," or "promoter sequence" are equivalents and as used herein, refers to a DNA sequence which when operatively linked to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host cells (e.g., tissue promoters or pathogens like viruses). If a promoter is an inducible promoter, then the rate of transcription in creases in response to an inducing agent. In contrast, the rate of transcription is not regulated by an inducing agent if the promoter is a constitutive promoter. Also, the promoter may be regulated in a tissue-specific or tissue preferred manner such that it is only active in transcribing the associated coding region in a specific tissue type(s) such as leaves, roots or meristem. The term "tissue specific" as it applies to a promoter refers to a promoter that is capable of directing selective expression of a nucleotide sequence of interest to a specific type of tissue (e.g., liver) in the relative absence of expression of the same nucleotide sequence of interest in a different type of tissue (e.g., kidney). Tissue specificity of a promoter may be evaluated by, for example, operably linking a reporter gene to the promoter sequence to generate a reporter construct, introducing the reporter construct into the genome of an organism, e.g. an animal model such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining or immunohistochemical staining.

The term "constitutive" when made in reference to a promoter means that the promoter is capable of directing transcription of an operably linked nucleic acid sequence in the absence of a stimulus (e.g., heat shock, chemicals, agents, light, etc.). Typically, constitutive promoters are capable of directing expression of a transgene in substantially any cell and any tissue.

In contrast, the term "regulatable" or "inducible" promoter referred to herein is one which is capable of directing a level of transcription of an operably linked nuclei acid sequence in the presence of a stimulus (e.g., heat shock, chemicals, light, agent etc.) which is different from the level of transcription of the operably linked nucleic acid sequence in the absence of the stimulus.

The term "sense" as used herein refers to a nucleic acid having a sequence which is homologous or identical to a target sequence, for example a sequence which binds to a protein transcription factor and which is involved in the expression of a given gene. According to a preferred embodiment, the nucleic acid comprises a gene of interest and elements allowing the expression of the said gene of interest.

In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of at least 10 nucleotides, or at least 11, 12, 13, 14, 15, 16, 17, 18, 19, 20, 21, 22 or up to 50 nucleotides of the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

In its broadest sense, the term "substantially identical", when used herein with respect to a nucleotide sequence, means a nucleotide sequence corresponding to a reference or target nucleotide sequence, wherein the percentage of identity between the substantially identical nucleotide sequence and the reference or target nucleotide sequence is at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of 10-22 nucleotides, such as at least 10, 11, 12, 13, 14, 15, 16, 17, 18, 19, 20, 21, 22 or up to 50 nucleotides of a nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially identical" to a reference nucleotide sequence hybridizes to the exact complementary sequence of the reference nucleotide sequence (i.e. its corresponding strand in a double-stranded molecule) under low stringency conditions, preferably medium stringency conditions, most preferably high stringency conditions (as defined above). Homologues of a specific nucleotide sequence include nucleotide sequences that encode an amino acid sequence that is at least 24% identical, at least 35% identical, at least 50% identical, at least 65% identical to the reference amino acid sequence, as measured using the parameters described above, wherein the amino acid sequence encoded by the homolog has the same biological activity as the protein encoded by the specific nucleotide. The term "substantially non-identical" refers to a nucleotide sequence that does not hybridize to the nucleic acid sequence under stringent conditions. The term "substantially identical", when used herein with respect to a polypeptide, means a protein corresponding to a reference polypeptide, wherein the polypeptide has substantially the same structure and function as the reference protein, e.g. where only changes in amino acids sequence not affecting the polypeptide function occur. When used for a polypeptide or an amino acid sequence, the percentage of identity between the substantially similar and the reference polypeptide or amino acid sequence is at least 24%, at least 30%, at least 45%, at least 60%, at least 75%, at least 90%, at least 95%, at least 99%, using default GAP analysis parameters as described above. Homologues are amino acid sequences that are at least 24% identical, more preferably at least 35% identical, yet more preferably at least 50% identical, yet more preferably at least 65% identical to the reference polypeptide or amino acid sequence, as measured using the parameters described above, wherein the amino acid sequence encoded by the homolog has the same biological activity as the reference polypeptide.

As used herein, "synthetic" as used herein in reference to a synthetic RNAi target site refers to a sequence of nucleic acids which is non-endogenous to the cell or organism in which the nucleic acid is present in. Such synthetic nucleic acid sequences can be obtained by methods commonly known in the art, for example by PCR or can be synthesized using commercial oligonucleotide synthesis machines, including but not limited to the ABI 394 and ABI 3900 DNA/RNA Synthesizers available from Applied Biosystems, Inc. or other commercially-equivalent synthesizers.

The term "correspond," as in "an RNAi molecule comprising a sequence that corresponds to a target sequence," means that the two sequences are complementary or homologous or bear such other biologically rational relationship to each other (e.g., based on the sequence of nucleomonomers and their base-pairing properties).

The term "transformation" as used herein refers to the introduction of genetic material (e.g., a transgene or heterologous nucleic acid molecules) into a cell, tissue or organism. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme linked immunosorbent assay (ELISA), which detects the presence of a polypeptide encoded by one or more of the transgenes. Alternatively, transient transformation may be detected by detecting the activity of the protein (e.g., β-glucuronidase) encoded by the transgene (e.g., the uid A gene). The term "transient transformant" refers to a cell which has transiently incorporated one or more transgenes. In contrast, the term "stable transformation" or "stably transformed" refers to the introduction and integration of one or more transgenes into the genome of a cell, preferably resulting in chromosomal integration and stable heritability through meiosis. Stable transformation of a cell may be detected by Southern blot hybridization of genomic DNA of the cell with nucleic acid sequences, which are capable of binding to one or more of the transgenes. Alternatively, stable transformation of a cell may also be detected by the polymerase chain reaction of genomic DNA of the cell to amplify transgene sequences. The term "stable transformant" refers to a cell, which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene. Transformation also includes introduction of genetic material into plant cells in the form of plant viral vectors involving epichromosomal replication and gene expression, which may exhibit variable properties with respect to meiotic stability. Transformed cells, tissues, or plants are understood to encompass not only the end product of a transformation process, but also transgenic progeny thereof.

The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence. The term transgenic when referring to a cell, tissue or organisms means transformed, preferably stably transformed, with a recombinant DNA molecule that preferably comprises a suitable promoter operatively linked to a DNA sequence of interest.

The term "vectors" is used interchangeably with "plasmid" to refer to a nucleic acid molecule capable of transporting another nucleic acid to which it has been linked. Vectors capable of directing the expression of genes and/or nucleic acid sequence to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. Other expression vectors can be used in different embodiments of the invention, for example, but are not limited to, plasmids, episomes, bacteriophages or viral vectors, and such vectors can integrate into the host's genome or replicate autonomously in the particular cell. Other forms of expression vectors known by those skilled in the art which serve the equivalent functions can also be used. Expression vectors comprise expression vectors for stable or transient expression encoding the DNA. A vector can be a plasmid, bacteriophage, bacterial artificial chromosome or yeast artificial chromosome. A vector can be a DNA or RNA vector. A vector can be either a self replicating extrachromosomal vector or a vector which integrate into a host genome.

As used herein, the term "vector" refers to a nucleic acid molecule capable of transporting another nucleic acid to which it has been linked. One type of vector is a genomic integrated vector, or "integrated vector", which can become integrated into the chromosomal DNA of the host cell. Another type of vector is an episomal vector, i.e., a nucleic acid capable of extra-chromosomal replication. Vectors capable of directing the expression of genes to which they are operatively linked are referred to herein as "expression vectors". In the present specification, "plasmid" and "vector" are used interchangeably unless otherwise clear from the context. Expression vectors designed to produce RNAs as described herein in vitro or in vivo may contain sequences under the control of any RNA polymerase, including mitochondrial RNA polymerase, RNA pol I, RNA pol II, and RNA pol III. Vectors may be desirably designed to utilize an endogenous mitochondrial RNA polymerase (e.g., human mitochondrial RNA polymerase, in which case such vectors may utilize the corresponding human mitochondrial promoter). Mitochondrial polymerases may be used to generate capped (through expression of a capping enzyme) or uncapped messages in vivo. RNA pol I, RNA pol II, and RNA pol III transcripts may also be generated in vivo. Such RNAs may be capped or not, and if desired, cytoplasmic capping may be accomplished by various means including use of a capping enzyme such as a vaccinia capping enzyme or an alpha virus capping enzyme.

Such plasmids or vectors can include plasmid sequences from bacteria, viruses or phages. Such vectors include chromosomal, episomal and virus-derived vectors e.g., vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids. Thus, one exemplary vector is a single or double-stranded phage vector. Another exemplary vector is a single or double-stranded RNA or DNA viral vector. Such vectors may be introduced into cells as polynucleotides, preferably DNA, by well known techniques for introducing DNA and RNA into cells. The vectors, in the case of phage and viral vectors may also be and preferably are introduced into cells as packaged or encapsidated virus by well known techniques for infection and transduction. Viral vectors may be replication competent or replication defective. In the latter case, viral propagation generally occurs only in complementing host cells.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116: 281-297), comprises a dsRNA molecule.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, amlady, disorder, sickness, illness, complaint, inderdisposion, affection.

The term "malignancy" and "cancer" are used interchangeably herein, refers to diseases that are characterized by uncontrolled, abnormal growth of cells. Cancer cells can spread locally or through the bloodstream and lymphatic system to other parts of the body. The term "malignancy" or "cancer" are used interchangeably herein and refers to any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer. The term "tumor" or "tumor cell" are used interchangeably herein, refers to the tissue mass or tissue type of cell that is undergoing abnormal proliferation.

In this specification and the appended claims, the singular forms "a," "an," and "the" include plural references unless the context clearly dictates otherwise, and therefore "a" and "an" are used herein to refer to one or to more than one (i.e., at least one) of the grammatical object of the article. By way of example, "an element" means one element or more than one element, and reference to a composition for delivering "an agent" includes reference to one or more agents.

Compositions or methods "comprising" one or more recited elements may include other elements not specifically recited. For example, a composition that comprises a fibril component peptide encompasses both the isolated peptide and the peptide as a component of a larger polypeptide sequence. By way of further example, a composition that comprises elements A and B also encompasses a composition consisting of A, B and C. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination."

Other than in the operating examples, or where otherwise indicated, all numbers expressing quantities of ingredients or reaction conditions used herein should be understood as modified in all instances by the term "about."

This invention is further illustrated by the following examples which should not be construed as limiting. The contents of all references cited throughout this application, as well as the figures and tables are incorporated herein by reference. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

General Description

In some embodiments, the present invention is directed to compositions and methods comprising systems useful in controlling expression of a heterologous target gene through controlled expression of an RNAi agent. The present invention provides methods and compositions for an externally controllable system for manipulating the regulation of a heterologous target gene through a dual regulatory system comprising (i) an inducible promoter system activated by an inducer agent, and (ii) an RNA interference (RNAi) agent which gene silences the heterologous target gene, where the RNAi interference agent is inactivated by the inducer agent. In some embodiments, the inducible promoter and/or the RNAi interference agent can also be regulated in a tissue-specific manner, and/or in a localized manner.

In some embodiments of the present invention, the methods and systems as disclosed herein relate to a nucleic acid encoding the RNAi agent which targets a non-endogenous or synthetic RNAi target site located within the non-coding region of the heterologous target gene. In some embodiments, the RNAi agent is constitutive in the "on" position and the expression of the RNAi agent is controlled by a repressible promoter, such as, for example but not limited to a repressible promoter regulated by a Tet repressor (Tet$^R$) protein. In some embodiments, the nucleic acid encoding the first repressor protein is controlled by a second repressor promoter, such as for example but not limited to a LacO promoter. In alternative embodiments, the first repressor protein is controlled by an inducible promoter. In some embodiments, second repressor promoter or inducible promoter also controls the expression of the heterologous target gene.

In one embodiment, the RNAi agent is operatively linked to a repressor promoter such as the TetO promoter, and the expression of the Tet repressor protein (TetR) is operatively linked to a second repressor promoter, the LacO promoter. In some embodiments, the expression of the Lac repressor protein (LacI) is operatively linked to a promoter, such as a tissue specific promoter or a constitutive promoter. In such embodiments, the expression of LacI will repress expression of nucleic acids operatively linked to the LacO promoter, and thus expression of LacI will repress expression of the Tet$^R$ protein. In such embodiments, lack of Tet$^R$ will result in expression of proteins from the TetO promoter, thus expression of the RNAi and gene silencing of the heterologous target gene. In some embodiments, the nucleic acid of the heterologous target gene is also operatively linked to the LacO promoter.

In further embodiments, for example, LacI can be inhibited or inactivated by externally applied agents, such as, for example IPTG or derivatives or analogues thereof. In such embodiments, inhibition of LacI by IPTG results in the expression of genes operatively linked to the LacO promoter, resulting in expression of the heterologous target gene and expression of the $Tet^R$, where the TetR represses gene expression from the TetO promoter and inhibits the expression of the RNAi agent and prevents gene silencing of the heterologous target gene. In alternative embodiments, the absence of an externally applied agents, such as IPTG, will result in active LacI and repression of genes operatively linked to the LacO promoter, resulting in repression of heterologous target gene expression and $Tet^R$ expression. Repression of $Tet^R$ allows expression from genes operatively linked to the TetO, such as RNAi expression which can function to gene silence any background expression of the heterologous target gene.

In some embodiments, the compositions and methods as disclosed herein comprise the use of an externally applied agent, such as a drug or one or more other agents to co-regulate the expression of the second repressor promoter and the expression of the nucleotide sequence encoding the RNAi interference agent which binds to a RNAi target site located in a non-coding region of the heterologous target gene.

In particular embodiments, the present invention provides a nucleic acid construct comprising a region encoding a RNAi agent which targets a region referred to herein as "RNAi target site" which is located within a non-coding region of the heterologous target gene. In some embodiments, the nucleic acid encoding the RNAi agent is operatively linked to a externally controlled promoter, and the construct may be further defined as a vector. The externally controlled promoter may be a repressible promoter, whereby the expression of the encoded RNAi agent can be downregulated by means of an externally applied agent, such as, for example but not limited to an inducer agent.

I. Promoters

The term "promoter" as used herein refers to any sequence that regulates the expression of a nucleic acid sequence, such as, the heterologous target gene, RNAi agent or nucleic acids encoding repressor proteins. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors. The phrases "operable linked," "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

A. Repressible and Inducible promoters Dual Inducer-Repressor System to Switch off the RNAi Agent: First Repressor Protein Operatively Linked to an Inducible Promoter.

In some embodiments of the present invention, the methods and systems as disclosed herein relate to a nucleic acid encoding the RNAi agent which targets a RNAi target site located within a non-coding region of the heterologous target gene, where the expression of the RNAi is controlled by a repressible promoter, such as, for example but not limited to a repressible promoter such as TetO, which regulated by a Tet repressor ($Tet^R$) protein. In some embodiments, the nucleic acid encoding the repressor protein is controlled by an inducible promoter, and thus is an inducer-repressor system. In some embodiments, the inducible promoter also controls the expression of the heterologous target gene.

In some embodiments, the repressible promoter is regulated by a Tet repressor and/or is defined as further comprising at least one tetO sequence. Alternatively, a repressible promoter useful as discloser herein, may be regulated by the lad repressor, or the repressible promoter may be from the gene of ANB1, HEM 13, ERG 11, OLE 1, GAL1, GAL10, ADH2, or $TET^R$.

In some embodiments, the nucleic acid encoding the repressible protein to the repressible promoter (which controls the expression of the RNAi agent) is operatively linked to an inducible promoter. In such embodiments, an externally applied agent to the inducible promoter activates the expression of the encoded repressor protein, which in turn binds to the repressor promoter to downregulates the expression of the operatively linked RNAi agent. In some embodiments, the heterologous gene target and the nucleic acid encoding the repressor protein are operatively linked to the inducible promoter. In such embodiments, the externally applied agent induces the expression of the heterologous gene target and the repressor protein which downregulates the expression of the RNAi to attenuate RNAi mediated gene silencing of the heterologous gene target.

Dual Repressor-Repressor System to Switch Off the RNAi Agent: First Repressor Protein Operatively Linked to Second Repressor Promoter.

Another aspect of the present invention relates to a dual repressor-repressor system. In such an embodiment, the expression of the RNAi agent which targets the RNAi target site located within a non-coding region of the heterologous target gene is operatively linked to a first repressor promoter (R1). In such an embodiment, a nucleic acid encoding a first repressor protein (herein termed "RP1") which represses transcription from a first repressible promoter (R1) (which controls the expression of the RNAi agent) is operatively linked to a second repressible promoter (R2). In such embodiments, the expression of the second repressible protein (RP2) represses expression from the second repressible promoter (R2) and thus prevents the expression of the first repressor protein (RP1). Thus, absence of the first repressor protein (RP1) allows transcription of genes operatively linked to the first repressible promoter (R1) and results in the expression of the RNAi agent. Accordingly, the presence of the second repressor protein (RP2) results in the expression of the RNAi agent, and thus gene silencing of the heterologous gene target.

In some embodiments, the second repressor protein (RP2) can be inactivated or inhibited by an externally applied agent. In such embodiments, inhibition or inactivation of the second repressor protein (RP2) leads to expression of the first repressor protein (RP1) which represses transcription from a first repressible promoter (R1) and reduces the expression of the RNAi agent. Accordingly, absence or inactivation of the second repressor protein (RP2) results in the downregulation of the expression of the RNAi agent, and thus prevents gene silencing of the heterologous gene target.

In some embodiments, both the heterologous gene target and the nucleic acid encoding the first repressor protein (RP1) are operatively linked to the second repressor promoter (R2). In such embodiments, the inactivation of the second repressor protein (RP2), such as for example by an externally applied agent, induces the expression of the heterologous gene target and the first repressor protein (RP1), which down regulates the expression of the RNAi to attenuate RNAi mediated gene silencing of the heterologous gene target.

In a particular embodiment of the present invention, the RNAi agent is operatively linked to a repressor promoter such as the TetO promoter, and the expression of the Tet repressor protein (TetR) is operatively linked to a second repressor promoter, the LacO promoter. In some embodiments, the expression of the Lac repressor protein (LacI) is operatively linked to a promoter, such as a tissue specific promoter or a constitutive promoter. In such embodiments, the expression of LacI will repress expression of nucleic acids operatively linked to the LacO promoter, and thus expression of LacI will repress expression of the $Tet^R$ protein. In such embodiments, lack of $Tet^R$ will result in expression of proteins from the TetO promoter, thus expression of the RNAi and gene silencing of the heterologous target gene. In some embodiments, the nucleic acid of the heterologous target gene is also operatively linked to the LacO promoter.

In further embodiments, LacI can be inhibited or inactivated by externally applied agents, such as, for example IPTG or derivatives or analogues thereof. In such embodiments, inhibition of LacI by IPTG results in expression from the LacO promoter, resulting in expression of the heterologous target gene and expression of the $Tet^R$, where the TetR represses gene expression from the TetO promoter and inhibits the expression of the RNAi agent and prevents gene silencing of the heterologous target gene. In alternative embodiments, the absence of an externally applied agents such as IPTG, will result in active LacI and repression of genes operatively linked to the LacO promoter, resulting in repression of heterologous target gene expression and $Tet^R$ expression. Repression of $Tet^R$ allows expression from genes operatively linked to the TetO, such as RNAi expression which can function to gene silence any background expression of the heterologous target gene.

Repressor System to Switch on the RNAi Agent.

In some embodiments of the present invention, the methods and systems as disclosed herein relate to a nucleic acid encoding the RNAi agent which targets a RNAi target site located within a non-coding region of the heterologous target gene, where the expression of the RNAi is controlled by a repressible promoter, such as, for example but not limited to a repressible promoter such as LacO, which regulated by a LacI repressor protein. In some embodiments, the nucleic acid encoding the repressor protein, such as LacI is operatively linked to a constitutive promoter or a tissue-specific promoter. In such embodiments, in a non-induced state, expression of the LacI repressor binds to the LacO repressor promoter inhibiting the expression of the operatively linked RNAi agent. Thus, in a normal state the expression of the RNAi agent is in the "off" state and does not gene silence the heterologous target gene, and by addition of externally applied agents, such as IPTG, results in the inhibition or inactivation of LacI and subsequently allows expression of genes operatively linked to the LacO promoter such as the expression of the RNAi agent. Accordingly, such embodiments are useful in tight control of inducible gene expression where it is desirable to switch off a constitutively expressed heterologous target gene.

In some embodiments, the heterologous target gene is also negatively regulated to the LacO promoter, meaning that in the presence of LacI, the expression of the heterologous target gene occurs, whereas when LacI is inactivated or inhibited, the expression of the heterologous target gene does not occur.

The various polynucleotides and polynucleotide sequences of the invention may be on or part of a single polynucleotide molecule or they may be located or constitute separate polynucleotide molecules. The different polynucleotides and polynucleotide sequences, if located on the same molecule, may be adjoining, contiguous, next to, or near one another. The arrangement of these sequences will allow for the transcriptional regulation of the siRNA-encoding polynucleotide, and such arrangements can readily be configured by those of ordinary skill in the art. Moreover, embodiments of the invention disclose particular spatial arrangements of relevant sequences.

(i) Repressor Promoters

Promoters contemplated in the invention include conditional promoters, often referred to herein as "repressor promoters". A conditional promoter or a repressor promoter is a promoter that is active only under certain conditions. For example, the promoter may be inactive or repressed when a particular repressor agent, such as a chemical compound, or particular protein referred to as a "repressor protein" is present. When the agent is no longer present, transcription is activated or de-repressed. Examples of conditional promoters may include the promoter Met25 (Kerjan P. et al., 1986), which can be regulated as a function of methionine concentration, or the promoters GAL1 or GAL10 (Johnston and Davis, 1984), which can be regulated as a function of galactose concentration, but are not limited to such.

A repressible promoter is one whose ability to promote transcription is at least partially responsive to the presence or action of a repressor, which is a compound or protein that acts to repress the promoter and so reduce, inhibit, or repress transcription of the polynucleotide under the influence of the promoter. Repressible promoters are characterized by resulting in lower levels of transcription activity when in the presence of, influenced by, or contacted by the repressor than when not in the presence of, under the influence of, or in contact with the promoter. The repressor may be endogenous, or a normally exogenous compound or protein that is administered in such a way as to be active in repressing the repressible promoter. Provision of the repressor, i.e. a compound or protein, may itself be the result of transcription or expression of a polynucleotide, which itself may be under the control or an inducible or repressible promoter.

In specific embodiments, the nucleic acid construct as disclosed herein comprises a repressor promoter which transcriptionally controls the expression of the RNAi agent of the nucleic acid construct. In some embodiments, the expression of the repressor protein to the repressor promoter can be transcriptionally controlled by an inducible promoter or a constitutive promoter.

In some embodiments, promoters that are controllable by an external stimulus are utilized in methods and compositions of the present invention. Examples of promoters that are controllable by external stimulus include, for example, the $P_L$ promoter, $P_R$ promoter, $P_{re}$ promoter, $P_{rm}$, promoter, $P'_R$ promoter, $T_7$ late promoters, trp promoter, tac promoter, lac promoter, gal promoter, ara promoter or recA promoter or fragments thereof. In particular embodiments, operator sequences from these promoters are utilized in the nucleic acid construct and systems of the present invention.

In particular embodiments of the present invention, control of expression is generated through the use of a particular system comprising both polynucleotide and polypeptide components. In both prokaryotes and eukaryotes, polypeptides having affinity for specific sites on DNA modulate transcriptional expression of genes, and interaction with DNA at specific sites in genes, the polypeptides, herein referred to "repressor proteins" or "repressors," hinder transcription by, for example, making the DNA inaccessible to RNA polymerase.

Typically, the LTRi construct as disclosed herein comprises an RNAi agent operatively linked to at least one tet operator (tetO) sequence. The tetO sequence can be obtained, for example, according to Hillen & Wissmann, "Topics in Molecular and Structural Biology," in Protein-Nucleic Acid Interaction, Saeger & Heinemann, eds., Macmillan, London, 1989, Vol. 10, pp. 143-162, the contents of which are fully incorporated by reference herein. Other tetO sequences that may be used in the practice of the invention may be obtained from Genbank and/or are disclosed in Waters, S. H. et al. (1983) Nucl. Acids Res. 11:6089-6105; Hillen, W. and Schollmeier, K. (1983) Nucl. Acids Res. 11:525-539; Stuber, D. and Bujard, H. (1981) Proc. Natl. Acad. Sci. USA 78:167-171; Unger, B. et al. (1984) Nucl Acids Res. 12:7693-7703; and Tovar, K. et al. (1988) Mol. Gen. Genet. 215:76-80, which are fully incorporated by reference herein in their entirety. One, two, three, four, five, six, seven, eight, nine or ten or more copies of the tet operator sequence may be employed, with a greater number of such sequences allowing an enhanced range of regulation, in some embodiments.

However, other repressor domains include ERD or SID transcriptional repressor domains can be used, for example, transcription factors and transcription factor domains that act as transcriptional repressors include, for example, MAD (see, e.g., Sommer et al., 1998; Gupta et al., 1998; Queva et al., 1998; Larsson et al., 1997; Laherty et al., 1997; and Cultraro et al., 1997); FKHR (forkhead in rhapdosarcoma gene; Ginsberg et al., 1998; Epstein et al., 1998); EGR-1 (early growth response gene product-1; Yan et al., 1998; and Liu et al., 1998); the ets2 repressor factor repressor domain (ERD; Sgouras et al, 1995); and the MAD smSIN3 interaction domain (SID; Ayer et al., 1996).

DNA-binding proteins have been characterized extensively to determine how these polypeptides actually contact the DNA molecule, for those embodiments concerning repression through direct binding mechanisms, and interact with it to influence gene expression. Some non-limiting examples of these polypeptides include those that comprise the structural motif alpha-helix-turn-alpha-helix (H-T-H). These proteins bind as dimers or tetramers to DNA at specific operator sequences that have approximately palindromic sequences. Contacts made by two adjacent alpha helices of each monomer in and around two sites in the major groove of B-form DNA are a major feature in the interface between DNA and these proteins. Proteins that bind in this manner share sequence similarity in the H-T-H region but vary in the extent of similarity in other regions. This group of proteins includes, for example, the temperate bacteriophage repressor proteins and Cro proteins, bacterial metabolic repressor proteins such as GalR, LacI, LexA, and TrpR, bacterial activator protein CAP and dual activator/repressor protein AraC, bacterial transposon and plasmid TetR proteins, the yeast mating type regulator proteins MATa1 and MATalpha2 and eukaryotic homeobox proteins.

Other repressors have little or no sequence homology to H-T-H binding proteins and have no H-T-H binding motif. Binding of operators with approximate palindromic sequence symmetry is observed among some proteins of this group, such as *Salmonella typhimurium* bacteriophage P22 Mnt protein (VERS87a) and *E. coli* TyrR repressor protein (DEFE86). Others of this group bind to operator sequences that are partially symmetric (*S. typhimurium* phage P22 Arc protein, VERS87b; *E. coli* Fur protein, DEL087; plasmid R6K pi protein, FILU85) or non-symmetric (phage Mu repressor, KRAU86).

A skilled artisan recognizes that a repressor and/or DNA binding domain utilized in the present invention can comprise a mutation, as compared to wild-type, so long as the mutation does not deleteriously affect the respective functions of these components, and these mutated components may be utilized in methods and compositions of the present invention.

(ii) Inducible Promoters

Inducible promoters are characterized by resulting in additional transcription activity when in the presence of, influenced by, or contacted by the inducer than when not in the presence of, under the influence of, or in contact with the promoter. The inducer may be endogenous, or a normally exogenous compound or protein that is administered in such a way as to be active in inducing expression from the inducible promoter. In some embodiments, the inducer agent, i.e. a compound or protein, can itself be the result of transcription or expression of a polynucleotide (i.e. can be a repressor protein), which itself may be under the control or an inducible or repressible promoter. Examples of inducible promoters include but are not limited to; tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and the like.

Inducible promoters useful in the methods and systems of the present invention are capable of functioning in a eukaryotic host organism. Preferred embodiments include mammalian inducible promoters, although inducible promoters from other organisms as well as synthetic promoters designed to function in a eukaryotic host may be used. The important functional characteristic of the inducible promoters of the present invention is their ultimate inducibility by exposure to an externally applied agent, such as an environmental inducing agent. Appropriate environmental inducing agents include exposure to heat, various steroidal compounds, divalent cations (including $Cu^{+2}$ and $Zn^{+2}$), galactose, tetracycline, IPTG (isopropyl-β-D thiogalactoside), as well as other naturally occurring and synthetic inducing agents and gratuitous inducers.

The nucleic acid construct and systems disclosed herein encompass the inducibility of a eukaryotic promoter by either of two mechanisms. In particular embodiments of the present invention, the nucleic acid construct comprises suitable inducible promoters can be dependent upon transcriptional activators that, in turn, are reliant upon an environmental inducing agent. In some embodiments, the inducible promoters can be repressed by a transcriptional repressor which itself is rendered inactive by an environmental inducing agent. Thus the inducible promoter can be either one that is induced by an environmental agent that positively activates a transcriptional activator, or one which is derepressed by an environmental agent which negatively regulates a transcriptional repressor. For example, as demonstrated in the Examples, one inducible promoter used is the LacO system, whereby addition of the externally added agent IPTG negatively regulates the transcriptional repressor LacI.

Inducible promoters useful in the methods and systems as disclosed herein include those controlled by the action of latent transcriptional activators that are subject to induction by the action of environmental inducing agents. Preferred examples include the copper-inducible promoters of the yeast genes CUP1, CRS5, and SOD1 that are subject to copper-dependent activation by the yeast ACE1 transcriptional activator (see e.g. Strain and Culotta, 1996; Hottiger et al., 1994; Lapinskas et al., 1993; and Gralla et al., 1991). Alternatively, the copper inducible promoter of the yeast gene CTT1 (encoding cytosolic catalase T), which operates independently of the ACE1 transcriptional activator (Lapinskas et al., 1993), can be utilized. The copper concentrations required for effective induction of these genes are suitably low so as to be tolerated by most cell systems, including yeast and *Drosophila* cells. Alternatively, other naturally occurring inducible promoters can be used in the present invention including: steroid inducible gene promoters (see e.g. Oligino et al. (1998) Gene Ther. 5: 491-6); galactose inducible promoters from yeast (see e.g. Johnston (1987) Microbiol Rev 51: 458-76; Ruzzi et al. (1987) Mol Cell Biol 7: 991-7); and various heat shock gene promoters. Many eukaryotic transcriptional activators have been shown to function in a broad range of eukaryotic host cells, and so, for example, many of the inducible promoters identified in yeast can be adapted for use in a mammalian host cell as well. For example, a unique synthetic transcriptional induction system for mammalian cells has been developed based upon a GAL4-estrogen receptor fusion protein that induces mammalian promoters containing GAL4 binding sites (Braselmann et al. (1993) Proc Natl Acad Sci USA 90: 1657-61). These and other inducible promoters responsive to transcriptional activators that are dependent upon specific inducing agents are suitable for use with the present invention.

Inducible promoters useful in the methods and systems as disclosed herein also include those that are repressed by repressors that are subject to inactivation by the action of environmental inducing agents. Examples include prokaryotic repressors that can transcriptionally repress eukaryotic promoters that have been engineered to incorporate appropriate repressor-binding operator sequences. Preferred repressors for use in the present invention are sensitive to inactivation by physiologically benign inducing agent. Thus, where the lac repressor protein is used to control the expression of a eukaryotic promoter that has been engineered to contain a lacO operator sequence, treatment of the host cell with IPTG will cause the dissociation of the lac repressor from the engineered promoter and allow transcription to occur. Similarly, where the tet repressor is used to control the expression of a eukaryotic promoter that has been engineered to contain a tetO operator sequence, treatment of the host cell with tetracycline will cause the dissociation of the tet repressor from the engineered promoter and allow transcription to occur.

An inducible promoter useful in the methods and systems as disclosed herein can be induced by one or more physiological conditions, such as changes in pH, temperature, radiation, osmotic pressure, saline gradients, cell surface binding and the concentration of one or more extrinsic or intrinsic agents. The extrinsic agent may comprise amino acids and amino acid analogs, saccharides and polysaccharides, nucleic acids, transcriptional activators and repressors, cytokines, toxins, petroleum-based compounds, metal containing compounds, salts, ions, enzyme substrate analogs and combinations thereof. In specific embodiments, the inducible promoter is activated or repressed in response to a change of an environmental condition, such as the change in concentration of a chemical, metal, radiation or nutrient or change in pH.

Furthermore, an inducible promoter useful in the methods and systems as disclosed herein can be a phage inducible promoter, nutrient inducible promoter, temperature inducible promoter, radiation inducible promoter, metal inducible promoter, hormone inducible promoter, steroid inducible promoter, and/or hybrids and combinations thereof. Promoters that are inducible by ionizing radiation can be used in certain embodiments, particularly in gene therapy of cancer, where gene expression is induced locally in the cancer cells by exposure to ionizing radiation such as UV or x-rays. Radiation inducible promoters include the non-limiting examples of fos promoter, c-jun promoter or at least one CArG domain of an Egr-1 promoter. Examples of inducible promoters include promoters from genes such as cytochrome P450 genes, heat shock protein genes, metallothionein genes, hormone-inducible genes, such as the estrogen gene promoter, and such.

In further embodiments, an inducible promoter useful in the methods and systems as disclosed herein can be $Zn^{2+}$ metallothionein promoter, metallothionein-1 promoter, human metallothionein IIA promoter, lac promoter, lacO promoter, mouse mammary tumor virus early promoter, mouse mammary tumor virus LTR promoter, triose dehydrogenase promoter, herpes simplex virus thymidine kinase promoter, simian virus 40 early promoter or retroviral myeloproliferative sarcoma virus promoter.

Examples of inducible promoters include mammalian probasin promoter, lactalbumin promoter, GRP78 promoter, or the bacterial tetracycline-inducible promoter. Other examples include heat shock, steroid hormone, heavy metal, phorbol ester, adenovirus E1A element, interferon, and serum inducible promoters.

Inducible promoters useful in the methods and systems as disclosed herein for in vivo uses may include those responsive to biologically compatible agents, such as those that are usually encountered in defined animal tissues. An example is the human PAI-1 promoter, which is inducible by tumor necrosis factor. Further suitable examples cytochrome P450 gene promoters, inducible by various toxins and other agents; heat shock protein genes, inducible by various stresses; hormone-inducible genes, such as the estrogen gene promoter, and such.

Inducible promoters may be inducible by $Cu^{2+}$, $Zn^{2+}$, tetracycline, tetracycline analog, ecdysone, glucocorticoid, tamoxifen, or an inducer of the lac operon (LacO). The promoter may be inducible by ecdysone, glucocorticoid, or tamoxifen. In specific embodiments, the inducible promoter is a phage inducible promoter, nutrient inducible promoter, temperature inducible promoter, radiation inducible promoter, metal inducible promoter, hormone inducible promoter, steroid inducible promoter, or combination thereof. Examples of radiation inducible promoters include fos promoter, jun promoter, or erg promoter.

Systems for the regulation of gene expression that may be used within the contemplated scope of the invention include regulatory systems utilizing compounds such as progesterone, estrogen, and/or ecdysone.

An expression constructs may also contain a chemically inducible promoter (review article: Gatz et al. (1997) Annu Rev Plant Physiol Plant Mol Biol 48:89-108), by means of which the expression of the heterologous target gene can be controlled at a particular point in time. Such promoters such as, for example, a salicylic acid-inducible promoter (WO 95/19443), a benzenesulfonamide-inducible promoter (EP 0 388 186), a tetracycline-inducible promoter (Gatz et al. (1991) Mol Gen Genetics 227:229-237), an abscisic acid-inducible promoter EP 0 335 528) or an ethanol-cyclohexanone-inducible promoter (WO 93/21334) can likewise be used. Also suitable is the promoter of the glutathione-S transferase isoform II gene (GST-II-27), which can be activated by exogenously applied safeners such as, for example, N,N-diallyl-2,2-dichloroacetamide (WO 93/01294) and which is operable in a large number of tissues of both monocotyledonous and dicotyledonous. Further exemplary inducible promoters that can be utilized in the instant invention include that from the ACE1 system which responds to copper (Mett et al. PNAS 90: 4567-4571 (1993)). An exemplary inducible promoter is the inducible promoter from a steroid hormone gene, the transcriptional activity of which is induced by a glucocorticosteroid hormone (Schena et al. (1991) Proc Nat'l Acad Sci USA 88:10421).

B. Inducible Agents and Inducible Systems

The administration or removal of an agent as disclosed herein results in a switch between the on or off states of the transcription of the heterologous target gene. Several small molecule ligands have been shown to mediate regulated gene expressions, either in tissue culture cells and/or in transgenic animal models. These include the FK1012 and rapamycin immunosupressive drugs (Spencer et al., 1993; Magari et al., 1997), the progesterone antagonist mifepristone (RU486) (Wang, 1994; Wang et al., 1997), the tetracycline antibiotic derivatives (Gossen and Bujard, 1992; Gossen et al., 1995; Kistner et al., 1996), and the insect steroid hormone ecdysone (No et al., 1996). All of these references are herein incorporated by reference.

By way of further example, Yao discloses in U.S. Pat. No. 6,444,871 which is incorporated herein by reference, prokaryotic elements associated with the tetracycline resistance (tet) operon, a system in which the tet repressor protein is fused with polypeptides known to modulate transcription in mammalian cells. The fusion protein has then been directed to specific sites by the positioning of the tet operator sequence. For example, the tet repressor has been fused to a transactivator (VP 16) and targeted to a tet operator sequence positioned upstream from the promoter of a selected gene (Gussen et al., 1992; Kim et al., 1995; Hennighausen et al., 1995). The tet repressor portion of the fusion protein binds to the operator thereby targeting the VP 16 activator to the specific site where the induction of transcription is desired. An alternative approach has been to fuse the tet repressor to the KRAB repressor domain and target this protein to an operator placed several hundred base pairs upstream of a gene. Using this system, it has been found that the chimeric protein, but not the tet repressor alone, is capable of producing a 10 to 15-fold suppression of CMV-regulated gene expression (Deuschle et al., 1995).

One example of a repressor promoter useful in the methods and systems as disclosed herein is the Lac repressor (lacR)/operator/inducer system of *E. coli* which and has been used to regulate gene expression by three different approaches: (1) prevention of transcription initiation by properly placed lac operators at promoter sites (Hu and Davidson, 1987; Brown et al., 1987; Figge et al., 1988; Fuerst et al., 1989; Deuschle et al., 1989; (2) blockage of transcribing RNA polymerase II during elongation by a LacR/operator complex (Deuschle et al. (1990); and (3) activation of a promoter responsive to a fusion between LacR and the activation domain of herpes simples virus (HSV) virion protein 16 (VP16) (Labow et al., 1990; Bairn et al., 1991).

In one version of the Lac system, expression of lac operator-linked sequences is constitutively activated by a LacR-VP16 fusion protein and is turned off in the presence of isopropyl-β-D-thiogalactopyranoside (IPTG) (Labow et al. (1990), cited supra). In another version of the system, a lacR-VP16 variant is used which binds to lac operators in the presence of IPTG, which can be enhanced by increasing the temperature of the cells (Bairn et al. (1991), cited supra). Thus, in some embodiments of the present invention, components of the Lac system are utilized. For example, a lac operator (LacO) may be operably linked to tissue specific promoter, and control the transcription and expression of the heterologous target gene and the first repressor proteins such as the Tet$^R$. Accordingly, the expression of the siRNA (and therefore gene silencing of the heterologous target gene) is inversely regulated as compared to the expression of the heterologous target expression, such that presence of IPTG results in inhibition of RNAi expression and induction of heterologous target gene expression.

Components of the tetracycline (Tc) resistance system of *E. coli* have also been found to function in eukaryotic cells and have been used to regulate gene expression. For example, the Tet repressor (TetR), which binds to tet operator (tetO) sequences in the absence of tetracycline and represses gene transcription, has been expressed in plant cells at sufficiently high concentrations to repress transcription from a promoter containing tet operator sequences (Gatz, C. et al. (1992) Plant J. 2:397-404). In some embodiments of the present invention, the Tet repressor system is similarly utilized.

A temperature-inducible gene regulatory system may also be used in the present invention, such as the exemplary TIGR system comprising a cold-inducible transactivator in the form of a fusion protein having a heat shock responsive regulator, rheA, fused to the VP16 transactivator (Weber et al, 2003a). The promoter responsive to this fusion thermosensor comprises a rheO element operably linked to a minimal promoter, such as the minimal version of the human cytomegalovirus immediate early promoter. At the permissive temperature of 37° C., the cold-inducible transactivator transactivate the exemplary rheO-CMV$_{min}$ promoter, permitting expression of the target gene. At 41° C., the cold-inducible transactivator no longer transactivates the rheO promoter.

Other embodiments useful in the present invention include the erythromycin-resistance regulon from *E. coli*, having repressible ($E_{off}$) and inducible ($E_{on}$) systems responsive to macrolide antibiotics, such as erythromycin, clarithromycin, and roxithromycin (Weber et al., 2002). The $E_{off}$ system utilizes an erythromycin-dependent transactivator, wherein providing a macrolide antibiotic represses transgene expression. In the $E_{on}$ system, the binding of the repressor to the operator results in repression of transgene expression. Therein, in the presence of macrolides gene expression is induced.

Fussenegger et al. (2000) describe repressible and inducible systems using a Pip (pristinamycin-induced protein) repressor encoded by the streptogramin resistance operon of *Streptomyces coelicolor*, wherein the systems are responsive to streptogramin-type antibiotics (such as, for example, pristinamycin, virginiamycin, and Synercid). The Pip DNA-binding domain is fused to a VP16 transactivation domain or to the KRAB silencing domain, for example. The presence or absence of, for example, pristinamycin, regulates the PipON and PipOFF systems in their respective manners, as described therein.

Another example of a transgene expression system utilizes a quorum-sensing (referring to particular prokaryotic molecule communication systems having diffusable signal molecules that prevent binding of a repressor to an operator site, resulting in derepression of a target regulon) system. For example, Weber et al. (2003b) employ a fusion protein comprisign the *Streptomyces coelicolor* quorum-sending receptor to a transactivating domain that regulates a chimeric promoter having a respective operator that the fusion protein binds. The expression is fine-tuned with non-toxic butyrolactones, such as SCB 1 and MP 133.

In particular embodiments, multiregulated multigene therapeutic gene expression systems that are functionally compatible with one another are utilized in the present invention (see, for example, Kramer et al. (2003)). For example, in Weber et al. (2002), the macrolide-responsive erythromycin resistance regulon system is used in conjunction with a streptogramin (PIP)-regulated and tetracycline-regulated expression systems.

In some embodiments, the inducible promoter can be a heat-inducible promoter. Any heat-inducible promoter can be used in accordance with the methods of the present invention, including but not limited to a heat-responsive element in a heat shock gene (e.g., hsp20-30, hsp27, hsp40, hsp60, hsp70, and hsp90). See Easton et al. (2000) Cell Stress Chaperones 5(4):276-290; Csermely et al. (1998) Pharmacol Ther 79(2): 129-1 68; Ohtsuka & Hata (2000) Int J Hyperthermia 16(3): 231-245; and references cited therein. Sequence similarity to heat shock proteins and heat-responsive promoter elements have also been recognized in genes initially characterized with respect to other functions, and the DNA sequences that confer heat inducibility are suitable for use in the disclosed gene therapy vectors. For example, expression of glucose-responsive genes (e.g., grp94, grp78, mortalin/grp75) (Merrick et al. (1997) Cancer Lett 119(2): 185-190; Kiang et al. (1998) FASEB J 12(14):1571-16-579), calreticulin (Szewczenko-Pawlikowski et al. (1997) Mol Cell Biochem 177(1-2): 145-1 52); clusterin (Viard et al. (1999) J Invest Dermatol 112(3):290-296; Michel et al. (1997) Biochem J 328(Ptl):45-50; Clark & Griswold (1997) J Androl 18(3):257-263), histocompatibility class I gene (HLA-G) (Ibrahim et al. (2000) Cell Stress Chaperones 5(3):207-218), and the Kunitz protease isoform of amyloid precursor protein (Shepherd et al. (2000) Neuroscience 99(2):31 7-325) are upregulated in response to heat.

In the case of clusterin, a 14 base pair element that is sufficient for heat-inducibility has been delineated (Michel et al. (1997) Biochem J 328(Pt1):45-50). Similarly, a two sequence unit comprising a 10- and a 14-base pair element in the calreticulin promoter region has been shown to confer heat-inducibility (Szewczenko-Pawlikowski et al. (1997) Mol Cell Biochem 177(1-2): 145-1 52). Other promoter responsive to non-heat stimuli that can be used. For example, the mortalin promoter is induced by low doses of ionizing radiation (Sadekova (1997) Int J Radial Biol 72(6):653-660), the hsp27 promoter is activated by 17. beta.-estradiol and estrogen receptor agonists (Porter et al. (2001) J Mol Endocrinol 26(1):31-42), the HLA-G promoter is induced by arsenite, hsp promoters can be activated by photodynamic therapy (Luna et al. (2000) Cancer Res 60(6): 1637-1 644). A suitable promoter can incorporate factors such as tissue-specific activation. For example, hsp70 is transcriptionally impaired in stressed neuroblastoma cells (Drujan & De Maio (1999) 12(6):443-448). The mortalin promoter, which is up-regulated in human brain tumors (Takano et al. (1997) Exp Cell Res 237(1):38-45). A promoter employed in methods of the present invention can show selective up-regulation in tumor cells as described, for example, for mortalin (Takano et al. (1997) Exp Cell Res 237(1):38-45), hsp27 and calreticulin (Szewczenko-Pawlikowski et al. (1997) Mol Cell Biochem 177(1-2): 145-1 52; Yu et al. (2000) Electrophoresis 2 1(14): 3058-3068), grp94 and grp78 (Gazit al. (1999) Breast Cancer Res Treat 54(2): 135-146), hsp27, hsp70, hsp73, and hsp90 (Cardillo et al. (2000) Anticancer Res 20(6B):4579-4583; Strik et al. (2000) Anticancer Res 20(6B):4457-4552).

C. Tissue-Specific Promoters

In certain aspects to the invention, the tissue-specific nature of control is utilized at the level of control of the first repressor protein and/or the second repressor agent, such as by the level of control of the expression of the RNAi agent of the nucleic acid construct is tightly controlled in specific tissue types. Use of tissue-specific promoters therefore provides an additional level of control of expression of the RNAi, such that, for example RNAi is not expressed in certain tissues, such that the heterlogeous target gene expression is limited to the desired and specific tissue. For instance, where the expression of the first repressor protein is operatively linked to a tissue-specific promoter, expression of the first repressor protein (i.e. Tet$^R$) occurs only in the tissues in which the tissue specific promoter is active, thus RNAi is also not expressed in those tissues and does not gene silence the heterologous target gene. Alternatively, where the tissue specific promoter is not active, the Tet$^R$ is not expressed, resulting in expression of the RNAi and gene silencing of the heterologous target gene in tissues the tissue-specific promoter is not active.

In some embodiments, it may be important to employ a promoter that effectively directs the expression of the repressor proteins in the cell type, organelle, and organism chosen for expression. Those of skill in the art of molecular biology generally know the use of promoters and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous. In certain embodiments, the promoters employed in the present invention are tissue-specific promoters.

Various promoters are currently used in the art to express sequences in animal, mammalian or human organism. Most of them are lacking tissue-specificity and can be advantageously combined with the teaching provided herein. For example the promoter may be selected from group consisting of the perbB2 promoter, whey acidic protein promoter, stromelysin 3 promoter, prostate specific antigen promoter, probasin promoter.

In some embodiments, other tissue specific promoters include, for example but are not limited to such as albumin (liver specific, Pinkert et al., (1987)), lymphoid specific promoters (Calame and Eaton, 1988), in particular promoters of T-cell receptors (Winoto and Baltimore, (1989)) and immunoglobulins; Banerji et al., (1983); Queen and Baltimore, 1983), neuron specific promoters (e.g. the neurofilament promoter; Byrne and Ruddle, 1989), pancreas specific promoters (Edlund et al., (1985)) or mammary gland specific promoters (milk whey promoter, U.S. Pat. No. 4,873,316 and European Application Publication No. 264,166) as well as developmentally regulated promoters such as the murine hox promoters (Kessel and Cruss, Science 249:374-379 (1990)) or the α-fetoprotein promoter (Campes and Tilghman, Genes Dev. 3:537-546 (1989)), the contents of each of which are fully incorporated by reference herein. Preferably, the promoter is constitutive in the respective cell types.

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), DIA dopamine receptor gene (Lee, et al., 1997), insulin-like growth factor II (Wu et al., 1997), human platelet endothelial cell adhesion molecule-1 (Almendro et al., 1996), and the SM22.alpha. promoter. Tissue-specific promoters and/or regulatory elements will be useful in certain embodiments. Other examples of such tissue-specific promoters that may be used with the expression vectors of the invention include promoters from the liver fatty acid binding (FAB) protein gene, specific for colon epithelial cells; the insulin gene, specific for pancreatic cells; the transphyretin, .alpha.1-antitrypsin, plasminogen activator inhibitor type 1 (PAI-1), apolipoprotein AI and LDL receptor genes, specific for liver cells; the myelin basic protein (MBP) gene, specific for oligodendrocytes; the glial fibrillary acidic protein (GFAP) gene, specific for glial cells; OPSIN, specific for targeting to the eye; and the neural-specific enolase (NSE) promoter that is specific for nerve cells.

Also contemplated as useful in the present invention are the dectin-1 and dectin-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest. Alternatively, a tissue-specific promoter for gene therapy such as cancer gene therapy, may be employed in the present invention.

Examples of tissue-specific promoters include, but are not limited to, the promoter for creatine kinase, which has been used to direct expression in muscle and cardiac tissue and immunoglobulin heavy or light chain promoters for expression in B cells. Other tissue specific promoters include the human smooth muscle alpha-actin promoter. Exemplary tissue-specific expression elements for the liver include but are not limited to HMG-COA reductase promoter, sterol regulatory element 1, phosphoenol pyruvate carboxy kinase (PEPCK) promoter, human C-reactive protein (CRP) promoter, human glucokinase promoter, cholesterol L 7-alpha hydroylase (CYP-7) promoter, beta-galactosidase alpha-2,6 sialylkansferase promoter, insulin-like growth factor binding protein (IGFBP-1) promoter, aldolase B promoter, human transferrin promoter, and collagen type I promoter. Exemplary tissue-specific expression elements for the prostate include but are not limited to the prostatic acid phosphatase (PAP) promoter, prostatic secretory protein of 94 (PSP 94) promoter, prostate specific antigen complex promoter, and human glandular kallikrein gene promoter (hgt-1). Exemplary tissue-specific expression elements for gastric tissue include but are not limited to the human H+/K+-ATPase alpha subunit promoter. Exemplary tissue-specific expression elements for the pancreas include but are not limited to pancreatitis associated protein promoter (PAP), elastase 1 transcriptional enhancer, pancreas specific amylase and elastase enhancer promoter, and pancreatic cholesterol esterase gene promoter. Exemplary tissue-specific expression elements for the endometrium include, but are not limited to, the uteroglobin promoter. Exemplary tissue-specific expression elements for adrenal cells include, but are not limited to, cholesterol side-chain cleavage (SCC) promoter. Exemplary tissue-specific expression elements for the general nervous system include, but are not limited to, gamma-gamma enolase (neuron-specific enolase, NSE) promoter. Exemplary tissue-specific expression elements for the brain include, but are not limited to, the neurofilament heavy chain (NF—H) promoter. Exemplary tissue-specific expression elements for lymphocytes include, but are not limited to, the human CGL-1/granzyme B promoter, the terminal deoxy transferase (TdT), lambda 5, VpreB, and lck (lymphocyte specific tyrosine protein kinase p561ck) promoter, the humans CD2 promoter and its 3' transcriptional enhancer, and the human NK and T cell specific activation (NKG5) promoter. Exemplary tissue-specific expression elements for the colon include, but are not limited to, pp60c-src tyrosine kinase promoter, organ-specific neoantigens (OSNs) promoter, and colon specific antigen-P promoter.

In some embodiments, tissue-specific expression elements for breast cells are for example, but are not limited to, the human alpha-lactalbumin promoter. Exemplary tissue-specific expression elements for the lung include, but are not limited to, the cystic fibrosis transmembrane conductance regulator (CFTR) gene promoter.

Other elements aiding specificity of expression in a tissue of interest can include secretion leader sequences, enhancers, nuclear localization signals, endosmolytic peptides, etc. Preferably, these elements are derived from the tissue of interest to aid specificity. In general, the in vivo expression element shall include, as necessary, 5' non-transcribing and 5' non-translating sequences involved with the initiation of transcription. They optionally include enhancer sequences or upstream activator sequences.

C. Constitutive Promoters

Examples of such constitutive promoters useful in the nucleic acid constructs of the present invention include, for example but are not limited to the human cytomegalovirus promoter IE as taught by Boshart et al., (1985), ubiquitously expressing promoters such as HSV-Tk (McKnight et al., (1984) and β-actin promoters (e.g. the human β-actin promoter as described by Ng et al., (1985)), as well as promoters in combination with control regions allowing integration site independent expression of the transgene (Grosveld et al., (1987)).

Constitutive mammalian promoters include, but are not limited to, polymerase promoters as well as the promoters for the following genes: hypoxanthine phosphoribosyl transferase (HPTR), adenosine deaminase, pyruvate kinase, and beta.-actin. Exemplary viral promoters which function constitutively in eukaryotic cells include, but are not limited to, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. Inducible promoters are expressed in the presence of an inducing agent and include, but are not limited to, metal-inducible promoters and steroid-regulated promoters. For example, the metallothionein promoter is induced to promote transcription in the presence of certain metal ions. Other inducible promoters are known to those of ordinary skill in the art.

D. Other Genetic Control Elements

Genetic control sequences are furthermore to be understood as those permitting removal of the inserted sequences from the genome. Methods based on the cre/lox (Dale and Ow (1991) Proc Nat'l Acad Sci USA 88:10558-10562; Sauer (1998) Methods 14(4):381-92; Odell et al. (1990) Mol Gen Genet 223:369-378), FLP/FRT (Lysnik et al. (1993) NAR 2 1:969-975), or Ac/Ds system (Lawson et al. (1994) Mol Gen Genet 245:608-615; Wader et al. (1987) in TOMATO TECHNOLOGY 189-198 (Alan R. Liss, Inc.); U.S. Pat. No. 5,225, 341; Baker et al. (1987) EMBO J 6: 1547-1 554) permit a—if appropriate tissue-specific and/or inducible—removal of a specific DNA sequence from the genome of the host organism. Control sequences may in this context mean the specific flanking sequences (e.g., lox sequences), which later allow removal (e.g., by means of ere recombinase).

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Samow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

In some embodiments, the nucleic acid construct and systems as disclosed herein can further comprise multiple cloning site (MCS), which is a nucleic acid region that contains multiple restriction enzyme sites, any of which can be used in conjunction with standard recombinant technology to digest the vector. (See Carbonelli et al., 1999, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology. In some embodiments, multiple cloning sites, are useful in the nucleic acid constructs and compositions as disclosed herein for replacing one heterogonous target gene with another heterologous target gene.

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

In some embodiments, the nucleic acid construct and systems as disclosed herein can further comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the methods and nucleic acid constructs as disclosed herein include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

In expression, particularly eukaryotic expression, the nucleic acid construct and systems as disclosed herein will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

In order to propagate a vector in a host cell, the nucleic acid construct and systems as disclosed herein it can further contain one or more origins of replication sites (often termed "ori"), which is a specific nucleic acid sequence at which replication is initiated. Alternatively an autonomously replicating sequence (ARS) can be employed if the host cell is yeast.

II. RNAi Agent

A. General Properties of RNAi Agents

In some embodiments, the RNAi agent of the present invention as disclosed herein gene silences the heterologous target gene by binding to a RNAi target site located within a non-coding region of the heterologous target gene. In some embodiments, the RNAi agent is any nucleic acid agent which is capable of gene silencing. RNA interference (RNAi) molecules include, for example but are not limited to siRNA, dsRNA, stRNA, shRNA and modified versions thereof, where the RNAi silences the gene expression of target gene. In some embodiments, RNAi is an anti-sense oligonucleic acid, or a nucleic acid analogue, for example but are not limited to DNA, RNA, peptide-nucleic acid (PNA), pseudo-complementary PNA (pc-PNA), or locked nucleic acid (LNA) and the like. In alternative embodiments, a nucleic acid can be single or double stranded, and can be selected from a group comprising nucleic acid encoding proteins that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

In some embodiments single-stranded RNA (ssRNA), a form of RNA endogenously found in eukaryotic cells can be used to form an RNAi molecule. Cellular ssRNA molecules include messenger RNAs (and the progenitor pre-messenger RNAs), small nuclear RNAs, small nucleolar RNAs, transfer RNAs and ribosomal RNAs. Double-stranded RNA (dsRNA) induces a size-dependent immune response such that dsRNA larger than 30 bp activates the interferon response, while shorter dsRNAs feed into the cell's endogenous RNA interference machinery downstream of the Dicer enzyme. Methods for "gene silencing" are commonly known by persons of ordinary skill in the art.

Without being bound by theory, RNA interference (RNAi) provides a powerful approach for inhibiting the expression of selected target polypeptides. RNAi uses small interfering RNA (siRNA) duplexes that target the messenger RNA encoding the target polypeptide for selective degradation. siRNA-dependent post-transcriptional silencing of gene expression involves cutting the target messenger RNA molecule at a site guided by the siRNA.

RNA interference (RNAi) is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference is present. The decrease of the target gene can be of at least 30%, 40%, 50%, 60%, 70%, 80%, 90%, 95% or 99% or 100% or more as compared to the expression of a target gene which has not been gene silenced or targeted by an RNA interfering agent.

The term "short interfering RNA" (siRNA), also referred to herein as "small interfering RNA" are defined as agents which function to inhibit expression of a target gene, e.g., by RNAi. An siRNA can be chemically synthesized, or produced by in vitro transcription, or can be produced within a host cell, for example within the host cell comprising the nucleic acid construct of the present invention.

In some embodiments of the present invention, the RNAi agent is a siRNA, and in some embodiments the siRNA is a double stranded RNA (dsRNA) molecule of about 10 to about 40 nucleotides in length, or about 10 to about 22 nucleotides, or 10, 11, 12, 13, 14, 15, 16, 17, 18, 19, 20, 21, or 22 nucleotides in length or longer than 22 nucleotides in length, and can, in some embodiments further comprise a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the heterologous target gene messenger RNA (mRNA).

siRNAs useful in the methods as disclosed herein also include small hairpin (also called stem loop) RNAs (shRNAs). In one embodiment, these shRNAs are composed of a short (e.g., about 10 to 25, or about 19 to about 22 nucleotides) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

In some embodiments, the sequence of the RNA interfering agent for use in the compositions and methods as disclosed herein can be a sequence that is substantially homologous to the RNAi target sequence located within a non-coding region of the heterologous target gene, for example but not limited to, the RNAi target site present in the 3'UTR, 5'UTR or introns of the heterologous target gene.

As used in this context, the RNAi agent is "substantially homologous" refers to the RNAi agent sequence as being substantially identical, sufficiently complementary, or similar to the RNAi target site to effect RNA interference of the heterologous target gene. In some embodiments, the RNAi agent sequence is completely complementary to the RNAi target site sequence.

The siRNA preferably targets only one sequence. However, in some embodiments, the nucleic acid construct may comprise multiple RNAi target site in non-coding regions of the heterologous target gene to increase efficiency of gene silencing in the presence of the RNAi agent. In some embodiments, multiple RNAi target sites may be arranged sequentially, that is multiple RNAi target sites are aligned together in one region of a non-coding region of the heterologous target gene. Alternatively, in other embodiments more than one RNAi target site is located in different non-coding regions of the heterologous target gene, for instance but not by way of limitation, one RNAi target site can be in the 3'UTR and another RNAi target site can be located within the 5'UTR.

Each of the RNAi agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, according to Jackson et al. (Id.) 15, or perhaps as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

siRNA molecules need not be limited to those molecules containing only RNA, and can further comprise modifications or other chemically modified nucleotides and non-nucleotides (if such modifications can be performed in the cell), and also include molecules wherein a ribose sugar molecule is substituted for another sugar molecule or a molecule which performs a similar function. Moreover, a non-natural linkage between nucleotide residues can also be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196, which is incorporated herein by reference). Other examples include RNA molecules containing the o-linkage between the sugar and the heterocyclic base of the nucleoside, which confers nuclease resistance and tight complementary strand binding to the oligonucleotidesmolecules similar to the oligonucleotides containing 2'-O-methyl ribose, arabinose and particularly D-arabinose (U.S. Pat. No. 5,177,196, which is incorporated herein by reference).

In some embodiments, a RNAi agent can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups. Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

In some embodiments, further modifications to the RNAi as disclosed herein include siRNA modifications such as 2'-deoxy-2'-fluorouridine or locked nucleic acid (LNA) nucleotides and RNA duplexes containing either phosphodiester or varying numbers of phosphorothioate linkages. Such modifications are known to persons skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

In some embodiments, the nucleic acid sequences encoding siRNA and miRNA molecules can have various "tails" covalently attached to either their 3'- or to their 5'-ends, or to both, which are also known by persons or ordinary skill in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

siRNAs useful in the present invention for targeting the RNAi target site located within a non-coding region of the target heterologous gene and resulting in gene silencing of the target gene can be readily designed and tested. Accordingly, siRNAs useful for the methods as disclosed herein include siRNA molecules of about 10 to about 40 or about 10 to about 28 nucleotides in length, or about 19 nucleotides, which are homologous to the RNAi target site located within a non-coding region of the heterologous target gene, such as the 3'UTR, 5'UTR or introns of the heterologous target gene. Preferably, a RNAi agent such as a siRNA molecule targeting the RNAi target site located within a heterologous target gene has a length of about 10 to about 25 nucleotides, for example, 10, 11, 12, 13, 14, 15, 16, 17, 18, 19, 20, 21, 22, 23, 24, 25 nucleotides. In some embodiments, a siRNA molecule useful in the methods as disclosed herein has a length of about 19, 20, 21, or 22 nucleotides. In some embodiments, a RNAi agent such as a siRNA that targets the RNAi target site located within a heterologous target gene can also comprise a 3' hydroxyl group. In some embodiments, a RNAi molecule for use as disclose herein can be single-stranded or double stranded; can be blunt ended or comprise overhanging ends (e.g., 5', 3'). In specific embodiments, a RNAi molecule such as a siRNA molecule targeting the heterologous target gene is double stranded and either blunt ended or comprises overhanging ends.

In one embodiment, at least one strand of a RNAi molecule such as a siRNA molecule targeting the RNAi target site located within a heterologous target gene has a 3' overhang from about 0 to about 6 nucleotides (e.g., pyrimidine nucleotides, purine nucleotides) in length. In other embodiments, the 3' overhang is from about 1 to about 5 nucleotides, or from about 1 to about 3 nucleotides, or from about 2 to about 4 nucleotides in length. In another embodiment, a RNAi molecule such as a siRNA molecule targeting the RNAi target site located within a heterologous target gene is double stranded, where one strand has a 3' overhang and the other strand can be blunt-ended or have an overhang. In another embodiment, a RNAi molecule such as a siRNA molecule targeting the RNAi target site located within a heterologous target gene is double stranded and both strands comprise an overhang, the length of the overhangs can be the same or different for each strand. In a particular embodiment, a RNAi molecule for use in the system and constructs as disclosed herein comprises about 15, 16, 17, 18 19, 20, 21, or 22 nucleotides which are paired and which have overhangs of from about 1 to about 3, particularly about 2, nucleotides on both 3' ends of the RNAi molecule. In one embodiment, the 3' overhangs can be stabilized against degradation. In some embodiments, a RNAi can be stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

As disclosed herein, gene silencing of the heterologous target gene has been demonstrated targeted using RNAi agents and such siRNA, for instance using RNAi agent which targets the RNAi target site corresponding to SEQ ID NO:1 or SEQ ID NO:2 located within the 3'UTR of the heterologous target gene. In some embodiments, assessment of the expression and/or knock down of the heterologous target gene using such RNAi agents, such as siRNAs can be determined using methods commonly known by persons in the art, for example, immunoblot assays, western blots, ELISA, quantitative RT-PCR methods such as taqman or other real-time PCR methods or using commercially available kits.

In a particular embodiment, RNAi agents useful in the methods, systems and compositions as disclosed herein include sequences RNAi molecules which target synthetic sequences located within the non-coding regions of the heterologous target gene. In some embodiments, a RNAi target site for RNAi agents useful in the present invention are non-endogenous nucleic acid sequences, for example but not limited to, RNAi target sites corresponding to 5'-CTACA-CAAATCAGCGATTT-3' (SEQ ID NO: 1) which is a region of the non-endogenous β-galactosidase (β-gal) gene which corresponds to GenBank Ref: ID NM_000404 (SEQ ID NO:3); and 5'-ATACAAAGGATATCAGGTG-3' (SEQ ID NO: 2) which is a region of the non-endogenous luciferase (luc) gene.

Accordingly, any sequence from a non-endogenous gene, such as but not limited to luciferase gene or β-gal can be used to design RNAi agents, and the corresponding target RNAi target sites placed within a non-coding region of the heterologous target gene. In some embodiments, useful non-endogenous sequences to be used as RNAi target sequences can be viral genes, reporter genes, such as β-gal, luciferase, florescent proteins and the like.

To achieve gene silencing of the heterologous target gene, the RNAi agent of the invention comprises at least one ribonucleotide sequence that is substantially identical (as defined above), preferably identical, to a RNAi target sequence located within a non-coding region of the heterologous gene. Preferably, the RNAi agent sequence has substantial identity to the RNAi target site sequence, and has a length of least 15 nucleotides, preferably at about 19 nucleotides, or about 22 nucleotides. In some embodiments, the RNAi has an identity of at least 65%, at least 80%, at least 90%, at least 95%, or 100% to a sequence of at least 10, 11, 12, 13, 14, 15, 16, 17, 18, 19 or greater than 19 nucleotides of the RNAi target sequence located within a non-coding region in the heterologous target gene. In one embodiment, the RNAi agent hybridizes (under stringent conditions, such as under low stringency conditions or alternatively under high stringency conditions) to the RNAi target site located within a non-coding region in the heterologous target gene.

In one embodiment the RNAi agent is substantially identical, preferably identical, to the RNAi target site located within a part of the non-coding sequence of the heterologous target gene. The non-coding sequence can be the 5'- or 3'-untranslated sequence (5'UTR or 3'UTR) or the introns, but can also be a non-transcribed sequence. Non-endogenous sequences as RNAi target sequence are preferred RNAi agent targets, and therefore the RNAi agent is highly unlikely to result in non-specific knockdown of endogenous genes or genes in the same gene family as the heterologous target gene, where a gene family refers to different genes encoding very similar proteins.

B. Target RNAi Sequence.

In some embodiments, the RNAi agent is substantially similar to the RNAi target site sequence in the nucleic acid construct. In particular, the RNAi target sequence is located in a non-coding region of the heterologous target gene, for example the RNAi target sequence is located within the 5'UTR, 3'UTR or intron sequences.

In some embodiments, the RNAi target site is a nucleic acid sequence that is a non-endogenous nucleic acid sequence. Stated another way, the RNAi target site nucleic acid sequence corresponds to a nucleic acid sequence that is not normally present in the cell. Such a RNAi target site nucleic acid sequence that is non-endogenous is also referred to herein as a "synthetic" nucleic acid sequence. As disclosed in the examples, two exemplary RNAi target sites were used which were based on the nucleic acid sequences from a β-galactosidase gene and a luciferase gene, both of which are examples of non-endogenous nucleic acid sequences, as the sequences are not normally found in the cell in which the nucleic acid construct is to be introduced. Alternatively, regions from pathogen genes, such as viral genes can be used as non-endogenous target genes.

In some embodiments, a RNAi target site is defined as any nucleic acid sequence of approximately 10, 11, 12, 13, 14, 15, 16, 17, 18, 19, 20, 21, 22, 23, 24, or 25 nucleic acids or longer that are not normally present in the cell or organism in which the nucleic acid construct is to be introduced. It can mimic a portion of a viral sequence or some other sequence not typically present in the cell.

III. Other Components of the LTRi

A. Reporter Genes and Selectable Marker Genes

In certain embodiments of the invention, cells containing the nucleic acid construct as disclosed herein can be identified in vitro or in vivo by including a marker in the nucleic acid construct. Such markers would confer an identifiable change to the cell permitting easy identification of cells containing the expression vector and/or expressing the heterologous target gene. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Where the reporter gene is to identify cells expressing the heterologous target gene, the location of the reporter gene and/or selectable marker can be downstream (i.e. 3') of the heterologous target gene and is under the same transcriptional control of the heterologous target gene, so when the expression of the heterologous target gene occurs, expression of the reporter gene also occurs.

In further embodiments of the present invention, the nucleic acid construct can further comprise a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Reporter genes encode readily quantifiable proteins and, via their color or enzyme activity, make possible an assessment of the transformation efficacy, the site of expression or the time of expression. In some embodiments, the following genes encoding reporter proteins are useful; (Schenborn and Groskreutz (1999) MoI Biotechnol 13(1):29-44) such as the green fluorescent protein (GFP) (Haseloff et al. (1997) Proc Natl Acad Sci USA 94(6):2122-2127; Sheen et al. (1995) Plant J 8(5):777-784; Reichel et al. 1996) Proc Natl Acad Sci USA 93(12):5888-5893; Chui et al. (1996) Curr Biol 6:325-330; Leffel et al. (1997) Biotechniques. 23(5):912-8; Tian et al. (1997) Plant Cell Rep 16:267-271; WO 97/41228), chloramphenicol transferase, a luciferase (Millar et al. (1992) Plant MoI Biol Rep 10:324-414; Ow et al. (1986) Science 234:856-859), the aequorin gene (Prasher et al. (1985) Biochem Biophys Res Commun 126(3): 1259-1268), b-galactosidase, R locus gene (encoding a protein which regulates the production of anthocyanin pigments (red coloring) in plant tissue and thus makes possible the direct analysis of the promoter activity without addition of further auxiliary substances or chromogenic substrates (Dellaporta et al. (1988) In: Chromosome Structure and Function: Impact of New Concepts, 18th Stadler Genetics Symposium, 11:263-282; Ludwig et al. (1990) Science 247:449), with b-glucuronidase (GUS) being very especially preferred (Jefferson (1987b) Plant MoI. Bio. Rep., 5:387-405; Jefferson et al. (1987) EMBO J 6:3901-3907). b-glucuronidase (GUS) expression is detected by a blue color on incubation of the tissue with 5-bromo-4-chloro-3-indolyl-b-D-glucuronic acid, bacterial luciferase (LUX) expression is detected by light emission; firefly luciferase (LUC) expression is detected by light emission after incubation with luciferin; and galactosidase expression is detected by a bright blue color after the tissue was stained with 5-bromo-4-chloro-3-indolyl-b-D-galactopyranoside. Reporter genes may also be used as scorable markers as alternatives to antibiotic resistance markers. Such markers are used to detect the presence or to measure the level of expression of the heterologous target gene.

IV. Specific Application

Introducing the Nucleic Acid Construct into a Cell or Organism

Transfection is the introduction of nucleic acid construct as disclosed herein into recipient cells. Efficient transfection requires vectors, which facilitate the introduction of the nucleic acid construct into the desired cells, and in some embodiments may provide mechanisms for chromosomal integration, and provide for the appropriate expression of the traits or proteins encoded by those nucleic acids. The design and construction of efficient, reliable, and safe vectors for cell transfection is well known to the art. In the context of the present invention, any vector which can mediate the delivery and genomic integration of the nucleic acid construct as disclosed into the target cell, tissue or organism is contemplated to be within the scope of the invention.

Viruses of many types have formed the basis for vectors. Virus infection involves the introduction of the viral genome into the host cell. That property is co-opted for use as a gene delivery vehicle in viral based vectors. The viruses used are often derived from pathogenic viral species that already have many of the necessary traits and abilities to transfect cells. However, not all viruses will successfully transfect all cell types at all stages of the cell cycle. Thus, in the development of viral vectors, viral genomes are often modified to enhance their utility and effectiveness for introducing transgeneconstructs (transgenes) or other nucleic acids. At the same time, modifications may be introduced that reduce or eliminate their ability to cause disease. Thus, viral vectors derived from viruses such as retrovirus, vaccinia virus (Ridgeway, 1988; Baichwal and Sugden, 1986; Coupar et al., 1988); adeno-associated virus (AAV) (Ridgeway, 1988; Baichwal and Sugden, 1986; Hermonat and Muzycska, 1984); and herpesviruses may be employed in the present invention. They offer several attractive features for various mammalian cells (Friedmann, 1989; Ridgeway, 1988; Baichwal and Sugden, 1986; Coupar et al., 1988; Horwich et al., 1990). Other viral vectors derived from viruses such as vaccinia virus (Ridgeway, 1988; Baichwal and Sugden, 1986; Coupar et al., 1988), sindbis virus, cytomegalovirus and herpes simplex virus may also be employed.

Retroviral vectors are known to the art as useful in delivery of nucleic acid construct and siRNA expression constructs. See, for example, the text of Devroe and Silver (2002), incorporated herein by reference, which discloses that retroviruses are efficient vectors for delivery of siRNA expressing cassettes into mammalian cells. Barton and Medzhitov (2002) disclose that retroviral introduction of siRNA expression constructs results in the stable inactivation of genes in primary cells.

Lentiviruses are a subgroup of retroviruses that can infect nondividing cells owing to the karyophilic properties of their preintegration complex, which allow for its active import through the nucleopore.

Lentiviruses include members of the bovine lentivirus group, equine lentivirus group, feline lentivirus group, ovinecaprine lentivirus group and primate lentivirus group. The development of lentiviral vectors for gene therapy has been reviewed in Klimatcheva et al., (1999). The design and use of lentiviral vectors suitable for gene therapy is described, for example, in U.S. Pat. No. 6,531,123; U.S. Pat. No. 6,207,455; and U.S. Pat. No. 6,165,782 (each specifically incorporated herein by reference). Examples of lentiviruses include, but are not limited to, HIV-1, HIV-2, HIV-1/HIV-2 pseudotype, HIV-1/SIV, FIV, caprine arthritis encephalitis virus (CAEV), equine infectious anemia virus and bovine immunodeficiency virus. HIV-1 are also encompassed for use.

Lentiviral vectors offer great advantages for gene therapy. They integrate stably into chromosomes of target cells which is required for long-term expression. Also, they do not transfer viral genes therefore avoiding the problem of generating transduced cells that can be destroyed by cytotoxic T-cells. Additionally, they have a relatively large cloning capacity, allowing for clinical applicability. Furthermore, lentiviruses, in contrast to other retroviruses, are capable of transducing non-dividing cells. This is very important in the context of gene-therapy for tissues such as the hematopoietic system, the brain, liver, lungs and muscle. For example, vectors derived from HIV-1 allow efficient in vivo and ex vivo delivery, integration and stable expression of transgenes into cells such a neurons, hepatocytes, and myocytes (Blomer et al., 1997; Kafri et al., 1997; Naldini et al., 1996a; 1996b).

The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx.

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins. Lentiviral vectors are well known in the art, see Naldini et al., (1996a and 1996b); Zufferey et al., (1997); Dull et al. (1998); U.S. Pat. Nos. 6,013,516 and 5,994,136 all incorporated herein by reference. In general, these vectors are plasmid-based or virus-based, and are configured to carry the essential sequences for incorporating foreign nucleic acid, for selection and for transfer of the nucleic acid into a host cell.

Correspondingly, lentiviral vectors derived from human immunodeficiency virus type 1 (HIV-1) can mediate the efficient delivery, integration and long-term expression of transgenes into non-mitotic cells both in vitro and in vivo (Naldini et al., 1996a; Naldini et al., 1996b; Blomer et al., 1997).

In the retroviral genome, a single RNA molecule that also contains all the necessary cis-acting elements carries all the coding sequences. Biosafety of a vector production system is therefore best achieved by distributing the sequences encoding its various components over as many independent units as possible, to maximize the number of crossovers that would be required to re-create an replication competent recombinants (RCR). Lentivector particles are generated by co-expressing the virion packaging elements and the vector genome in host producer cells, e.g. 293 human embryonic kidney cells. In the case of HIV-1-based vectors, the core and enzymatic components of the virion come from HIV-1, while the envelope protein is derived from a heterologous virus, most often VSV due to the high stability and broad tropism of its G protein. The genomic complexity of HIV, where a whole set of genes encodes virulence factors essential for pathogenesis but dispensable for transferring the virus genetic cargo, substantially aids the development of clinically acceptable vector systems.

Multiply attenuated packaging systems typically now comprise only three of the nine genes of HIV-1: gag, encoding the virion main structural proteins, pol, responsible for the retrovirus-specific enzymes, and rev, which encodes a post-transcriptional regulator necessary for efficient gag and pol expression (Dull, et al., 1998). From such an extensively deleted packaging system, the parental virus cannot be reconstituted, since some 60% of its genome has been completely eliminated. In one version of an HIV-based packaging system, Gag/Pol, Rev, VSV G and the vector are produced from four separate DNA units. Also, the overlap between vector and helper sequences has been reduced to a few tens of nucleotides so that opportunities for homologous recombination are minimized.

HIV type 1 (HIV-1) based vector particles may be generated by co-expressing the virion packaging elements and the vector genome in a so-called producer cell, e.g. 293T human enbryonic kidney cells. These cells may be transiently transfected with a number of plasmids. Typically from three to four plasmids are employed, but the number may be greater depending upon the degree to which the lentiviral components are broken up into separate units. Generally, one plasmid encodes the core and enzymatic components of the virion, derived from HIV-1. This plasmid is termed the packaging plasmid. Another plasmid encodes the envelope protein(s), most commonly the G protein of vesicular stomatitis virus (VSV G) because of its high stability and broad tropism. This plasmid may be termed the envelope expression plasmid. Yet another plasmid encodes the genome to be transferred to the target cell, that is, the vector itself, and is called the transfer vector. Recombinant viruses with titers of several millions of transducing units per milliliter (TU/ml) can be generated by this technique and variants thereof. After ultra-centrifugation concentrated stocks of approximately $10^9$ TU/ml can be obtained.

The vector itself is the only genetic material transferred to the target cells. It typically comprises the transgene cassette flanked by cis-acting elements necessary for its encapsidation, reverse transcription, nuclear import and integration. As has been previously done with oncoretroviral vectors, lentiviral vectors have been made that are "self-inactivating" in that they lose the transcriptional capacity of the viral long terminal repeat (LTR) once transferred to target cells (Zufferey, et al. 1998). This modification further reduces the risk of emergence of replication competent recombinants (RCR) and avoids problems linked to promoter interference. These vectors, or their components, are known as SIN vectors or SIN containing vectors. The SIN design is described in further detail in Zufferey et al., 1998 and U.S. Pat. No. 5,994,136 both incorporated herein by reference.

Enhancing transgene expression may be required in certain embodiments, especially those that involve lentiviral constructs of the present invention with modestly active promoters. One type of post-transcriptional regulatory element (PRE) is an intron positioned within the expression cassette, which can stimulate gene expression. However, introns can be spliced out during the life cycle events of a lentivirus. Hence, if introns are used as PRE's they may have to be placed in an opposite orientation to the vector genomic transcript.

Post-transcriptional regulatory elements that do not rely on splicing events offer the advantage of not being removed during the viral life cycle. Some examples are the post-transcriptional processing element of herpes simplex virus, the post-transcriptional regulatory element of the hepatitis B virus (HPRE) and the woodchuck hepatitis virus (WPRE). Of these the WPRE is most preferred as it contains an additional cis-acting element not found in the HPRE (Donello et al., 1998). This regulatory element is positioned within the vector so as to be included in the RNA transcript of the transgene, but downstream of stop codon of the transgene translational unit. As demonstrated in the present invention and in Zufferey et al., 1999, the WPRE element is a useful tool for stimulating and enhancing gene expression of desired transgenes in the context of the lentiviral vectors. The WPRE is characterized and described in U.S. Pat. No. 6,136,597, incorporated herein by reference. As described therein, the WPRE is an RNA export element that mediates efficient transport of RNA from the nucleus to the cytoplasm. It enhances the expression of transgenes by insertion of a cis-acting nucleic acid sequence, such that the element and the transgene are contained within a single transcript. Presence of the WPRE in the sense orientation was shown to increase transgene expression by up to 7 to 10 fold. Retroviral vectors deliver sequences in the form of cDNAs instead of complete intron-containing genes as introns are generally spliced out during the sequence of events leading to the formation of the retroviral particle. Introns mediate the interaction of primary transcripts with the splicing machinery. Because the processing of RNAs by the splicing machinery facilitates their cytoplasmic export, due to a coupling between the splicing and transport machineries, cDNAs are often inefficiently expressed. Thus, the inclusion of the WPRE in a vector results in enhanced expression of transgenes.

The introduction of nucleic acid constructs into the nucleus of a cell requires importation of the nucleic acids into the nucleus through the nuclear membrane. Lentiviruses utilize an active nuclear import system, which forms the basis of their ability to replicate efficiently in non-dividing cells. This active import system relies upon a complex series of events including a specific modality for reverse transcription. In particular, in HIV-1, the central polypurine tract (cPPT), located within the pol gene, initiates synthesis of a downstream plus strand while plus strand synthesis is also initiated at the 3' polypurine tract (PPT). After strand transfer of the short DNA molecule, the upstream plus strand synthesis will initiate and proceed until the center of the genome is reached. At the central termination sequence (cTS) the HIV-1 reverse transcriptase is ejected, (released from its template), when functioning in a strand displacement mode. (Charneau, et al., 1994) The net result is a double stranded DNA molecule with a stable flap, 99 nucleotides in length at the center of the genome. This central "flap" facilitates nuclear import. (Zennou, et al., 2000).

A. Therapeutic Applications

The specificity of compounds, compositions and methods of the invention can also be harnessed by those of skill in the art for therapeutic or prophylactic uses and are suitable for the preparation of pharmaceuticals for the treatment of human and animal diseases and for the production of pharmaceuticals.

Thus, the invention further provides a method for treating or preventing a disease, disorder or malignancy or pathogen infection in a subject, for example an animal or human being, preferably a mammal. Yet another embodiment of the invention relates to a pharmaceutically preparation comprising the nucleic acid construct as disclosed herein. Preferably, a preparation useful in the method as disclosed herein gives rise to the expression of the heterologous target gene which encodes at least one protein which has a therapeutic or prophylactic effect on the target subject in a tightly controlled regulatable manner. Yet another embodiment relates to the nucleic acid construct as disclosed herein, an expression construct or expression vector for its expression for use as a pharmaceutical, preferably for the treatment of one or more human or animal diseases. Yet another embodiment relates to the use of the nucleic acid construct as disclosed herein for the preparation of a pharmaceutical, preferably for the treatment of one or more human or animal diseases.

In some embodiments, a nucleic acid construct as disclosed can be administered to animal or human being (e.g., the mammal) in a therapeutically or prophylactically effective amount (e.g., an amount sufficient for expression of the heterologous target gene, in an amount suitable to bring about the effect associated with the heterologous target gene the therapeutic protein. In some embodiments, expression of the target heterologous gene is increased by at least about 10%, preferably by at least about 30%, more preferably by at least 50% or more when the external agent is present.

A variety of disorders can be treated the methods as disclosed herein, including infections by heterologous pathogenic organisms, either extracellular or intracellular pathogens. Additionally, the compositions of this invention are useful in preventing infection with a pathogen, or preventing the occurrence of disorders caused by reactivation of a latent pathogen. These compositions are also useful for the treatment of pathogenically-induced cancers. The composition and methods of the invention are especially suitable to treat viral diseases (i.e., HIV, Hepatitis C). This especially applies for when the heterologous target gene encodes a "gene silencer."

In an alternative embodiment, the methods of the present invention encompass methods for gene therapy using the nucleic acid construct as disclosed herein, where the heterologous target gene encodes a polypeptide having a therapeutic biological activity (also referred to herein as a "therapeutic polypeptide"). In some embodiments, a heterologous target gene useful herein encodes therapeutic proteins, including but not limited to immunostimulatory molecules, tumor suppressor gene products/antigens, anti-metabolites, suicide gene products, anti-apoptotic proteins and anti-angiogenic factors. See Mackensen et al. (1997) Cytokine Growth Factor Rev 8(2): 119-128; Walther & Stein (1999) Mol Biotechnol 13(1):21-28; Kirk & Mule (2000) Hum Gene Ther 11(6):797-806; and references cited therein.

Embodiments of the present invention relate to the treatment of many disorders and diseases can be treated. Examples of diseases that can be treated by oligonucleotide compositions include: cancer, retinopathies, autoimmune diseases, inflammatory diseases (i.e., ICAM-1 related disorders, Psoriasis, Ulcerative Colitus, Crohn's disease), cardiovascular diseases (such as hypertension), diseases of the central or peripheral nervous system such as Alzheimer's disease, Parkinson's disease or multiple sclerosis, and autosomal dominant genetic disease such as Huntington's chorea.

In some embodiments, the heterologous target gene could encode a gene silencer agent, for example a RNAi agent and thus can be used for the treatment of diseases, disorders and malignancies where it is desirable to decrease the expression of a pathogenic nucleic acid or protein. For example, see U.S. Pat. No. 6,506,559; US 2002/0,173,478 A1; US 2002/0,086,356 A1; Shuey, et al., "RNAi: gene-silencing in therapeutic intervention." Drug Discov. Today 2002 Oct. 15; 7(20):1040-6; Aoki, et al., "Clin. Exp. Pharmacol. Physiol. 2003 January; 30(1-2):96-102; Cioca, et al., "RNA interference is a functional pathway with therapeutic potential in human myeloid leukemia cell lines. Cancer Gene Ther. 2003 February; 10(2): 125-33). There are numerous medical conditions for which gene silencing therapy is reported to be suitable (see, e.g., U.S. Pat. No. 5,830,653) as well as respiratory syncytial virus infection (WO 95/22,553) influenza virus (WO 94/23,028), and malignancies (WO 94/08,003). Other examples of clinical uses of antisense sequences are reviewed, e.g., in Glaser. 1996. Genetic Engineering News 16:1. Exemplary targets for cleavage by oligonucleotides include, e.g., protein kinase Ca, ICAM-1, c-raf kinase, p53, c-myb, and the bcr/abl fusion gene found in chronic myelogenous leukemia. The method of the invention can further be used to reduce or prevent the rejection response to transplant tissue (e.g., by silencing MHC proteins). A chimeric RNA that attenuates the expression of a gene in the transplant tissue that can elicit an immune response in the recipient is administered to the transplant tissue.

Also, the method according to the invention makes possible the parallel treatment of more than one disease, such as, for example, a cardiovascular disease and a disease of the central nervous system, which is not generally possible when traditional approaches are used. Such approaches are advantageous especially in the case of multiple diseases as occur frequently with advanced age. An example which may be mentioned is the parallel treatment of hypertension and, for example, Alzheimer's disease or senile dementia.

The compounds and compositions of the invention can be utilized in pharmaceutical compositions by adding an effective amount of the compound or composition to a suitable pharmaceutically acceptable diluent or carrier. Use of the oligomeric compounds and methods of the invention may also be useful prophylactically.

Cells types that can be subjected to the present invention include hematopoietic stem cells, myoblasts, hepatocytes, lymphocytes, airway epithelium, skin epithelium, islets, dopaminergic neurons, keratinocytes, and so forth. For further descriptions of cell types, genes and methods for gene therapy see e.g., Wilson et al. (1988); Armentano et al. (1990); Wolff et al. (1990); Chowdhury et al. (1991); Ferry et al. (1991); Wilson et al. (1992); Quantin et al. (1992); Dai et al. (1992); van Beusechem et al. (1992); Rosenfeld et al. (1992); Kay et al. (1992); Cristiano et al. (1993); Hwu et al. (1993); and Herz and Gerard (1993).

The disease may, for example, be a hyperproliferative disorder, such as cancer, and specific exemplary cancers include gliosarcoma, breast cancer, lung cancer, brain cancer, melanoma, prostate cancer, ovarian cancer, pancreatic cancer, liver cancer, colon cancer, cervical cancer, bladder cancer, spleen cancer, head and neck cancer, or bone cancer.

In other embodiments, the disease condition relates to hypersecretion defects, such as those associated with hypersecretion of at least one hormone. Specific examples include hypersecretion of thyroxine (such as with Graves' disease), hypersecretion of glucocorticoids (such as with Cushing's Syndrome), hypersecretion of growth hormone (such as with gigantism or acromegaly), hypersecretion of insulin, hypersecretion of mineral corticoids (such as with aldosteronism), hypersecretion of androgens (such as with Androgenital Syndrome in females), hypersecretion of estrogens (such as an increased incidence of breast and/or ovarian cancer in females and gynecomastia in males), or hypersecretion of epinephrine and/or norepinephrine. Whereas current therapies for hypersecretion defects may comprise drastic therapeutic measures, such as removal of an adrenal gland, for example, an advantage to the present invention is the ability to fine tune the hypersecretion therapy through specialized regulation in accordance with the methods and compositions described herein.

Cells useful for employing the present invention in this context include, for example, stem cells, such as embryonic stem cells, islet cells, hepatocytes, dopaminergic neurons, keratinocytes, or a mixture thereof. In a specific embodiment of the present invention, a stem cell, such as an embryonic stem cell, is modified to employ the present invention, such as by knocking down a transplantation antigen, for example beta2-microglobulin. The modified stem cell then differentiates. In a further specific embodiment, modified stem cells either before or after differentiation, or both, are transplanted.

One aspect of the present invention is a methods to treat a subject with a disease or disorder. In some embodiments, the methods comprise administering the nucleic acid construct as disclosed herein to cells of the subject, in some embodiments by means of direct administration or in alternative embodiments by means of a vector such as a viral vector. The methods further comprises administering to the cells comprising the nucleic acid construct an effective amount of an inducer agent which induces the expression of the heterologous target gene and represses the expression of the RNAi agent. In some embodiments, the cells are in vivo or present within the subject. In alternative embodiments the cells comprising the nucleic acid construct are ex vivo, and are administered to the subject, where the subject is administered an effective amount of an inducer agent which induces the expression of the heterologous target gene and represses the expression of the RNAi agent. Such an embodiment is useful for the treatment of diseases affecting the blood, such as for example leukemias and plasma-related diseases, where the cells are harvested from the subject, transfected with the nucleic acid construct as disclosed herein and re-transplanted back into the subject.

B. Transgenic Animal Applications

In additional embodiments, cells and transgenic animals can be created using any of the systems and nucleic acid constructs described above. In some embodiments, transgenic animals can be used for controlled expression of the heterogonous target gene in a tightly regulatable and conditional manner.

The methods used for generating transgenic mice are well known to one of skill in the art. For example, one may use the manual entitled "Manipulating the Mouse Embryo", 1986. See for example, Leder and Stewart, U.S. Pat. No. 4,736,866 for methods for the production of a transgenic mouse. Other examples include the following U.S. patents incorporated by reference: U.S. Pat. No. 6,025,539, relating to IL-5 transgenic mouse; U.S. Pat. No. 6,023,010, Transgenic non-human animals depleted in a mature lymphocytic cell-type; U.S. Pat. No. 6,018,098, In vivo and in vitro model of cutaneous photoaging; U.S. Pat. No. 6,018,097, Transgenic mice expressing human insulin; U.S. Pat. No. 6,008,434, Growth differentiation factor-11 transgenic mice; U.S. Pat. No. 6,002,066; H2-M modified transgenic mice; U.S. Pat. No. 5,994,618, Growth differentiation factor-8 transgenic mice; U.S. Pat. No. 5,986,171, Method for examining neurovirulence of polio virus, U.S. Pat. No. 5,981,830, Knockout mice and their progeny with a disrupted hepsin gene; U.S. Pat. No. 5,981,829, DELTA.Nur77 transgenic mouse; U.S. Pat. No. 5,936,138; Gene encoding mutant L3T4 protein which facilitates HIV infection and transgenic mouse expressing such protein; U.S. Pat. No. 5,912,411, Mice transgenic for a tetracycline-inducible transcriptional activator; U.S. Pat. No. 5,894,078, Transgenic mouse expressing C-100 app (each specifically incorporated herein by reference).

It is well known by people of ordinary skill in the art that it is possible to carry out the genetic transformation of a zygote (and the embryo and mature organism which result therefrom) by placing or inserting exogenous genetic material into the nucleus of the zygote or to any nucleic genetic material which ultimately forms a part of the nucleus of the zygote. The genotype of the zygote and the organism which results from a zygote will include the genotype of the exogenous genetic material. Additionally, the inclusion of exogenous genetic material in the zygote results in a phenotype expression of the exogenous genetic material.

The genotype of the exogenous genetic material is expressed upon the cellular division of the zygote. However, the phenotype expression, e.g., the production of a protein product or products of the exogenous genetic material, or alterations of the zygote's or organism's natural phenotype, will occur at that point of the zygote's or organism's development during which the particular exogenous genetic material is active. Alterations of the expression of the phenotype include an enhancement or diminution in the expression of a phenotype or an alteration in the promotion and/or control of a phenotype, including the addition of a new promoter and/or controller or supplementation of an existing promoter and/or controller of the phenotype.

The genetic transformation of various types of organisms is disclosed and described in detail in U.S. Pat. No. 4,873,191, which is incorporated herein by reference.

Genetic transformation of organisms or transgenic animals can be used for in vivo analysis of gene expression during differentiation and in the elimination or diminution of genetic diseases by either gene therapy or by using a transgenic non-human mammal as a model system of a human disease.

In some embodiments, transgenic animals can be used to test putative drugs for their potential therapeutic value in humans.

In some embodiments, the exogenous genetic material can be placed in the nucleus of a mature egg. It is preferred that the egg be in a fertilized or activated (by parthenogenesis) state. After the addition of the exogenous genetic material, a complementary haploid set of chromosomes (e.g., a sperm cell or polar body) is added to enable the formation of a zygote. The zygote is allowed to develop into an organism such as by implanting it in a pseudopregnant female. The resulting organism is analyzed for the integration of the exogenous genetic material. If positive integration is determined, the organism can be used for the in vivo analysis of the gene expression, which expression is believed to be related to a particular genetic disease.

Attempts have been made to study a number of different types of genetic diseases utilizing such transgenic animals. See, for example, WO89/06689 and WO89/06693 relating to the study of Alzheimer's disease which are incorporated herein by reference.

Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (Brinster, et al., 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes.

Retroviral infection can also be used to introduce transgene into a non-human animal. The developing non-human embryo can be cultured in vitro to the blastocyst stage. During this time, the blastomeres can be targets for retroviral infection (Jaenich, 1976). Efficient infection of the blastomeres is obtained by enzymatic treatment to remove the zona pellucida (Hogan, et al., 1986). The viral vector system used to introduce the transgene is typically a replication-defective retrovirus carrying the transgene, Jahner, et al. (1985); Van der Putten, et al. (1985). Transfection is easily and efficiently obtained by culturing the blastomeres on a monolayer of virus-producing cells (Van der Putten, supra; Stewart, et al., 1987). Alternatively, infection can be performed at a later stage. Virus or virus-producing cells can be injected into the blastocoele (Jahner, 1982). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner, 1982).

A third type of target cell for transgene introduction is the embryonal stem cell (ES). ES cells are obtained from pre-implantation embryos cultured in vitro and fused with embryos (Evans et al., 1981; Bradley et al., 1984; Gossler et al., 1986; Robertson et al., 1986). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, (1988.)

As used herein, a "transgene" is a DNA sequence introduced into the germline of a non-human animal by way of human intervention such as by way of the above described methods.

It is contemplated that mammalian cells comprising the nucleic acid construct as disclosed herein includes undifferentiated cells, such as an oocyte or fertilized oocyte. These cells can be used to create a transgenic animal using techniques that are known to those of skill in the art. Therefore, in some embodiments, the present invention also includes transgenic animals that comprise cells that are capable of tight control of the heterologous target gene by the systems and nucleic acid constructs as described herein. It is specifically contemplated that a founder cell line or animal can be created for use with the non-limiting exemplary LTRi system as disclosed herein. Thus, the invention covers cells and transgenic animals that comprise the nucleic acid construct and system that conditionally expresses the heterologous target gene in a tight controlled manner. In particular embodiments, a transgenic animal has one or more cells comprising a nucleic acid construct as disclosed herein.

A founder cell or cell line can be used for introduction of a nucleic acid sequence as disclosed herein. Alternatively, a founder transgenic animal can be used to create an animal that is a knockout animal. For example, but not limited to, a founder transgenic animal with a LTRi system encoding cre recombinase (Cre) as the heterologous target gene is crossed with a transgenic animal comprising LoxP sequences flanking the gene to be knocked out, thus resulting in a conditional knockout animals by administration of the external inducer agent to the progeny. Methods for such genetic breeding schemes are well known to those of skill in the art, including by mating a founder transgenic animal (comprising the LTRi-cre nucleic acid as disclosed herein) with an effector transgenic animal (animal whose cells contain an LoxP polynucleotide), or by introducing the LTRi-cre nucleic acid construct into a transgenic cell or animal which comprises a nucleic acid sequence of 2 LoxP sites flanking gene to be knock-out.

In some embodiments, constructs described herein can be used to transfect or infect sex cells, stem cells, or any other undifferentiated cell type that can be used to create transgenic animals.

In some embodiments, the present invention further contemplates conditional transgenic or knockdown animals, such as those produced using recombination methods. Bacteriophage P1 Cre recombinase and flp recombinase from yeast plasmids are two non-limiting examples of site-specific DNA recombinase enzymes which cleave DNA at specific target sites (lox P sites for cre recombinase and frt sites for flp recombinase) and catalyze a ligation of this DNA to a second cleaved site. A large number of suitable alternative site-specific recombinases have been described, and their genes can be used in accordance with the method of the present invention. Such recombinases include the Int recombinase of bacteriophage .lambda. (with or without X is) (Weisberg et. al., 1983), herein incorporated by reference); TpnI and the .beta.-lactamase transposons (Mercier et al., 1990); the Tn3 resolvase (Flanagan and Fennewald, 1989; Stark et al., 1989); the yeast recombinases (Matsuzaki et al., 1990); the B. subtilis SpoIVC recombinase (Sato et al., 1990); the Flp recombinase (Schwartz and Sadowski, 1989; Parsons et al., 1990; Golic and Lindquist, 1989; Amin et al., 1990); the Hin recombinase (Glasgow et al., 1989); immunoglobulin recombinases (Malynn et al., 1988); and the Cin recombinase (Haffter and Bickle, 1988; Hubner et al., 1989), all herein incorporated by reference. Such systems are discussed (Echols, 1990; de Villartay, 1988; Craig, 1988; Poyart-Salmeron et al., 1989; Hunger-Bertling et al., 1990; and Cregg and Madden, 1989), all herein incorporated by reference.

In one aspect of the present invention relates to a transgenic animals comprising the nucleic acid construct as disclosed herein where the heterologous target gene is cre recombinase (Cre) or a variant or fragment thereof. Cre has been purified to homogeneity, and its reaction with the loxP site has been extensively characterized (Abremski and Hess, 1984), herein incorporated by reference). Cre protein has a molecular weight of 35,000 and can be obtained commercially from New England Nuclear/DuPont. The cre gene (which encodes the Cre protein) has been cloned and expressed (Abremski et al., 1983), herein incorporated by reference). The Cre protein mediates recombination between two loxP sequences (Sternberg et al., 1981), which may be present on the same or different DNA molecule. Because the internal spacer sequence of the loxP site is asymmetrical, two loxP sites can exhibit directionality relative to one another (Hoess and Abremski, 1984). Thus, when two sites on the same DNA molecule are in a directly repeated orientation, Cre will excise the DNA between the sites (Abremski et al., 1983). However, if the sites are inverted with respect to each other, the DNA between them is not excised after recombination but is simply inverted. Thus, a circular DNA molecule having two loxP sites in direct orientation will recombine to produce two smaller circles, whereas circular molecules having two loxP sites in an inverted orientation simply invert the DNA sequences flanked by the loxP sites. In addition, recombinase action can result in reciprocal exchange of regions distal to the target site when targets are present on separate DNA molecules.

Recombinases have important application for characterizing gene function in knockout models. In some embodiments, constructs described herein, such as the LTRi-cre can be used for targeted gene disruption in a tight, controllable and inducible manner.

Accordingly, the methods as disclosed herein are useful for generating double transgenic conditional knockout animals. For instance, a transgenic animal comprising the nucleic acid construct disclosed herein, for example, a LTRi-cre nucleic acid construct as disclosed herein can be mated with a transgenic animal comprising a nucleic acid construct with two LoxP sites flanking the gene of interest to be knocked out. Administration of the external applied inducer agent, such as IPTG to the double transgenic mice results in the expression of the Cre and subsequent gene knockout.

C. Applications to Study Biological Processes and Threshold of Biomolecules

In some embodiments of the invention, a mammalian cell in which nucleic acid constructs as disclosed herein can be introduced into it by means well known to those of skill in the art.

In further embodiments of the invention, the mammalian cell contains a certain nucleic acid construct(s).

The methods and compositions of the invention can be used alone or in combination to stimulate or inhibit expression of specific genes in animals to mimic the pathophysiology of human disease, thereby creating animal models of human disease. For example, in a host animal comprises the nucleic acid construct as disclosed herein that controls the expression of a heterologous target gene believed to be involved in a disease or disorder. Such an animal can be, in exemplary embodiments mated to a second animal carrying one or more transgenes. Alternatively, a host animal comprises a LTRi that controls the expression of Cre which can be mated with transgenic animals with genes flanked by LoxP sites. Accordingly, the level or dose of IPTG administered to the host animal or cell that comprises the nucleic acid constructs as disclosed herein can be used to examine the relationship between the level of the heterologous target gene expression and the disease, or in some instances the threshold level of heterologous target gene expression to result in a biological effect.

Accordingly, the methods as disclosed herein are highly advantageous over conventional inducible gene expression systems in that no basal expression of the heterologous target gene occurs, due to the tet-regulated RNAi expression, although heterologous target gene expression can be highly induced on addition of an extracellular inducer agent such as IPTG. In particular, both the levels of the expression and timing of heterologous target gene expression can be controlled by the level of the extracellular inducer agent such as IPTG.

D. Methods to Measure Transgene Expression

Modulation of gene expression may be effected by affecting transcriptional initiation, transcript stability, translation of the transcript into protein product, protein stability, or a combination thereof. Quantitative effects can be measured by techniques such as in vitro transcription, in vitro translation, Northern hybridization, nucleic acid hybridization, reverse transcription-polymerase chain reaction (RT-PCR), run-on transcription, Southern hybridization, cell surface protein labeling, metabolic protein labeling, antibody binding, immunoprecipitation (IP), enzyme linked immunosorbent assay (ELISA), electrophoretic mobility shift assay (EMSA), radioimmunoassay (RIA), fluorescent or histochemical staining, microscopy and digital image analysis, and fluorescence activated cell analysis or sorting (FACS).

Gene expression can be assayed by use of a reporter or selectable marker gene whose protein product is easily assayed. Reporter genes include, for example, alkaline phosphatase, .beta.-galactosidase (LacZ), chloramphenicol acetyltransferase (CAT), .beta.-glucoronidase (GUS), bacterial/insect/marine invertebrate luciferases (LUC), green and red fluorescent proteins (GFP and RFP, respectively), horseradish peroxidase (HRP), β-lactamase, and derivatives thereof (e.g., blue EBFP, cyan ECFP, yellow-green EYFP, destabilized GFP variants, stabilized GFP variants, or fusion variants sold as LIVING COLORS fluorescent proteins by Clontech). Such reporter genes would use cognate substrates that are preferably assayed by a chromogen, fluorescent, or luminescent signal. Alternatively, assay product may be tagged with a heterologous epitope (e.g., FLAG, MYC, SV40 T antigen, glutathione transferase, hexahistidine, maltose binding protein) for which cognate antibodies or affinity resins are available. Examples of drugs for which selectable marker genes exist are ampicillin, geneticin (G418)/kanamycin/neomycin, hygromycin, puromycin, and tetracycline. An enzyme (e.g., diphtheria toxin, dihydrofolate reductase, HSV-1 thymidine kinase) may be used as a selectable marker in sensitive host cells or auxotrophs. For example, diphtheria toxin can be used to ablate cell in lineage mapping; stepped increasing concentrations of methotrexate can increase the copy number of an expression vector linked to a DHFR selectable marker by gene amplification; gancyclovir can negatively select for a viral thymidine kinase selectable marker.

Techniques for measuring transcriptional or translational activity in vivo are known in the art. For example, a nuclear run-on assay may be employed to measure transcription of a reporter gene. The translation of the reporter gene may be measured by determining the activity of the translation product. The activity of a reporter gene can be measured by determining one or more of the abundance of transcription of polynucleotide product (e.g., RT-PCR of GFP transcripts), translation of polypeptide product (e.g., immunoassay of GFP protein), and enzymatic activity of the reporter protein per se (e.g., fluorescence of GFP or energy transfer thereof).

V. Pharmaceutical Compositions and Methods

A. The amount of an expression vector administered to a mammalian cell or non-human mammal by transfection or transgenesis techniques, respectively, according to the invention is an amount effective to introduce the expression vector into host cells or non-germline tissues on a transient or stable basis (e.g., the expression vector can be detected in such cells or tissues at least one week after ceasing its administration). The vector can be maintained as an episome or may be integrated into a host chromosome. Thus, the term "effective amount" refers to that amount of composition necessary to achieve the indicated effect.

Pharmaceutical compositions that are useful in the methods of the invention may be administered in solid or liquid (especially to stabilize nucleic acids for storage and transportation), ophthalmic, suppository, aerosol, prolonged release, or other formulations. In addition to the expression vector, such compositions may contain pharmaceutically-acceptable carriers and vehicles, buffers, excipients, salts, stabilizers, preservatives, and other ingredients that enhance and facilitate drug administration. The composition may include such components, for example, as the following: nanospheres, microspheres, liposomes, defective or replicatively competent viral particles, chemical transfecting agents that condense nucleic acids, and a member of the antibody/antigen, receptor/ligand (e.g., transferrin, galactosylated peptide), or other specific binding pairs that directs introduction of the expression vector to a target cell or tissue in preference to other cells or tissues.

Production of gene and cell products according to the present regulation will be regulated for good laboratory practices (GLP) and good manufacturing practices (GMP) by governmental agencies (e.g., U.S. Food and Drug Administration). This requires accurate and complete record keeping, as well as monitoring of QA/QC. Oversight of patient protocols by agencies and institutional panels is also envisioned to ensure that informed consent is obtained; the safety, bioactivity, appropriate dosage, and efficacy of products are studied in phases; results are statistically significant; and ethical guidelines are followed. Similar oversight of protocols using animal models, as well as the use of toxic chemicals, and compliance with regulations is required.

Another aspect of the invention is the use of expression vectors in applications such as, for example, gene therapy (e.g., therapeutic or prophylactic), production of recombinant biologicals, genetic diagnosis, drug screening, and genetic research (e.g., genomics, proteomics, in vivo and in vitro models of human disease).

The present invention may be used alone, or as an adjunct to standard medical or surgical treatments. "Treatment" as used herein refers to: reducing or alleviating the severity of symptoms in a mammal; lessening the number of symptoms; preventing symptoms from worsening or progressing; suppressing or eliminating infectious agents, autoimmune cells, and cancerous cells; preventing an infection or disease in a patient who is free therefrom; or combinations thereof. Treatment of cardiac disease, for example, may include reduction or prevention of ischemic damage, inhibition of restenosis, neutralization of other pathological effects of heart or vascular disease, diagnosis hypoxia, or combinations thereof.

In particular, at least six clinical trials are currently ongoing in which angiogenic growth factors, including VEGF and FGF genes, are being delivered with plasmid and adenovirus vectors to patients with ischemic heart disease and critical limb ischemia (see Genetic Engineering News Vol. 18, Number 17, October 1998; Cardiology Today, Vol 3, Number 1, January 2000). The goal is to stimulate angiogenesis and collateral vessel growth to treat ischemia. But these trials did not disclose the solution provided by the present invention to the problem of tightly regulating gene expression in the target tissue (Prentice and Webster, 1995; Webster, 1999ab; Alexander et al., 1999). Instead, constitutively active CMV promoters were used so the procedures are not sufficiently effective because of expression of the growth factor in other tissues. In the present invention, however, VEGF can be delivered to ischemic heart or limb muscles using conditionally silenced-hypoxia inducible expression vectors. Using the present invention, expression of VEGF could be carefully controlled at a high level of induced activity in ischemic tissue (Lee et al., 2000), thereby confining angiogenesis to the target tissue and providing a safer and more effective treatment.

The amount of the composition which is administered to the patient is preferably an amount that does not induce any deleterious effects which outweigh the advantages which accompany its administration. Thus, treatment is preferably performed under supervision of a trained physician or with careful monitoring by a veterinarian.

Compositions of the present invention may be administered by any known route (e.g., enteral, parenteral, topical). Parenteral routes include intraarterial, intrabronchial, intramuscular, intrathecal, intravenous, subcutaneous or subdermal, transmucosal, and other injection or infusion techniques, without limitation. For example, compositions may be administered orally, parenterally, topically, regionally, or systemically.

Actual dosage levels of active ingredients in compositions may be varied so as to administer an amount of the expression vector that is effective to achieve the desired therapeutic or prophylactic effect in a particular patient. Thus, the selected dose will depend on the silencer-inducer ratio, choice of the downstream expressed region and its function, the size of the expression vector, the route of administration, the severity of the condition being treated, and the condition and prior medical history of the patient being treated.

It is also within the skill of the art, however, to start doses at levels lower than required to achieve the desired therapeutic or prophylactic effect and to gradually increase the dosage until the desired effect is achieved. These compositions may be administered according to the methods of the invention in a single dose (e.g., to treat acute disease or for stable transfection) or in multiple doses which are administered at different times (e.g., to treat chronic disease or for transient transfection). A dose of the composition may be repetitively administered to a patient (e.g., every few days to every few years), whereby gene expression is conditionally silenced and inducible after the initial treatment and then boosted by subsequent treatments.

But it would be understood as well that the specific dose for any particular patient will depend on a variety of factors, including body weight, gender, age, general health, diet, time and route of administration, combination with other drugs and patient treatments, and severity of the disease being treated. Unlike most active ingredients of pharmaceutical compositions, the range of effective amounts of expression vector would be low when the expression vector persists because it is replicated during cell division or maintained in the cell. Of course, the amount of the expression vector that is administered may be dependent upon other components of the composition and numerous factors understood by a person skilled in the art.

DNA is transcribed to produce an RNA transcript corresponding to the DNA, the RNA is translated to produce a nascent chain, and post-translationally processed (e.g., acetylation, acylation, amidation, disulfide bonding, glycosylation, phosphorylation, hydroxylation of .gamma.-carboxyglutamic acid, methylation, phosphorylation, proteolysis, sulfatation) and folded. All of nascent chain, folded protein, and post-translationally processed protein are generically called polypeptide.

Gene activation may be achieved by inducing an expression vector containing a downstream region related to the host gene (e.g., the entire coding region or functional portions of the host gene, hypermorphic mutant versions thereof) or unrelated to the host gene that acts to relieve suppression of gene activation (e.g., at least partially inhibiting expression of a negative regulator of the host gene such as a soluble cytokine receptor). Overexpression of transcription or translation, as well as overexpressing protein function, is a more direct approach to gene activation. Alternatively, the down-stream expressed region may direct homologous recombination into a locus in the genome and thereby replace an endogenous transcriptional regulatory region of the host gene with the silencer-inducible region of the expression vector.

An expression vector may be introduced into the host mammalian cell or non-human mammal by a transfection or transgenesis technique using, for example, chemicals (e.g., calcium phosphate, DEAE-dextran, lipids, polymers), electroporation, naked DNA technology, microinjection, or viral infection; preferably, the introduced expression vector integrates into the host genome of the mammalian cell or non-human mammal. Many neutral and charged lipids, sterols, and other phospholipids to make lipid carrier vehicles are known. For example, neutral lipids are dioleoyl phosphatidylcholine (DOPC) and dioleoyl phosphatidyl ethanolamine (DOPE); an anionic lipid is dioleoyl phosphatidyl serine (DOPS); and cationic lipids are dioleoyl trimethyl ammonium propane (DOTAP), dioctadecyldiamidoglycyl spermine (DOGS), dioleoyl trimethyl ammonium (DOTMA), and 1,3-di-oleoyloxy-2-(6-carboxy-spermyl)-propyl-amide tetra-acetate (DOSPER). Dipalmitoyl phosphatidylcholine (DPPC) can be incorporated to improve the efficacy and/or stability of delivery. FUGENE 6, LIPOFECTAMINE, LIPOFECTIN, DMRIE-C, TRANSFECTAM, CELLFECTIN, PFX-1, PFX-2, PFX-3, PFX4, PFX-5, PFX-6, PFX-7, PFX-8, TRANSFAST, TFX-10, TFX-20, TFX-50, and LIPOTAXI lipids are proprietary formulations. The polymer may be polyethylene glycol (PEG) or polyethylenimine (PEI); alternatively, polymeric materials can be formed into nanospheres or microspheres. Naked DNA technology delivers the expression vector in plasmid form to a cell, where the plasmid may or may not become integrated into the host genome, without using chemical transfecting agents (e.g., lipids, polymers) to condense the expression vector prior to introduction into the cell.

Thus, a mammalian cell may be transfected with an expression vector; also provided are transgenic non-human mammals. In the previously discussed alternative, a homologous region from a host gene can be used to direct integration of the silencer-inducible region to a particular genetic locus in the host genome and thereby regulate expression of the host gene at that locus. Polypeptide may be produced in vitro by culturing transfected cells; in vivo by transgenesis; and ex vivo by introducing the expression vector into allogeneic, autologous, histocompatible, or xenogeneic cells and then transplanting the transfected cells into a host organism. Special harvesting and culturing protocols will be needed for transfection and subsequent transplantation of host stem cells into a host mammal. Immunosuppression of the host mammal post-transplant and encapsulation of the host cells may be necessary to prevent rejection.

The expression vector may be used to replace function of an absent or totally defective host gene, supplement function of a partially defective host gene, or compete with activity of the host gene. Thus, the cognate gene of the host may be neomorphic, hypomorphic, hypermorphic, or normal. Replacement or supplementation of function can be accomplished by the methods discussed above, and transfected mammalian cells or transgenic non-human mammals may be selected for high expression (e.g., assessing amount of transcribed or translated produce, or physiological function of either product) of the downstream region. But competition between the expressed downstream region and a neomorphic, hypermorphic, or normal host gene may be more difficult to achieve unless the encoded polypeptides are multiple subunits that form into a polymeric protein complex. Alternatively, a negative regulator or a single-chain antibody that inhibits function intracellularly may be encoded by the downstream region of the expression vector. Therefore, at least partial inhibition of functional host genes may require using antisense, RNA interference, or ribozyme technology in which the expression vector contains a downstream region corresponding to the unmodified antisense transcript, either or both strands of a dsRNA or a ribozyme, respectively.

Antisense polynucleotides were initially believed to directly block translation by hybridizing to mRNA transcripts, but is now thought to involve degradation of mRNA transcripts of a viral or cellular gene. The antisense molecule may be made using at least one functional portion of a gene in the antisense orientation as downstream expressed region in the expression vector.

B. Diseases and Disorders to be Treated by Compositions and Methods of the Present Invention Any disease may be treated with the present invention if the genetic basis and an inducer associated with the disease are known (e.g., inflammation and other stress conditions, ischemia and other hypoxic conditions, fluctuation of glucose concentration or other metabolic disorders).

Genetic vaccination may be used to provide a model of human disease or for immunomodulation in an afflicted patient (e.g., induction, stimulation, potentiation, or suppression of the immune response) by expressing or inhibiting the expression of allergens, autoantigens, antigens of infectious agents (e.g., cell surface or virus capsid/coat antigens), and tumor antigens. See U.S. Pat. Nos. 5,580,859, 5,589,466, 5,697,901, 5,804,566, 5,830,877, 5,849,719, 5,985,847, and WO 98/20734. Antibody directed against the antigen may also be produced for diagnostic, therapeutic, or prophylactic use. Thus, a downstream region may encode an immunogenic portion of one or more such antigens as single or multivalent epitopes. It is preferred that the antigen be expressed as a fusion protein with a cytokine that acts as an adjuvant (e.g., IFN-γ, GM-CSF).

Tissues which may be targeted include the nervous system (e.g., brain, eye, glia, central and peripheral nerves); the reticuloendothelial system (e.g., blood, bone marrow, dendritic cells, erythroid cells, granulocytes, lymph vasculature endothelium, lymphocytes, megakaryocytes and platelets, monocytes and macrophages, myeloid cells, neutrophils, spleen, thymus); the endocrine, reproductive, and urinary systems (e.g., adrenal gland, breast, kidney, ovary, pituitary gland, prostate, testicle, thyroid gland, uterine endothelium);

the cardiopulmonary system (e.g., heart, lung, arterial and venous vascular endothelium); the digestive system (e.g., colon, gall bladder, large and small intestines, liver, pancreas, rectum, stomach); bone, cartilage, connective tissues, skin, smooth muscle, and striated muscle; ectodermal, endodermal, or mesodermal tissues; mesenchymal and parenchymal tissues.

(ii) Cancer

The ability to introduce the expression vector into a variety of normal cells and tissues suggests that the treatment of benign and malignant cancers (e.g., ascites and solid tumors, carcinomas, leukemias, lymphomas, melanomas, sarcomas) is possible. Some tumor types of interest are breast, colorectal, lung, ovarian, pancreatic, prostatic, renal, and testicular carcinoma.

Thus, examples of diseases that might be treated by regulated gene expression of an appropriate coding region, transcribed region in antisense orientation, dsRNA, or ribozyme, or that may provide models of such disease, are the following: acquired or inherited immunodeficiency, allergy and other immune hypersensitivities, anemia and thalassemia, autoimmune disease, hemolytic or septic shock, hemophilia, inflammation and other stress conditions, ischemia and other hypoxic conditions, carcinoma (e.g., basal cell, basosquamous, Brown-Pearce, ductal, Ehrlich tumor, in situ, Krebs, Merkel cell, small or non-small cell lung, oat cell, papillary, bronchiolar, squamous cell, transitional cell, Walker), leukemia (e.g., B-cell, T-cell, HTLV, acute or chronic lymphocytic, mast cell, myeloid), histiocytoma, histiocytosis, Hodgkin disease, non-Hodgkin lymphoma, plasmacytoma, reticuloendotheliosis, adenoma, adenocarcinoma, adeno-fibroma, adenolymphoma, ameloblastoma, angiokeratoma, angiolymphoid hyperplasia with eosinophilia, sclerosing angioma, angiomatosis, apudoma, branchioma, malignant carcinoid syndrome, carcinoid heart disease, carcinosarcoma, cementoma, cholan-gioma, cholesteatoma, chondrosarcoma, chondroblastoma, chondrosarcoma, chordoma, choristoma, craniopharyngioma, chrondroma, cylindroma, cystadenocarcinoma, cystadenoma, cystosarcoma phyllodes, dysgerminoma, ependymoma, Ewing sarcoma, fibroma, fibrosarcoma, giant cell tumor, ganglioneuroma, glioblastoma, glomangioma, granulosa cell tumor, gynandroblastoma, hamartoma, hemangioendo-thelioma, hemangioma, hemangiopericytoma, hemangiosarcoma, hepatoma, islet cell tumor, Kaposi sarcoma, leiomyoma, leiomyosarcoma, leukosarcoma, Leydig cell tumor, lipoma, liposarcoma, lymphangioma, lymphangiomyoma, lymphangiosarcoma, medulloblastoma, meningioma, mesenchymoma, mesonephroma, mesothelioma, myoblastoma, myoma, myosarcoma, myxoma, myxosarcoma, neurilemmoma, neuroma, neuroblastoma, neuroepithelioma, neurofibroma, neurofibromatosis, odontoma, osteoma, osteosarcoma, papilloma, paraganglioma, paraganglioma nonchromaffin, pinealoma, rhabdomyoma, rhabdomyosarcoma, Sertoli cell tumor, teratoma, theca cell tumor, and other diseases in which cells have become dysplastic, immortalized, or transformed.

Treatment of cancer (for example solid tumors and/or leukemias) and inherited disorders. Among conditions particularly susceptible to treatment or prophylaxis according to this invention are those conditions which are characterized by the presence of an aberrant polynucleotide sequence, the function of which is necessary to the initiation or progression of the disorder, but can be inhibited without causing harm or otherwise unduly adversely impacting the health of the organism (e.g. the mammal). Mammalian cancers which are characterized by the presence of abnormal and normal polynucleotide sequences (for details see, e.g., WO94/13793) include chronic myelogenous leukemia (CML) and acute lymphoblastic leukemia (ALL), where the abnormal sequence is a fusion of two normal genes, i.e., bcr-abl. In such cancers or diseases, such as CML, the afflicted mammal also possesses a normal copy of the polynucleotide sequence or gene, and the differences between the abnormal and normal sequences or genes are differences in nucleotide sequence. For example, for CML, the abnormal sequence is the bcr-abl fusion, while the normal sequence is bcr and abl. Thus, the method above can be employed with the heterologous target gene encoding an RNAi agent which targets the polynucleotide sequence being the sequence which spans the fusion.

A method of treatment or prophylaxis of such a cancer in a mammal comprises administering to the mammal a composition of this invention wherein the target polynucleotide is a polynucleotide sequence of an abnormal cancer-causing gene in a mammal which also possesses a normal copy of the gene, and wherein the differences between the abnormal gene and the normal gene are differences in polynucleotide sequence. The skilled worker is familiar with a large number of potential target genes for cancer therapy (for example oncogenes such as ABL1, BCL1, BCL2, BCL6, CBFA2, CBL, CSF1R, ERBA, ERBB, EBRB2, FGR, FOS, FYN, HRAS, JUN, LCK, LYN, MYB, MYC, NRAS, RET or SRC; tumor suppressor genes such as BRCA1 or BRCA2; adhesion molecules; cyclin kinases and their inhibitors). An exemplary list of potential target genes, including developmental genes, oncogenes, and enzymes, and a list of cancers that can be treated according to the present invention can be found in WO 99/32619.

In some embodiments, the nucleic acid construct as disclosed herein enables expression of a heterologous target gene specially to kill cancer cells, for example it may encode an immunotoxin molecule or encode an immunosuppression molecule.

Another embodiment of the invention provides a method for the treatment of cancer (e.g., local and metastatic breast, ovarian, or prostate cancer) comprising: administration to the patient expression construct or vector (or a variant thereof) as disclosed herein containing a cytotoxic gene.

Angiogenesis and suppressed immune response play a central role in the pathogenesis of malignant disease and tumor growth, invasion, and metastasis. Thus, preferably, the heterologous target gene encodes a therapeutic polypeptide which as an ability to induce an immune response and/or an anti-angiogenic response in vivo. In one embodiment, a method encompasses use of the nucleic acid construct for gene therapy, to where the heterogeneous target gene encodes a therapeutic gene that displays both immunostimulatory and anti-angiogenic activities, for example, IL12 (see Dias et al. (1998) Int J Cancer 75(1): 151-157, and references cited herein below), interferon-alpha (O'Byrne et al. (2000) Eur J Cancer 36(2): 151-169, and references cited therein), or a chemokine (Nomura & Hasegawa (2000) Anticancer Res 20(6A):4073-4080, and references cited therein).

In another embodiment, a gene therapy construct of the present invention encodes a gene product with immunostimulatory activity and a gene product having anti-angiogenic activity. See, e.g. Narvaiza et al. (2000) J Immunol 164:31 12-3122. In another embodiment, the invention comprises a gene therapy construct encoding an IL2 polypeptide. IL12 is an immunostimulatory molecule that shows therapeutic activity in a variety of cancers, including renal cancer, breast cancer, bladder cancer, and malignant melanoma. The anti-tumor activity of IL2 is related to its capacity to expand and activate NK cells and T cells that express IL2 receptors. See, e.g., Margolin (2000) Semin Oncol 27(2): 194-203; Gore (1996) Cancer Biother Radiopharm 11 (5):281-283; Deshmukh et al. (2001) J Neurosurgery 94(2):287-292; Larchian et al. (2000) Clin Cancer Res 6(7):291 3-2920; Horiguchi et al. (2000) Gene Ther 7(10):844-851; and references cited therein. IL2 has also been used successfully when co-administered with anti-tumor vaccines. See Overwijk et al. (2000) Cancer J Sci Am 6 Suppl 1:S76-80, and references cited therein.

(ii) Pathogen Infections

The method according to the invention is particularly suitable for the treatment of the many diseases, disorders and malignancies, including pathogen infections.

Infection with pathogens, such as, for example, viral or bacterial diseases, in which case the chimeric RNA (or the dsRNA derived therefrom) attenuates the expression of a bacterial or viral gene. Specifically some of the more desirable viruses to treat with this method include, without limitation, viruses of the species Retrovirus, Herpesvirus, Hepadenovirus, Poxvirus, Parvovirus, Papillomavirus, and Papovavirus, espcially HIV, HBV, HSV, CMV, HPV, HTLV and EBV. The nucleic acid construct can comprise a heterologous target gene which is substantially identical to a target polynucleotide which is a virus polynucleotide sequence necessary for replication and/or pathogenesis of the virus in an infected mammalian cell. Among such target polynucleotide sequences are protein-encoding sequences for proteins necessary for the propagation of the virus, e.g., the HIV gag, env, gp41, and pol genes, the HPV6 L 1 and E2 genes, the HPV11 L 1 and E2 genes, the HPV16 E6 and E7 genes, the HPV18 E6 and E7 genes, the HBV surface antigens, the HBV core antigen, HBV reverse transcriptase, the HSV gD gene, the HSVvp16 gene, the HSV gC, gH, gl and gB genes, the HSV ICPO, ICP4 and ICP6 genes, Varicella zoster gB, gC and GH genes, and the BCR-abl chromosomal sequences, and noncoding viral polynucleotide sequences which provide regulatory functions necessary for transfer of the infection from cell to cell, e.g., the HIV LTR, and other viral promoter sequences, such as HSV vp16 promoter, HSV-ICPO promoter, HSV-ICP4, ICP6 and gD promoters, the HBV surface antigen promoter, the HBV pregenomic promoter, among others. The composition (e.g., the nucleic acid construct as disclosed herein comprising a nucleic acid sequence encoding a heterogeneous target gene) is administered with an polynucleotide uptake enhancer or facilitator and an optional pharmaceutically acceptable carrier. The amount or dosage which is administered to the mammal is effective to reduce or inhibit the function of the viral sequence in the cells of the mammal. The method can be used to treat animals (e.g., mammals) already infected with a virus in order to shut down or inhibit a viral gene function essential to virus replication and/or pathogenesis. In still another embodiment of this invention, the compositions described above can be employed in a method to prevent viral infection (e.g., in a mammal).

The compositions of this invention can also be employed for the treatment or prophylaxis of infection by a non-viral pathogen, either intracellular or extracellular. As used herein, the term "intracellular pathogen" is meant to refer to a virus, bacteria, protozoan or other pathogenic organism that, for at least part of its reproductive or life cycle, exists within a host cell and therein produces or causes to be produced, pathogenic proteins. Intracellular pathogens which infect cells which include a stage in the life cycle where they are intracellular pathogens include, without limitation, *Listeria, Chlamydia, Leishmania, Brucella, Mycobacteria, Shigella,* and as well as *Plasmodia*, e.g., the causative agent of malaria, *P. falciparum*. Extracellular pathogens are those which replicate and/or propagate outside of the mammalian cell, e.g., Gonorrhoeae, and *Borrellia*, among others. According to this embodiment, such infection by a pathogen may be treated or possibly prevented by administering to a mammalian subject, either already infected or anticipating exposure to the pathogen, with a composition as described above with an optional second agent that facilitates polynucleotide uptake in a cell, in a pharmaceutically acceptable carrier. In this case, the nucleic acid construct as disclosed herein comprising a nucleic acid sequence encoding a heterogeneous target gene for a polynucleotide sequence which is substantially identical to a target polynucleotide sequence of the pathogen that is necessary for replication and/or pathogenesis of the pathogen in an infected mammal or mammalian cell. As above, the amount of the composition administered is an amount effective to reduce or inhibit the function of the pathogenic sequence in the mammal. The dosages, timing, routes of administration and the like are as described below.

Thus one embodiment of the invention related to a method for reducing the susceptibility of host cells or host organisms to infection by pathogen, comprising introducing a chimeric RNA of the invention into said host cells or host organisms in an amount sufficient to attenuate expression of one or more genes necessary for expression by said pathogen. Preferably, the pathogen is a virus, a fungus or a nematode. Preferably, the host cell is a plant or an animal, preferably a mammalian, more preferably a human cell.

One of skill in the art, given this disclosure can readily select viral families and genera, or pathogens including prokaryotic and eukaryotic protozoan pathogens as well as multicellular parasites, for which therapeutic or prophylactic compositions according to the present invention can be made. See, e.g., the tables of such pathogens in general immunology texts and in U.S. Pat. No. 5,593,972, incorporated by reference herein.

C. Formulations and Administration

The chimeric nucleic acid construct as disclosed herein can be used and applied directly to an animal or human in need of therapy or prophylaxis or may be applied indirectly by means of an expression vector or construct.

(i) Viral Gene Therapy Vectors

The present invention also provides gene therapy constructs or vectors. The particular vector employed in accordance with the methods of the present invention is not in tended to be a limitation of the method for heat-induced expression of therapeutic genes by hyperthermia. Thus, any suitable vector for delivery of the gene therapy construct can be used.

The vector can be a viral vector or a non-viral vector. Suitable viral vectors include adenoviruses, adeno-associated viruses (AAVs), retroviruses, pseudotyped retroviruses, herpes viruses, vaccinia viruses, Semiliki forest virus, and baculoviruses. Suitable nonviral vectors comprise plasmids, water-oil emulsions, polethylene imines, dendrimers, micelles, microcapsules, liposomes, and cationic lipids. Polymeric carriers for gene therapy constructs can be used as described in Goldman et al (1997) Nat Biotechnol 15:462 and U.S. Pat. Nos. 4,551,482 and 5,714,166. Peptide carriers are described in U.S. Pat. No. 5,574,172. Where appropriate, two or more types of vectors can be used together. For example, a plasmid vector can be used in conjunction with liposomes. In some embodiments of the present invention, the nucleic acid construct as disclosed herein uses of an adenovirus, a plasmid, or a liposome, each described further herein below. As desired, vectors, especially viral vectors, can be selected to achieve integration of the nucleic acid of the construct of the invention, into the genome of the cells to be transformed or transfected. Including a ligand in the complex having affinity for a specific cellular marker can also enhance delivery of the complexes to a target in vivo. Ligands include antibodies, cell surface markers, viral peptides, and the like, which act to home the complexes to tumor vasculature or endothelial cells associated with tumor vasculature, or to tumor cells themselves. A complex can comprise a construct or a secreted therapeutic polypeptide encoded by a construct. An antibody ligand can be an antibody or antibody fragment specific towards a tumor marker such as Her2/neu (verb-b2 avian erythroblastic leukemia viral oncogene homologue 2), CEA (carcinoembryonic antigen), ferritin receptor, or a marker associated with tumor vasculature (integrins, tissue factor, or beta.-fibronectin isoform). Antibodies or other ligands can be coupled to carriers such as liposomes and viruses, as is known in the art. See, e.g., Neri et al. (1997) Nat BioTechnology 15:1271; Kirpotin et al. (1997) Biochemistry 36:66; Cheng (1996) Human Gene Therapy 7:275; Pasqualini et al. (1997) Nat Biotechnology 15:542; Park et al. (1997) Proc Am Ass Canc Res 38:342 (1997); Nabel (1997) "Vectors for Gene Therapy" in Current Protocols in Human Genetics on CDROM, John Wiley & Sons, New York, N.Y.; U.S. Pat. No. 6,071,890; and European Patent No. 0 439 095. Alternatively, pseudotyping of a retrovirus can be used to target a virus towards a particular cell (Marin et al. (1997) Mol Med Today 3:396). Viral vectors of the invention are preferably disabled, e.g. replication-deficient. That is, they lack one or more functional genes required for their replication, which prevents their uncontrolled replication in vivo and avoids undesirable side effects of viral infection. Preferably, all of the viral genome is removed except for the minimum genomic elements required to package the viral genome incorporating the therapeutic gene into the viral coat or capsid. For example, it is desirable to delete all the viral genome except the Long Terminal Repeats (LTRs) or Invented Terminal Repeats (ITRs) and a packaging signal. In the case of adenoviruses, deletions are typically made in the E1 region and optionally in one or more of the E2, E3 and/or E4 regions. In the case of retroviruses, genes required for replication, such as env and/ or gag/pol can be deleted.

Deletion of sequences can be achieved by recombinant means, for example, involving digestion with appropriate restriction enzymes, followed by religation. Replication competent self-limiting or self-destructing viral vectors can also be used. Nucleic acid constructs of the invention can be incorporated into viral genomes by any suitable means known in the art. Typically, such incorporation will be performed by ligating the construct into an appropriate restriction site in the genome of the virus. Viral genomes can then be packaged into viral coats or capsids by any suitable procedure. In particular, any suitable packaging cell line can be used to generate viral vectors of the invention. These packaging lines complement the replication-deficient viral genomes of the invention, as they include, typically incorporated into their genomes, the genes which have been deleted from the replication-deficient genome. Thus, the use of packaging lines allows viral vectors of the invention to be generated in culture. Suitable packaging lines for retroviruses include derivatives of PA317 cells, .psi.-2 cells, CRE cells, CRIP cells, E-86-GP cells, and 293GP cells. Line 293 cells can be used for adenoviruses and adeno-associated viruses.

Suitable methods for introduction of a gene therapy construct into cells include direct injection into a cell or cell mass, particle-mediated gene transfer, electroporation, DEAE-Dextran transfection, liposome-mediated transfection, viral infection, and combinations thereof. A delivery method is selected based considerations such as the vector type, the toxicity of the encoded gene, and the condition to be treated.

(iii) Formulations for Uptake for RNA and DNA

For the purpose of pharmaceutical applications, the nucleic acid construct of the present invention can be administered to a target cell. Various means for administration to subjects nucleic acid constructs as pharmaceutical active ingredient are described in the art.

As used herein "administration" refers to contacting cells (e.g., either in isolated form or comprised in an organism) with the pharmaceutical agent and can be performed in vitro or in vivo. With respect to in vivo applications, the formulations of the present invention can be administered to a subject in a variety of forms adapted to the chosen route of administration, e.g., parenterally, orally, or intraperitoneal. Parenteral administration, which is preferred, includes administration by the following routes: intravenous; intramuscular; interstitially; intraarterially; subcutaneous; intra ocular; intrasynovial; transepithelial, including transdermal; pulmonary via inhalation; ophthalmic; sublingual and buccal; topically, including ophthalmic; dermal; ocular; rectal; and nasal inhalation via insufflation. In some embodiments, pharmaceutical preparations for the various ways of administration (such as parenteral, transmucosal, transdermal, oral, or topical application) are well known in the art and for example described in US Patent Application No. 20040014956. The pharmaceutical agent of the invention may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. The chosen method of delivery will result in entry into cells. In some embodiments, the delivery methods of the nucleic acid constructs include liposomes (10-400 nm), hydrogels, controlled-release polymers, and other pharmaceutically applicable vehicles, and microinjection or electroporation (for ex vivo treatments). Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Some examples of such specialized drug delivery vehicles which fall into this category are liposomes, hydrogels, cyclodextrins, biodegradable nanocapsules, and bioadhesive microspheres. In one embodiment, in vitro treatment of cells with oligonucleotides can be used for ex vivo therapy of cells removed from a subject (e.g., for treatment of leukemia or viral infection) or for treatment of cells which did not originate in the subject, but are to be administered to the subject (e.g., to eliminate transplantation antigen expression on cells to be transplanted into a subject). In addition, in vitro treatment of cells can be used in non-therapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein.

Compositions for pharmaceutical use of this invention desirably contain the nucleic acid construct as disclosed herein, and optionally a expression construct for its production (hereinafter the "pharmaceutical agent").

Any of the pharmaceutical agents can be used alone or in conjunction with a pharmaceutically acceptable carrier and with additional optional components for pharmaceutical delivery. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Suitable pharmaceutically acceptable carriers facilitate administration of the polynucleotide compositions of this invention, but are physiologically inert and/or non harmful. Carriers may be selected by one of skill in the art. Such carriers include but are not limited to, sterile saline, phosphate, buffered saline, dextrose, sterilized water, glycerol, ethanol, lactose, sucrose, calcium phosphate, gelatin, dextran, agar, pectin, peanut oil, olive oil, sesame oil, and water and combinations thereof. Additionally, the carrier or diluent may include a time delay material, such as glycerol monostearate or glycerol distearate alone or with a wax. In addition, slow release polymer formulations can be used. The formulation should suit not only the form of the delivery agent, but also the mode of administration. Selection of an appropriate carrier in accordance with the mode of administration is routinely performed by those skilled in the art. Additional components for the carrier may include but are not limited to adjuvants, preservatives, chemical stabilizers, or other antigenic proteins. Suitable exemplary preservatives include chlorobutanol, potassium sorbate, sorbic acid, sulfur dioxide, propyl gallate, the parabens, ethyl vanillin, glycerin, phenol, and parachlorophenol. Suitable stabilizing ingredients which may be used include, for example, casamino acids, sucrose, gelatin, phenol red, N—Z amine, monopotassium diphosphate, lactose, lactalbumin hydrolysate, and dried milk. A conventional adjuvant is used to attract leukocytes or enhance an immune response. Such adjuvants include, among others, Ribi, mineral oil and water, aluminum hydroxide, Amphigen, Avridine, L121/squalene, D-lactide-polylactide/glycoside, pluronic plyois, muramyl dipeptide, killed *Bordetella*, and saponins, such as Quil A.

The pharmaceutical agent may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types. Liposomes can be prepared by any of a variety of techniques that are known in the art. See e.g., Betageri et al. (1993) Liposome Drug Delivery Systems, Technomic Publishing, Lancaster; Gregoriadis, ed. (1993) Liposome Technology, CRC Press, Boca Raton, Fla.; Janoff, ed. (1999) Liposomes: Rational Design, M. Dekker, New York, N.Y.; Lasic & Martin (1995) Stealth Liposomes, CRC Press, Boca Raton, Fla.; Nabel (1997) "Vectors for Gene Therapy" in Current Protocols in Human Genetics on CD-ROM, John Wiley & Sons, New York, N.Y.; and U.S. Pat. Nos. 4,235,871; 4,551,482; 6,197,333; and 6,132,766. Entrapment of an active agent within liposomes of the present invention can also be carried out using any conventional method in the art. In preparing liposome compositions, stabilizers such as anti-oxidants and other additives can be used. Other lipid carriers can also be used in accordance with the claimed invention, such as lipid microparticles, micelles, lipid suspensions, and lipid emulsions. See, e.g., Labat-Moleur et al. (1996) Gene Therapy 3:1010-1017; U.S. Pat. Nos. 5,011,634; 6,056,938; 6,217,886; 5,948,767; and 6,210,707. The composition of the invention may also involve lyophilized polynucleotides, which can be used with other pharmaceutically acceptable excipients for developing powder, liquid or suspension dosage forms, including those for intranasal or pulmonary applications. See, e.g., Remington: The Science and Practice of Pharmacy, Vol. 2, 19.sup.th edition (1995), e.g., Chapter 95 Aerosols; and International Patent Application No. PCT/US99/05547, the teachings of which are hereby incorporated by reference.

In some preferred embodiments, the pharmaceutical compositions of the invention are prepared for administration to the subject in the form of, for example, liquids, emulsions, powders, aerosols, tablets, capsules, enteric coated tablets or capsules, or suppositories. The optimal course of administration or delivery of the pharmaceutical agent may vary depending upon the desired result and/or on the subject to be treated. The pharmaceutical preparations of the present invention may be prepared and formulated as emulsions or microemulsions. Emulsions are usually heterogenous systems of one liquid dispersed in another in the form of droplets usually exceeding 0.1 mm in diameter. The emulsions of the present invention may contain excipients such as emulsifiers, stabilizers, dyes, fats, oils, waxes, fatty acids, fatty alcohols, fatty esters, humectants, hydrophilic colloids, preservatives, and anti-oxidants may also be present in emulsions as needed. These excipients may be present as a solution in either the aqueous phase, oily phase or itself as a separate phase. Suitable examples for emulsifiers and preservatives are given in US Patent Application No. 20040014956. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system. Suitable examples for surfanctants and cosurfactants are described in US Patent Application No. 20040014956. Microemulsions are particularly of interest from the standpoint of drug solubilization and the enhanced absorption of drugs. Lipid based microemulsions (both oil/water and water/oil) have been proposed to enhance the oral bioavailability of drugs. It is expected that the microemulsion compositions and formulations of the present invention will facilitate the increased systemic absorption of pharmaceutical agents of the invention from the gastrointestinal tract, as well as improve the local cellular uptake of oligonucleotides within the gastrointestinal tract, vagina, buccal cavity and other areas of administration.

In an embodiment, the present invention employs various penetration enhancers to effect the efficient delivery of the pharmaceutical agents of the invention (especially nucleic acids, particularly oligonucleotides) to the skin of humans and animals. Suitable penetration enhancer are described in US Patent Application NO. 20040146902, herein incorporated by reference.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. The dosage of the pharmaceutical agent may be adjusted to optimally induce the heterologous target gene or by a therapeutic response, without undue experimentation. In some embodiments, the dosage of the pharmaceutical agent is delivered at a certain level, and the level of the expression of the heterologous target gene is determined by the externally applied agent which inhibits the repressor protein or in other embodiments, induces expression from an inducible promoter. Thus, the exact dosage of the nucleic acid construct as disclosed herein administered will depend upon the data generated experimentally and in clinical trials, and from the level of administration of the externally applied agent which controls the heterologous target gene expression.

Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms. For example, the compositions of the present invention, when used as pharmaceutical compositions, can comprise about 1 ng to about 20 mgs of the pharmaceutical agent of the invention (e.g., the nucleic acid construct, plasmids, viral vectors, recombinant viruses, and mixtures thereof). The compositions of the present invention in which the delivery agents are donor cells or bacterium can be delivered in dosages of between about 1 cell to about $10^7$ cells/dose. Similarly, where the delivery agent is a live recombinant virus, a suitable vector-based composition contains between $1 \times 10^2$ pfu to $1 \times 10^{12}$ pfu per dose.

The pharmaceutical agent of the invention may be combined with any other drug, in some embodiments another agent for the treatment of the same medicinal indication. For example for pharmaceutical agents which have anti-cancer properties the agent may be combined with one or more chemotherapeutic agents (e.g., such as daunorubicin, idarubicin, mitomycin C, 5-fluorouracil (5-FU), methotrexate (MTX), taxol, vincristine, and cisplatin). Additional suitable teachings for pharmaceutical compositions and their preparation, administration and dosing in relation to oligonucleotide compounds which may be utilized within the scope of the present invention are given in US Patent Application No. 20040146902 which is incorporated herein by reference.

The term "anti-cancer agent" or "anti-cancer drug" is any agent, compound or entity that would be capably of negatively affecting the cancer in the subject, for example killing cancer cells, inducing apoptosis in cancer cells, reducing the growth rate of cancer cells, reducing the number of mestatic cells, reducing tumor size, inhibiting tumor growth, reducing blood supply to a tumor or cancer cells, promoting an immune response against cancer cells or a tumor, preventing or inhibiting the progression of cancer, or increasing the lifespan of the subject with cancer. Anti-cancer therapy includes biological agents (biotherapy), chemotherapy agents, and radiotherapy agents. The combination of chemotherapy with biological therapy is known as biochemotherapy.

Cancer therapy can include prophylaxis, including agents which slow or reduce the risk of cancer in a subject. In other embodiments, the treatments are any means to prevent the proliferation of cells with abnormal proliferation or cancerous cells. In some embodiments, the treatment is an agent which suppresses the EGF-EGFR pathway, for example but not limited to inhibitors and agents of EGFR. Inhibitors of EGFR include, but are not limited to, tyrosine kinase inhibitors such as quinazolines, such as PID 153035, 4-(3-chloroanilino)quinazoline, or CP-358,774, pyridopyrimidines, pyrimidopyrimidines, pyrrolopyrimidines, such as CGP 59326, CGP 60261 and CGP 62706, and pyrazolopyrimidines, 4-(phenylamino)-7H-pyrrolo[2,3-d]pyrimidines (Traxler et al., (1996) J. Med Chem 39:2285-2292), curcumin (diferuloyl methane) (Laxmin arayana, et al., (1995), Carcinogen 16:1741-1745), 4,5-bis(4-fluoroanilino)phthalimide (Buchdunger et al. (1995) Clin. Cancer Res. 1:813-821; Dinney et al. (1997) Clin. Cancer Res. 3:161-168); tyrphostins containing nitrothiophene moieties (Brunton et al. (1996) Anti Cancer Drug Design 11:265-295); the protein kinase inhibitor ZD-1 839 (AstraZeneca); CP-358774 (Pfizer, Inc.); PD-01 83805 (Warner-Lambert), EKB-569 (Torrance et al., Nature Medicine, Vol. 6, No. 9, September 2000, p. 1024), HKI-272 and HKI-357 (Wyeth); or as described in International patent application WO05/018677 (Wyeth); W099/09016 (American Cyanamid); W098/43960 (American Cyanamid); WO 98/14451; WO 98/02434; W097/38983 (Warener Labert); W099/06378 (Warner Lambert); W099/06396 (Warner Lambert); W096/30347 (Pfizer, Inc.); W096/33978 (Zeneca); W096/33977 (Zeneca); and W096/33980 (Zeneca), WO 95/19970; U.S. Pat. App. Nos. 2005/0101618 assigned to Pfizer, 2005/0101617, 20050090500 assigned to OSI Pharmaceuticals, Inc.; all herein incorporated by reference. Further useful EGFR inhibitors are described in U.S. Pat. App. No. 20040127470, particularly in tables 10, 11, and 12, and are herein incorporated by reference.

In another embodiment, the anti-cancer therapy includes a chemotherapeutic regimen further comprises radiation therapy. In an alternate embodiment, the therapy comprises administration of an anti-EGFR antibody or biological equivalent thereof.

In some embodiments, the anti cancer treatment comprises the administration of a chemotherapeutic drug selected from the group consisting of fluoropyrimidine (e.g., 5-FU), oxaliplatin, CPT-11, (e.g., irinotecan) a platinum drug or an anti EGFR antibody, such as the cetuximab antibody or a combination of such therapies, alone or in combination with surgical resection of the tumor. In yet a further aspect, the treatment compresses radiation therapy and/or surgical resection of the tumor masses. In one embodiment, the present invention encompasses administering to a subject identified as having, or increased risk of developing RCC an anti-cancer combination therapy where combinations of anti-cancer agents are used, such as for example Taxol, cyclophosphamide, cisplatin, gancyclovir and the like. Anti-cancer therapies are well known in the art and are encompassed for use in the methods of the present invention. Chemotherapy includes, but is not limited to an alkylating agent, mitotic inhibitor, antibiotic, or antimetabolite, anti-angiogenic agents etc. The chemotherapy can comprise administration of CPT-11, temozolomide, or a platin compound. Radiotherapy can include, for example, x-ray irradiation, w-irradiation, β-irradiation, or microwaves.

The term "chemotherapeutic agent" or "chemotherapy agent" are used interchangeably herein and refers to an agent that can be used in the treatment of cancers and neoplasms, for example brain cancers and gliomas and that is capable of treating such a disorder. In some embodiments, a chemotherapeutic agent can be in the form of a prodrug which can be activated to a cytotoxic form. Chemotherapeutic agents are commonly known by persons of ordinary skill in the art and are encompassed for use in the present invention. For example, chemotherapeutic drugs for the treatment of tumors and gliomas include, but are not limited to: temozolomide (Temodar), procarbazine (Matulane), and lomustine (CCNU). Chemotherapy given intravenously (by IV, via needle inserted into a vein) includes vincristine (Oncovin or Vincasar PFS), cisplatin (Platinol), carmustine (BCNU, BiCNU), and carboplatin (Paraplatin), Mexotrexate (Rheumatrex or Trexall), irinotecan (CPT-11); erlotinib; oxalipatin; anthracyclins-idarubicin and daunorubicin; doxorubicin; alkylating agents such as melphalan and chlorambucil; cis-platinum, methotrexate, and alkaloids such as vindesine and vinblastine.

In one embodiment, the pharmaceutical agents comprising nucleic acid construct of the invention can be administered to subjects. Examples of subjects include mammals, e.g., humans and other primates; cows, pigs, horses, and farming (agricultural) animals; dogs, cats, and other domesticated pets; mice, rats, and transgenic non-human animals.

D. Biotechnological Applications

For further elaboration of general techniques useful in the practice of this invention, the practitioner can refer to standard textbooks and reviews in cell biology, tissue culture. General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

EXAMPLES

The examples presented herein relate to compositions, systems and methods for tight, regulatable induction of transgene expression in a mammalian cell. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Methods

Synthetic Network Construction.

The CMV, RSV, and U6 promoters were amplified by PCR from pCMVLacI (Stratagene), pOPI3CAT (Stratagene), and U6/tetO (a gift from D. Takai, University of Tokyo), respectively. The SV4O introns containing three lac operator sites were PCR amplified from pOPI3CAT (Stratagene). Genes encoding EGFP, TetR, and LacI were amplified by PCR from pIRES2-EGFP (Clontech), pcDNA6/TR (Invitrogen), and pCMVLacI (Stratagene), respectively. The genes encoding DTA and neomycin resistance were cut out of p22EDT1 (a gift from J. Sawicki, Lankenau Institute for Medical Research) and pNHS1 03 . . . v3 (a gift from M. Deans, Harvard Medical School) plasmids, respectively. The box gene was PCR amplified from pcDNA3-bax (Addgene) and inserted into LTRi.

Cell Culture Conditions and Transfections.

CHO-K1 and HEK293 cells were obtained from ATCC (ATCC CCL61 and CRL1573, respectively). The CHO-K1 cells were maintained in F12K medium containing 10% FBS and penicillin/streptomycin, and the HEK293 cells were maintained in DMEM medium containing 10% FBS and penicillin/streptomycin. Both cells lines were grown in a humidified 5% $CO_2$, 37° C. incubator. The day before transfection, cells were plated in a 12-well plate to ~85% confluency. These cells were transfected with 1.6 µg of expression plasmid using Lipofectamine 2000 reagent (Invitrogen). For the transient experiments, cells were washed with PBS, trypsinized, and analyzed by flow cytometry 24 hr after transfection.

Rosa26 fibroblasts were obtained from embryonic day 14.5 Rosa26-R mice. The cells were maintained in embryonic fibroblast medium (high-glucose DMEM, 10% FBS, penicillin/streptomycin, L-glutamine, and sodium pyruvate) and grown in a humidified 5% $CO_2$, 37CC incubator. These cells were transfected with 0.8 µg of LTRi-cre and LTRi-bax using Lipofectamine 2000 reagent (Invitrogen). The LTRi-cre cells were analyzed by β-galactosidase staining 48 hr after transfection. The LTRi-bax cells were stained and analyzed by flow cytometry 48 hr after transfection.

For establishing stable cell lines, cells were plated in a 10 cm dish at ~85% confluency the day before transfection. The expression vector was linearized, and cells were transfected with the linearized vector using Lipofectamine 2000 per the manufacturer's protocol. Twenty-four hours after transfection, cells were passed and cultured in the presence of the antibiotic G418 (600 µg/ml, Invitrogen) for 2 weeks. The neomycin resistance (nec) gene encoded on the vector confers resistance to G418 and is an indication of stable integration of plasmid DNA into the host cell chromosomes. Stable colonies were picked and grown in separate dishes for analysis using flow cytometry.

Inducing Cells with IPTG.

For the transient experiments, 1 mM of IPTG was added shortly after the transfections were performed. For the stable experiments, fresh medium containing IPTG was added daily to the cells.

Flow Cytometry.

For the EGFP analysis, transfected cells were harvested, washed, and resuspended in PBS. Fluorescence data were collected using a FACSCalibur flow cytometer (BD Biosciences) integrated with Cell-Quest software. The cells were analyzed with a 488 nm argon excitation laser and a 515-545 nm emission filter (FL1). Data analysis was performed using WinMDI software, version 2.8 (J. Trotter, The Scripps Research Institute) and MATLAB (The MathWorks, Inc.). Cell samples were assayed at a medium flow rate until 30,000 cells had been collected within a forward-scatter and side-scatter gate to minimize fluorescence variation due to cell size.

For the apoptosis study, cells were stained with Alexa Fluor 488-conjugated annexin V and propidium iodide (P1) using the Vybrant Apoptosis Assay Kit (Invitrogen) per the manufacturer's protocol. Cell samples were assayed at a medium flow rate until 1 5,000 cells had been collected.

Fluorescence Microscopy. Coverslips were treated with protamine and placed in the bottoms of a 12-well plate. Cells were grown on these coverslips overnight and transfected the next day with 1.6 µg of expression plasmid using Lipofectamine 2000 reagent (Invitrogen) per the manufacturer's protocol. The following morning, the cells were washed with PBS and fixed with 4% paraformaldehyde in PBS for 15 mm at room temperature. After fixation, the coverslips were washed with PBS, and mounting medium was placed on the cells. The coverslips were then mounted face down onto slides, and the cells were visualized for fluorescence using a Nikon Eclipse 80i microscope.

Staining for β-Gatactosidase.

Cells were grown in 12-well plates, and 24 hr after plating, they were transfected with 0.8 µg of LTRi-cre using Lipofectamine 2000 reagent (Invitrogen) per the manufacturer's protocol and exposed to 1 mM IPTG. Cells were incubated for 48 hr, fixed with paraformaldehyde, washed with PBS, and stained with X-gal staining buffer.

Staining for Apoptosis and Cell Death.

Cells were grown in 12-well plates, and 24 hr after plating, they were transfected with 0.8 µg of LTRi-bax using Lipofectamine 2000 reagent (Invitrogen) per the manufacturer's protocol and exposed to the indicated levels of IPTG. Cells were incubated for 48 hr, and adherent cells were harvested by mild trypsinization and pooled together with detached cells. Cells were stained with Alexa Fluor 488-conjugated annexin V and P1 using the Vybrant Apoptosis Assay Kit (Invitrogen) per the manufacturer's protocol. In live cells, phosphatidylserine is located in the cytoplasmic surface of the cell membrane; however, in apoptotic cells, it translocates to the outer leaflet of the plasma membrane (van Engeland et al., 1998). Annexin V has a high affinity for phosphatidylserine; therefore, annexin V conjugated with Alexa Fluor 488 can identify apoptotic cells by binding to phosphatidylserine and can be analyzed by flow cytometry measuring the fluorescence emission at 530 nm (FL1). P1 accesses the inner cell of dead cells due to damaged plasma membranes and binds tightly to nucleic acids. It is impermeable to live and apoptotic cells but stains dead cells with red fluorescence. Dead cells appear red and can be analyzed by flow cytometry measuring the red florescence emission >575 nm (FL3). Moreover, live cells are annexin V negative and P1 negative, apoptotic cells are annexin V positive and P1 negative, and dead cells are annexin V negative and P1 positive.

Immunoblot Analysis

Cells were grown in 10 cm dishes and induced with 1 mM IPTG for the specified days. After induction, cells were scraped and lysed in lysis buffer (0.15M NaCl, 5 mM EDTA pH 8.0, 1% triton×100, 10 mM Tris-Cl pH 7.4) with protease inhibitor cocktail (Sigma). Proteins were resolved by SDS-PAGE and transferred onto nitrocellulose membranes (Bio-Rad Laboratories). The membranes were blocked in Tris-buffered saline containing 0.1% Tween 20 (TBST) and 5% nonfat dry milk for 1 hour and then incubated with, EGFP primary antibody (mouse monoclonal EGFP antibody; Invitrogen) diluted 1:2000 overnight. The membrane was washed with TBST 4 times for 10 minutes and then incubated with goat anti-mouse HRP conjugate secondary antibody (Bio-Rad Laboratories) diluted 1:2000 in TBST with 5% nonfat dry milk at room temperature for 1 hour.

Example 1

Design of the Genetic Switch

Figure 10:
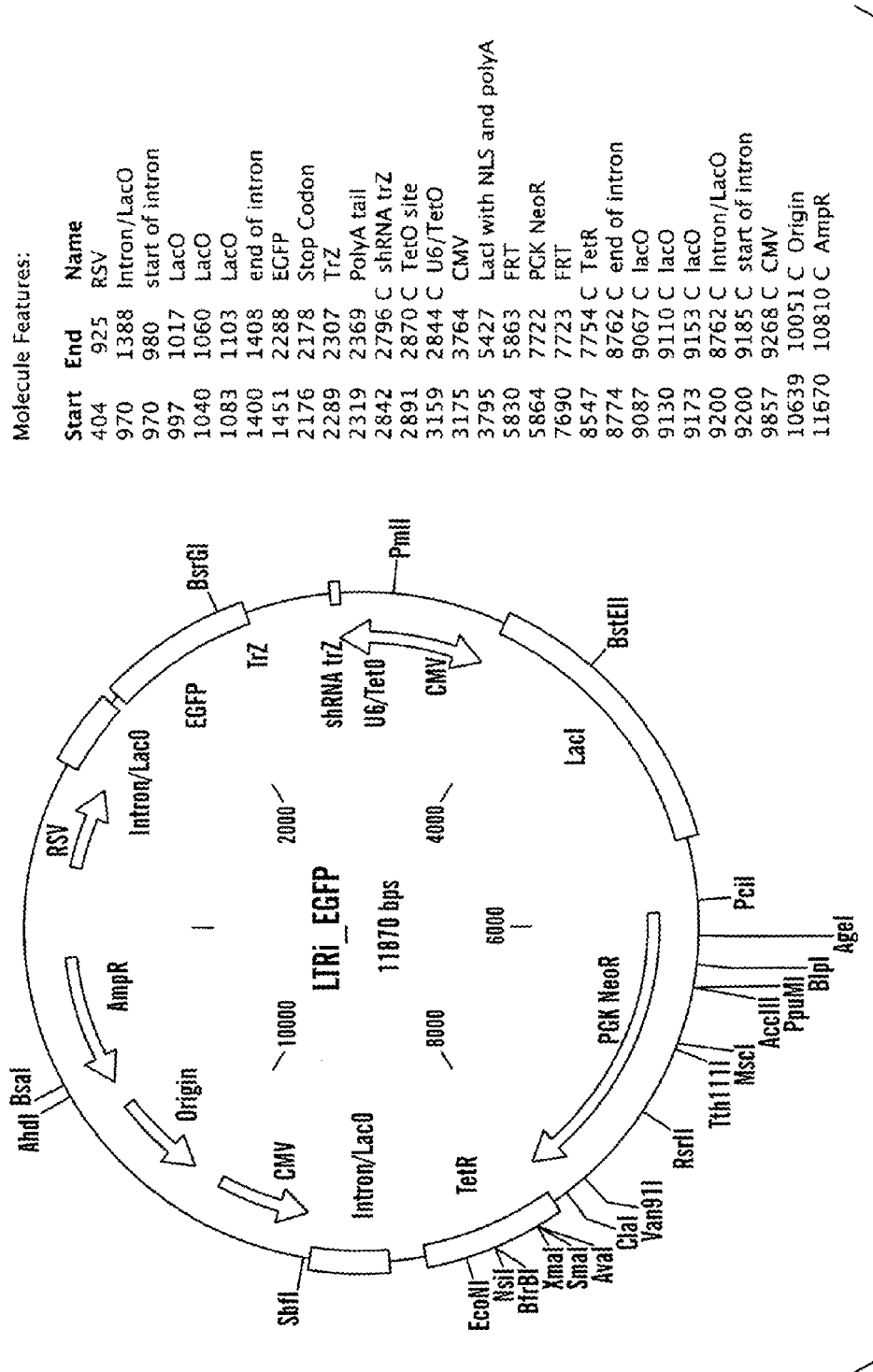
FIG. 10 shows a schematic illustration of the LTRi-eGFP construct.

The inventors initially used our genetic switch to regulate the expression of enhanced green fluorescent protein, EGFP (LTRiEGFP) which corresponds to nucleic acid sequence SEQ ID NO:4 or FIG. 10. LTRi-EGFP was designed so that in the off state (FIG. 1A), LacI provides transcriptional repression of EGFP and any leakage of the EGFP transcript is knocked down by the RNAi component of the switch. Specifically, the LacI repressor module produces LacI proteins that bind to the lac operator sites located in an intron adjacent to EGFP in the transgene module. Any EGFP mRNA that is transcribed as a result of incomplete repression is subsequently targeted for degradation by shRNA produced by the RNAi module. The shRNA molecules target the mRNA of EGFP via a synthetic target sequence that was placed in the 3'UTR. In addition to repressing the transcription of the transgene, the LacI proteins also repress the second repressor module in the system, the tetR repressor module. This component controls the functionality of the RNAi module by regulating the transcription of shRNA molecules that target the mRNA of EGFP. The genetic switch can be flipped to the on state (FIG. 1B) by adding IPTG, which binds to LacI and produces a conformational change in the repressor proteins, causing them to no longer bind to the/ac operator sites. This allows for the transcription of EGFP and tetR. The Tet repressor proteins bind to the tet operator site located in the U6 promoter of the RNAi module, which represses the transcription of shRNA. The resulting effect is robust expression of EGFP.

Example 2

Construction and Functional Characterization of the Genetic Switch

The inventors next constructed LTRi-EGFP in a modular fashion and tested it using microscopy and flow cytometry (FIG. 2). First, the inventors designed a posttranscriptional module that uses a U6 promoter containing a tet operator site to transcribe a 42 nucleotide RNA transcript. This transcript forms a shRNA and has complementarity to a 19 nucleotide sequence in the E. coli β-galactosidase sequence. This 19 nucleotide target sequence was placed in the 3'UTR of the EGFP gene to be targeted by the shRNA, giving rise to a system that is not gene specific, allowing for any transgene to be con-trolled by the module. Furthermore, by designing the target sequence to have complementarity to β-galactosidase, the inventors designed the construct to minimize any potential off-target effects that could be caused by the RNAi module. Using transient transfections, the inventors compared the expression of EGFP with and without the target and demonstrated that the presence of the target sequence in the 3'UTR did not significantly change the expression of EGFP. As a result, the inventors used the transgene module controlling the expression of EGFP with the target sequence (FIG. 2A) as our positive control (corresponding to maximum EGFP expression).

Figure 2B:
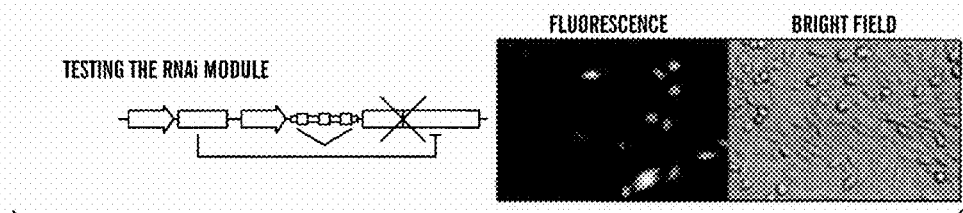

Next, the inventors placed the RNAi module on the same plasmid as the transgene module to test the effectiveness of RNAi alone (FIG. 2B). Using transient transfections, the inventors demonstrated that this system offers approximately 80% knockdown of the transgene (FIG. 2E) compared to the positive control. Microscope images confirmed that RNAi alone is incapable of completely shutting off EGFP expression (FIG. 2B). The inventors next assessed other target sequences (e.g., to luciferase) and demonstrated similar results. To ensure that the shRNA effect was due to targeting the 3'UTR sequence, the inventors placed the RNAi module onto a plasmid that expressed EGFP but lacked the target sequence in the 3'UTR. Importantly, the inventors demonstrated no change in the expression of EGFP, indicating that the shRNA did not exhibit off-target effects with respect to EGFP.

Figure 2C:
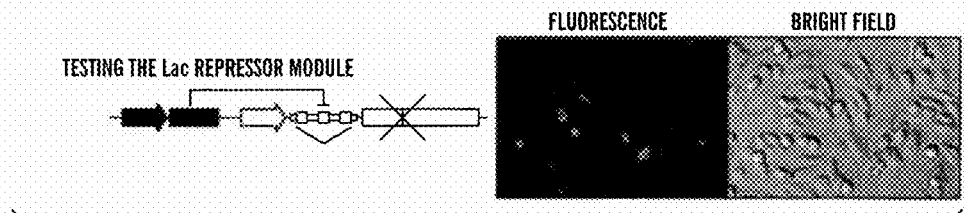

We then placed the /ac/ repressor module on the same plasmid as the transgene module to examine the effectiveness of repression alone (FIG. 2C). Using transient transfections, the inventors discovered that this system offers approximately 85% repression (FIG. 2E) as compared to the positive control. Similar to the RNAi module, microscope images showed that transcriptional repression alone is incapable of completely shutting off EGFP expression (FIG. 2C).

Figure 2D:
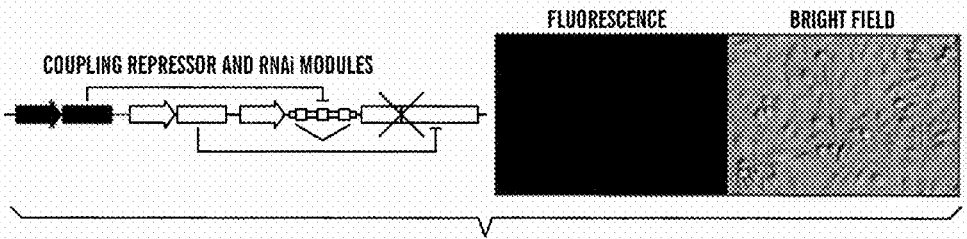
Figure 2E:
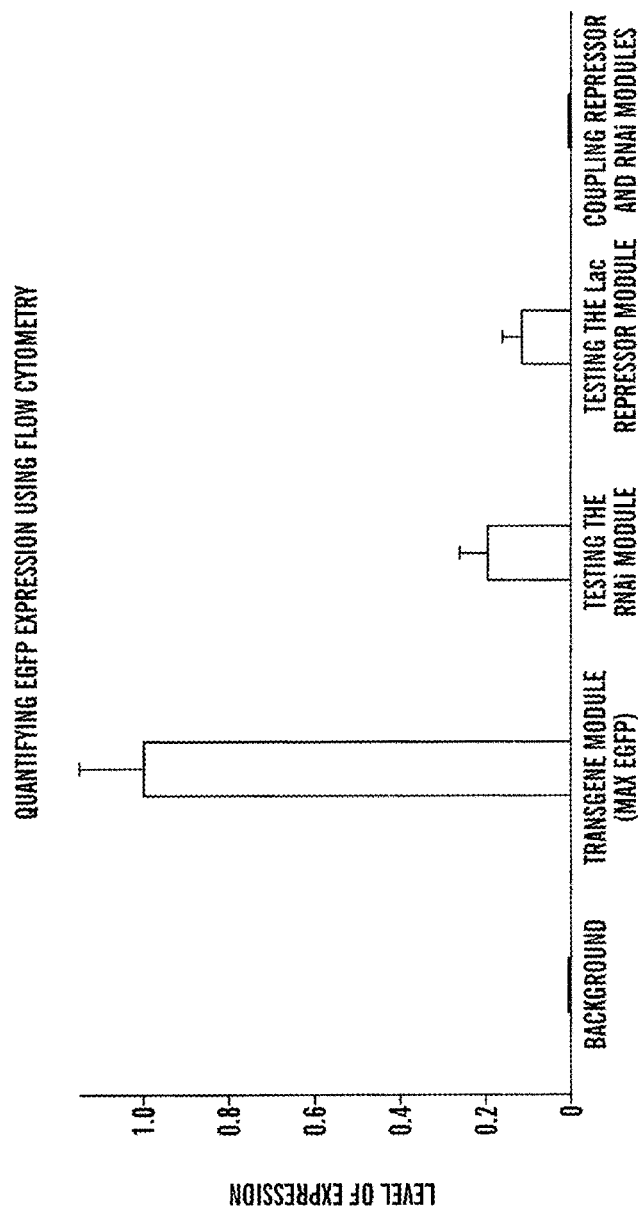

Finally, the inventors coupled the transcriptional and post-transcriptional mechanisms by placing both the /ac/ repressor module and the RNAi module on the same plasmid as the transgene module (FIG. 2D). The inventors demonstrated that this system offers greater than 99% repression (FIG. 2E) as compared to the positive control. Microscope images confirmed that there is effectively no EGFP expression when the transcriptional and posttranscriptional mechanisms are coupled together (FIG. 2D). To complete the synthetic gene network, the inventors also added the last module, the tetR repressor module (FIG. 1). As noted above, this module acts to repress the transcription of the shRNA molecules from the RNAi module.

Example 3

Characterizing the Dynamics and Tunability of the Genetic Switch

Figure 7A:
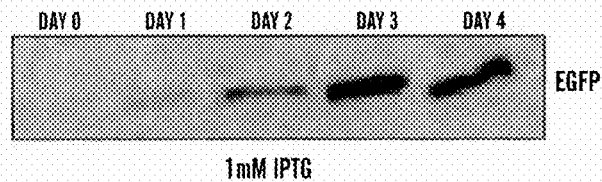
FIG. 7 shows the population Effect of LTRi-EGFP during Induction. Panel 7A shows an immunoblot of EGFP with increasing induction levels. Panel 7B shows analysis using flow cytometry of CHO cells stably transfected with LTRi-EGFP shows a clear population shift with increased induction levels.
Figure 7B:
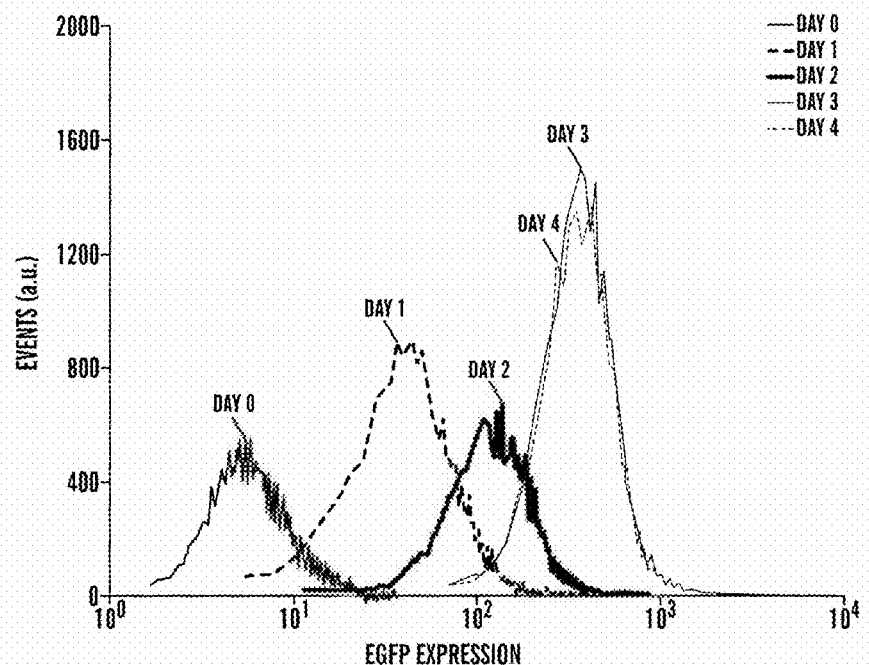

Next, the inventors stably transfected LTRi-EGFP into CHO cells to characterize the dynamics of the system. Using flow cytometry, the inventors analyzed the switching-time characteristics of the network over a 14 day period (FIG. 3A, solid blue line). After 3 days of induction, the system was fully induced, exhibiting expression levels approximately 85-fold greater than basal levels. When the inducer was removed, full repression/knockdown was demonstrated in 3 days. The system could be repeatedly and reversibly induced on and off with the addition and removal of IPTG (FIG. 3A). To validate the levels of EGFP protein expression, immunoblots were performed on the specified days of induction (FIG. 7A). Consistent with our flow cytometry results, the immunoblots showed no detectable EGFP protein in the absence of inducer and a gradual increase in EGFP protein up until day 3 of induction. The inventors demonstrate by flow cytometry data (FIG. 7B) that the induction of the switch was uniform across the cells, i.e., an induction level of 50% arose from all cells expressing at approximately 50% of the maximum.

Figure 3C:
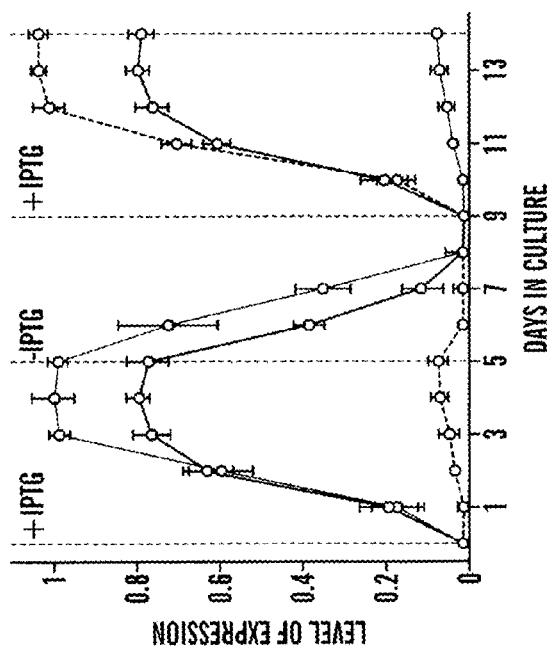
FIG. 3 shows the Genetic Switch Controls Gene Expression in a Tunable and Reversible Fashion. Panel 3A shows CHO cells (solid blue line with circles) and HEK293 cells (dotted red line with triangles) were stably transfected with LTR1-EGFP. Using flow cytometry, we studied the switching time over a 14 day period. The system was repeatedly induced on and off. Each data point represents the average EGFP expression in at least five independent experiments. Panel 3B shows the tunability of LTRi-EGFP stably transfected in CHO cells was studied by adding five different amounts of inducer. Each data point represents the average EGFP expression in at least five independent experiments. Panel 3C shows analysis of the flexibility of the control maintained by the switch stably transfected in CHO cells, three different induction levels were chosen: high (1 mM IPTG), medium (25 µM IPTG), and low (250 µM IPTG). After full induction at each of these levels, the expression of EGFP was turned off. The cells originally at the high induction level (blue data points) were reinduced at the low level, and the cells originally at the low induction level (red data points) were reinduced at the high level. The cells originally at the medium induction level (black data points) were reinduced at the same level. Each data point represents the average EGFP expression in at least five independent experiments. Panel 3D shows an induction curve is shown for both stably transfected CHO cells (solid blue line with circles) and HEK293 cells (dotted red line with triangles). Each data point represents the mean EGFP expression in ten independent experiments.

The inventors also added different amounts of IPTG and demonstrated that the construct switch can be used to tune the level of EGFP expression (FIG. 3B). The inventors demonstrated that EGFP expression can be maintained at different levels by varying inducer concentrations. To further examine the flexibility and control maintained by LTRi, the inventors assessed the effects of three induction levels: high (1 mM IPTG), medium (25 µM IPTG), and low (250 pM IPTG). After full induction at each of these levels, the expression of EGFP was turned off (FIG. 3C). The cells originally at the high induction level (1 mM IPTG) were reinduced with 250 pM IPTG, and the cells originally at the low induction level (250 pM IPTG) were reinduced with 1 mM IPTG. The cells originally at the medium induction level (25 µM IPTG) were reinduced at the same level. The inventors demonstrate that they could predictably manipulate the expression of EGFP by changing the amount of inducer, independent of the expression history of the switch (FIG. 3C). Together, these results demonstrate that LTRi can precisely control the expression level of individual genes in a tunable and reversible fashion.

Figure 3D:
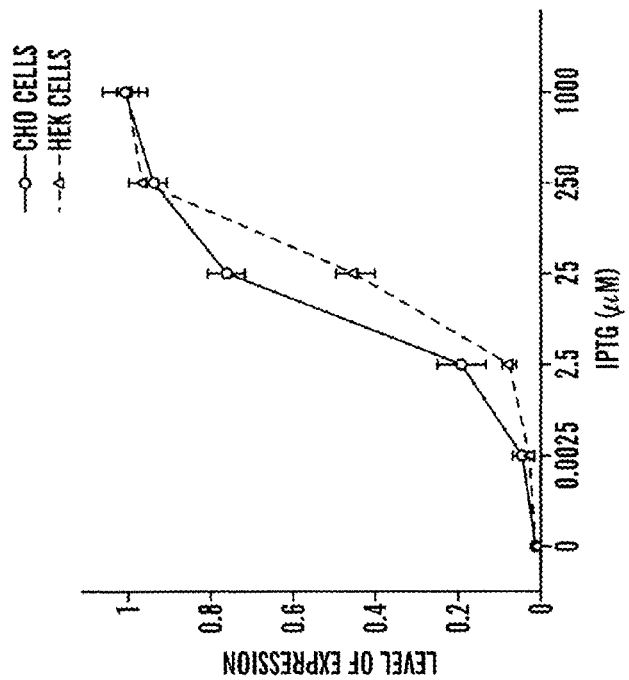
Figure 8:
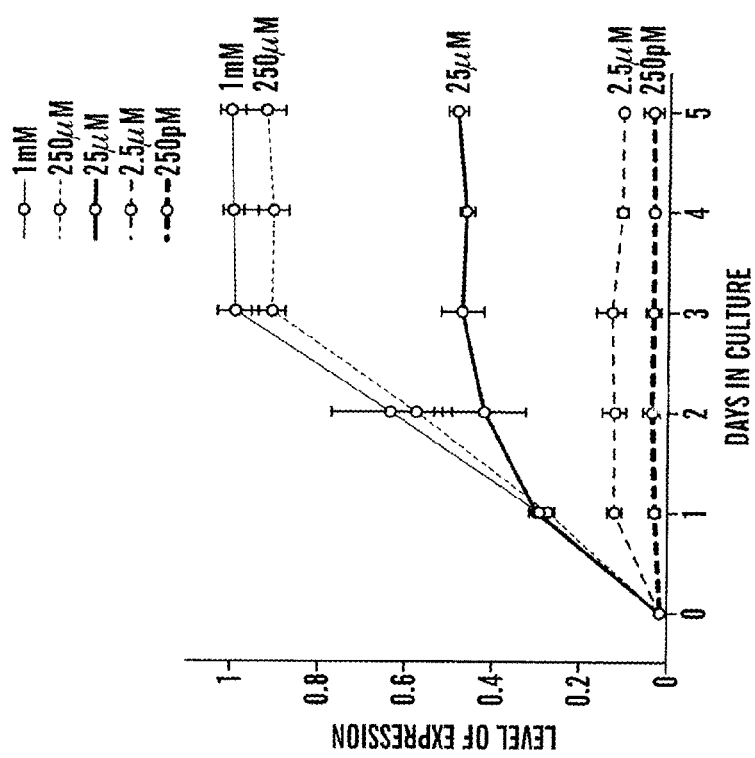
FIG. 8 shows the tunability of LTRi-EGFP in HEK293 Cells. The tunability of LTRi-EGFP stably transfected in HEK293 cells was studied by adding five different amounts of inducer. Each data point represents the average EGFP expression in at least five independent experiments; standard deviations are shown as error bars.

To compare the dynamics of the construct switch as disclosed herein in other cell lines, the inventors stably transfected LTRi-EGFP into HEK293 cells. The inventors demonstrate that the dynamics of LTRi is independent of cell type (FIG. 3A). Moreover, the inventors also demonstrated dose-response levels of LTRi-EGFP in both CHO and HEK cells by assessing different induction levels at day 3 of induction and obtained similar dose-response characteristics (FIG. 3D). Likewise, the inventors demonstrate that LTRi can be used to tune the expression of EGFP in HEK293 cells with results similar to those obtained in CHO cells (FIG. 8). Together, the inventors have demonstrated that the genetic switch as disclosed herein can precisely control the expression level of an individual gene in a tunable and reversible fashion, regardless of cell type.

Example 4

Demonstrating the Tight Repression and Biological Utility of the Genetic Switch

Figure 4A:
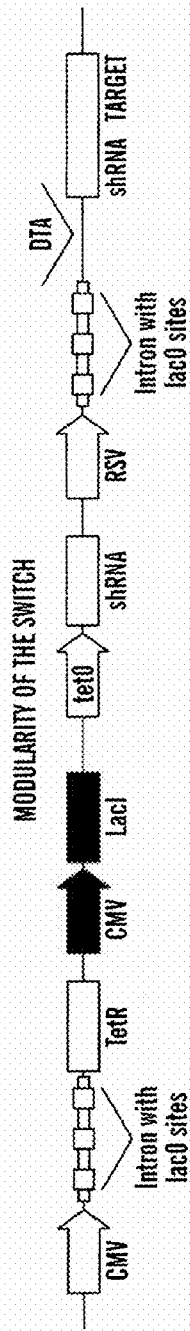
FIG. 4 shows the use of the Genetic Switch to tightly Control DTA Expression. Panel 4A shows a schematic diagram of LTRi-DTA. Panel 4B shows the first column shows a schematic diagram of LTRi-DTA in the off state, along with an EGFP reporter module. The second and third columns show bright-field and fluorescence microscope images, respectively, of cells with LTRi-DTA in the off state. Panel 4C, first column, shows a schematic diagram of LTRi-DTA in the on state, along with an EGFP reporter module. Panel 4C second and third columns show bright-field and fluorescence microscope images, respectively, of cells with LTRi-DTA in the on state.
Figure 4B:
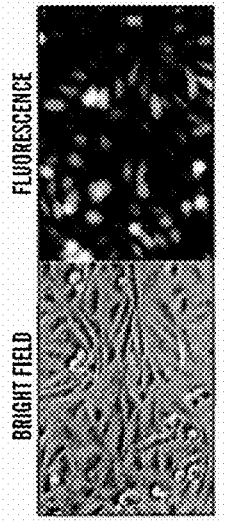
Figure 4B:
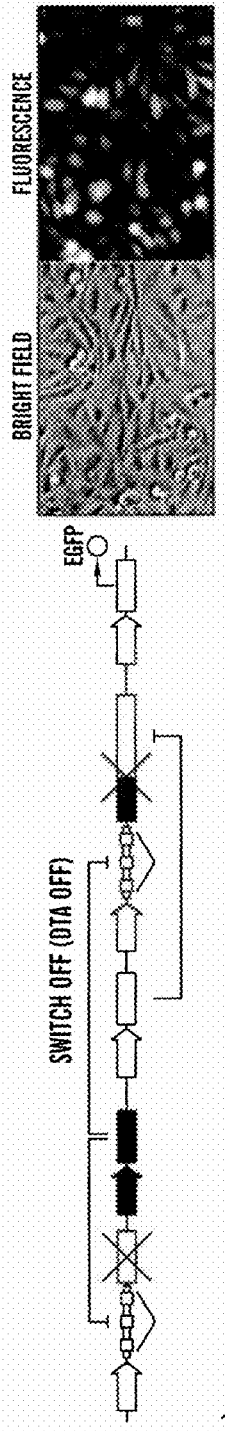
Figure 4C:
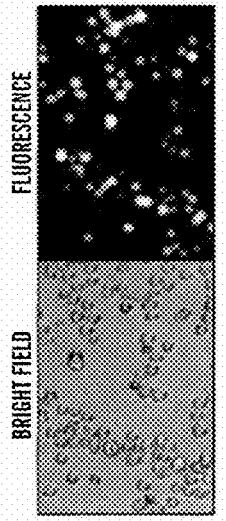
Figure 4C:
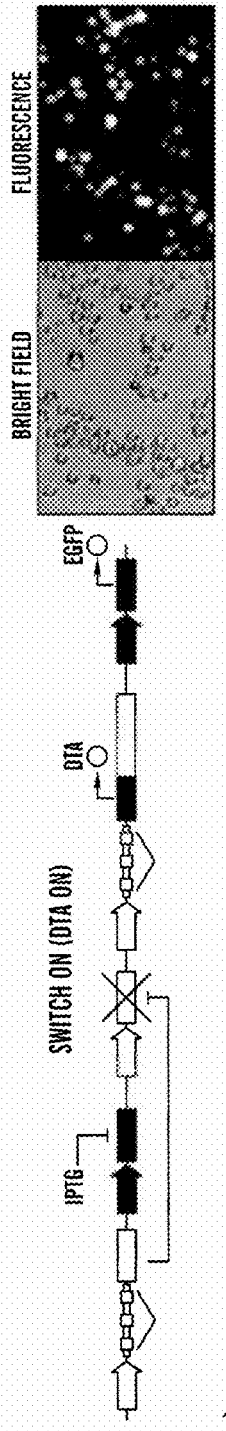

Because the regulatory elements of LTRi that are responsible for the tight control of gene expression are not associated with either a specific transgene or specific promoters, the switch is capable of controlling any gene of interest. In addition, tissue-specific promoters can be used for in vivo experiments. To emphasize this modularity and to highlight the level of gene silencing achieved by the switch, the inventors replaced EGFP with DTA (LTRi-DTA) (FIG. 4A). DTA functions by inhibiting protein synthesis (Greenfield et al., 1983), and it has been shown to be highly toxic in cells, with a single molecule being sufficient to kill a cell (Yamaizumi et al., 1978). Despite DTA's toxicity, the inventors were able to establish stable cell lines containing the switch controlling the expression of DTA and to grow them for more than 4 weeks. To confirm that all cells in culture contained LTRi-DTA, the inventors also added EGFP driven by a constitutive promoter to the same plasmid as the genetic switch (FIG. 4A). Thus, any cell expressing EGFP also carried the switch regulating the expression of DTA. The inventors demonstrated that cells with the genetic switch in the off state survived despite the presence of the DTA gene (FIG. 4B) and the cells could be triggered to die following induction with IPTG (FIG. 4C). Microscope images confirmed these findings (FIGS. 4B and 4C), which clearly demonstrated that the inventors genetic switch construct can be used to effectively turn any gene off, including turning on and off cytotoxic genes and thus can specifically induce cell death.

Example 5

Figure 9:
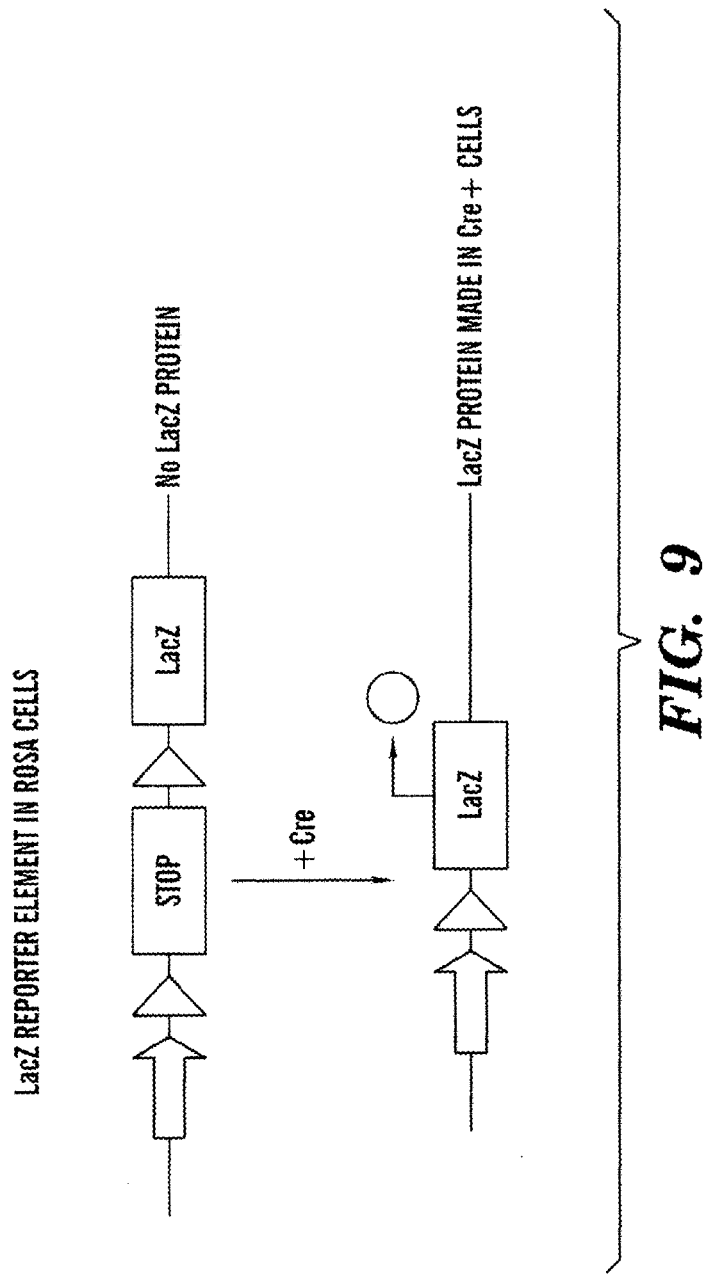
FIG. 9 shows the β-Galactosidase Reporter System in Rosa26 Cells. In the absence of Cre recombinase, no β-galactosidase protein is translated. However, in the presence of Cre recombinase, the stop element is removed, resulting in β-galactosidase translation.

To explore other potential in vivo experimental applications, the inventors used LTRi to regulate the expression of Cre recombinase (FIG. 5A). LTRi-cre was transiently transfected into primary mouse fibroblasts derived from Rosa26 β-galactosidase reporter cells (Soriano, 1999). In these cells, Cre recombinase activity results in the deletion of transcriptional stop elements and facilitates the expression of β-galactosidase (FIG. 9). In this context, genetic recombination occurs, causing a permanent genetic modification, so even low levels of Cre expression can be detected histologically. In Example 5, the synthetic target in the transgene module was changed to a 19 nucleotide segment of luciferase. Cells with LTRi-cre in the off state showed no indication of β-galactosidase activity (FIG. 5B). However, upon induction of the switch with IPTG, cells that were transfected with LTRi-cre expressed the β-galactosidase protein and turned blue (FIG. 5C).

Figure 6A:
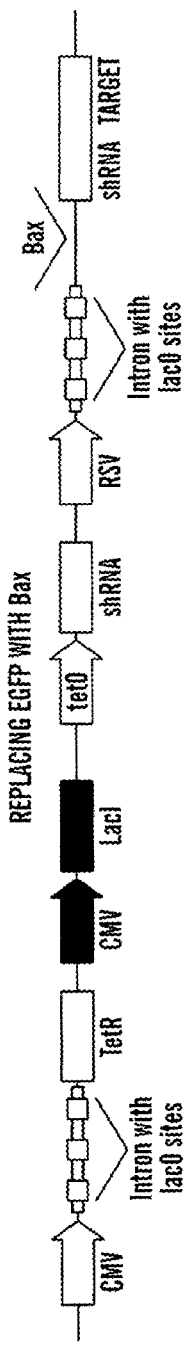
FIG. 6 shows the use of the Genetic Switch Tunes the Expression Level of Bax, Revealing a Possible Threshold Effect for Inducing Apoptosis. Panel 6A shows as schematic diagram of LTRi-bax. Rosa26 cells were transiently transfected with LTRi-bax. Panel 6B shows quantitative flow cytometry analysis of apoptotic and dead cells using annexin V and propidium iodide (P1) staining. After 48 hr of induction at the indicated IPTG levels, cells were stained and analyzed using Alexa Fluor 488-conjugated annexin V along with P1. The apoptotic cells were Alexa Fluor 488 positive and P1 negative, whereas the dead cells were P1 positive. Low and moderate levels of Bax show no increase in either apoptosis or cell death, whereas high induction levels of Bax indicate a significant increase in apoptosis and cell death. To ensure that cell death and apoptosis did not result from the presence of IPTG, we exposed nontransfected cells to the indicated levels of IPTG (black lines). Each data point represents the mean expression of annexin V and P1 in four independent experiments.
Figure 6B:
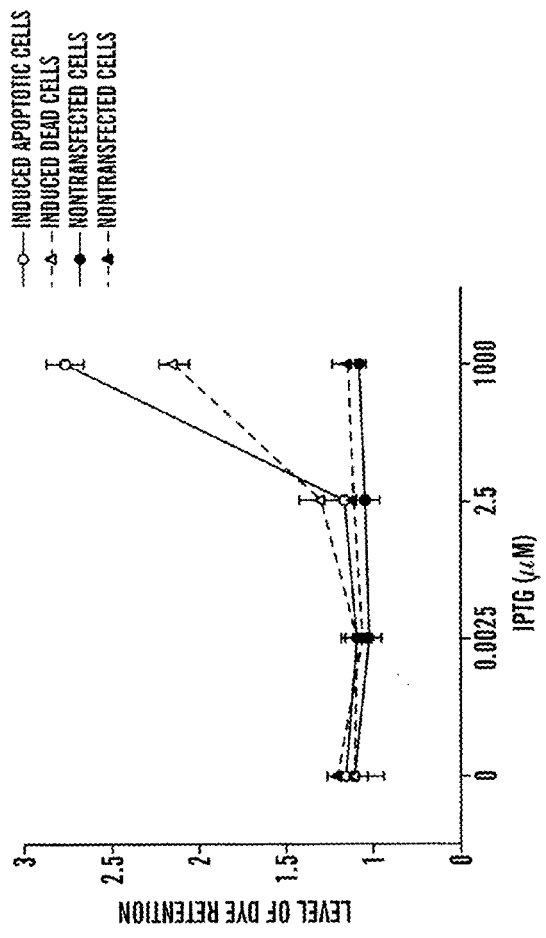

To investigate whether LTRi can also be used to regulate a biological process, the inventors put bax, a proapoptotic gene, under the control of the switch (LTRi-bax) (FIG. 6A). As previously reported, the overexpression of Bax causes cells to undergo apoptosis, and high levels of Bax protein are widely regarded as a hallmark of cells undergoing apoptosis (Pastorino et al., 1998; Shinoura et al., 1999; Wolter et al., 1997). pUC19 was transfected into Rosa26 cells to establish a basal level of apoptosis and cell death that results from transfecting the cells. All data were normalized to the level of dye retention obtained from these transfections. Transient transfections of LTRi-bax were performed and analyzed 48 hr after transfection at four different induction levels: 0, 250 pM, 2.5 μM and 1 mM IPTG. The inventors demonstrated that at low and moderate levels of Bax expression, cells did not display increased levels of apoptosis (FIG. 6B); however, at high levels of Bax expression, there was a significant increase in apoptosis and cell death (FIG. 6B). These findings demonstrate a possible threshold response for Bax-induced apoptosis. To ensure that cell death and apoptosis were not a result of the presence of IPTG, the inventors exposed non-transfected cells to the indicated levels of IPTG and found no change in apoptosis or cell death (FIG. 6B).

Example 6

Despite sophisticated advances in developing tools for controlling gene expression, the ability to effectively regulate a transgene of interest is still imperfect due to leakiness, poor induction levels, and irreversibility of the genetic modification. In this study, the inventors have discovered a method by which these limitations can be overcome by constructing and engineering a genetic network of interacting modules for regulating mammalian gene expression. The inventors use well-characterized, individually engineered modules to create a genetic circuit that exhibits undetectable levels of gene expression in the off state. Gene expression can be triggered by the addition of an inducer molecule, such as IPTG, and the level of transgene expression can be precisely and reversibly tuned by adding various amounts of such an inducer such as IPTG. Impressively, as seen with the stable cell lines containing the switch controlling EGFP and DTA, a regulated state can be transmitted as cells grow and divide.

Recently, Szulc et al. (2006) introduced a method for controlling both Pol II- and Pol III-type promoters using the KRAB domain tethered to the tetR repressor. This system was used to regulate the production of a transgene and shRNA to a separate target gene in the cellular genome. While this method offers an approach for regulating endogenous genes, its use is limited as it lacks specificity and robustness because the shRNAs target mRNA sequences of the endogenous gene of interest which is highly likely to lead to undesirable off-target effects.

More recently, Banaszynski et al. (2006) generated a technique for regulating protein stability in mammalian cells by fusing a 107 amino acid residue from the rapamyicin-binding protein (FKBP) to a protein of interest. They showed that the residue can function as a destabilizing domain (DD) to render the protein fused to this domain unstable and thus no longer functional. The addition of a ligand protects the protein fused to the DD from degradation; therefore, the protein becomes functional with the addition of the ligand (Banaszynski et al., 2006). This system offers an approach for regulating gene expression through a posttranslational mechanism. However, the use and functionality of this system is limited as the requirement for fusion proteins limits it for studying native protein function, as fusion proteins often do not function like native proteins since the introduction of the additional amino acids disrupts folding, which can sterically inhibit catalytic or protein binding domains.

It is well-established that dynamic changes of gene expression levels occur throughout the life of organisms, particularly during development and the onset of disease or pathology. The tunability of LTRi as disclosed herein makes it an ideal tool for use in the study of mechanisms involved in cellular processes and diseases. Currently, many genetic phenotypes are mimicked in mouse models by generating knock-out animals. While this process can offer many insights based on the phenotype of an animal missing a particular gene, it only allows for the comparison of two extreme cases of gene expression, on versus off. The inventors have demonstrated a method using a genetic switch which exhibits undetectable expression levels of the transgene in the off state and also has the ability to tune the expression of the transgene, and have demonstrated a dose-dependent expression of the transgene. Accordingly, the tunability of LTRi switch as disclosed herein is useful in methods to study phenotypes based on threshold responses of gene expression both in vitro and in vivo. This is demonstrated by the fact that the inventors, using LTRi to control the expression of bax, a pro-apoptotic gene in primary mouse cells, a possible threshold response for Bax-induced apoptosis.

Additionally, the LTRi genetic switch as disclosed herein is useful in methods for an inducible gene knock-out system in vitro and in vivo. For example, using LTRi to regulate the expression of Cre in transgenic mice would give rise to an in vivo, nontoxic inducible knockout system that allows for controlling the timing of the specific gene to be knocked out. Accordingly, the inventors have discovered a method to study genes that would otherwise be lethal if removed too early in the development of the mouse. The inventors have demonstrated the feasibility of this application of inducible gene knock out by demonstrating that LTRi can be used to tightly regulate the expression of Cre recombinase in primary mouse fibroblasts.

Additionally, the LTRi construct is also useful to regulate cytotoxic genes, such as for example DTA which is useful for a variety of mechanistic studies and therapeutic applications. For example, LTRi regulatable expression of a cytotoxic gene in particular neurons or tissues (under the control of a tissue-specific promoter) is useful the study of neurodegenerative diseases to destroy a single type of neuron in mice. The ability to control the expression of DTA with LTRi is also useful for targeting cancer cells (Anderson et al., 2004; Peng et al., 2002). Overall, the inventors have developed and demonstrated a system for tight, tunable, reversible control of mammalian gene expression that is useful in a number of mechanistic studies and therapeutic applications; including but not limited to, (i) exploring a number of biological processes (e.g., stem cell differentiation), (ii) study of the functional role of various genes (e.g. those involved in development or the onset of disease), and (iii) use for therapeutic applications, such as gene therapy and tight control expression of genes in vivo.

SEQ ID NO: 4 corresponds to the LTRi-eGFP nucleic acid construct, and corresponds to the following nucleic acid sequence;

```
TCGCGCGTTTCGGTGATGACGGTGAAAACCTCTGACACATGCAGCTCCCG
GAGACGGTCACAGCTTGTCTGTAAGGGGATGCCGGGAGCAGACAAGCCCG
TCAGGGCGCGTCAGCGGGTGTTGGCGGGTGTCGGGGCTGGCTTAACTATG
CGGCATCAGAGCAGATTGTACTGAGAGTGCACCATATGCGGTGTGAAATA
CCGCACAGATGCGTAAGGAGAAAATACCGCATCAGGCGCCATTCGCCATT
CAGGCTGCGCAACTGTTGGGAAGGGCGATCGGTGCGGGCCTCTTCGCTAT
TACGCCAGCTGGCGAAAGGGGGATGTGCTGCAAGGCGATTAAGTTGGGTA
ACGCCAGGGTTTTCCCAGTCACGACGTTGTAAAACGACGGCCAGTGAATT
ATCCTGCTCCCTGCTTGTGTGTTGGAGGTCGCTGAGTAGTGCGCGAGCAA
AATTTAAGCTACAACAAGGCAAGGCTTGACCGACAATTGCATGAAGAATC
TGCTTAGGGTTAGGCGTTTTGCGCTGCTTCGGGATGTACGGGCCAGATAT
ACGCGTATCTGAGGGGACTAGGGTGTGTTTAGGCGAAAAGCGGGGCTTCG
GTTGTACGCGGTTAGGAGTCCCCTCAGGATATAGTAGTTTCGCTTTTGCA
TAGGGAGGGGGAAATGTAGTCTTATGGAATACTCTTGTAGTCTTGCAACA
TGGTAACGATGAGTTAGCAACATGCCTTACAAGGAGAGAAAAAGCACCGT
GCATGCCGATTGGTGGAAGTAAGGTGGTACGATCGTGGCTTATTAGGAAG
GCAACAGACGGGTCTGACATGGATTGGACGAACCACTGAATTCCGCATTG
CAGAGATATTGTATTTAAGTGCCTAGCTCGATACAATAAACGCCATTTGA
CCATTCCACCACATTGGTGTGCACCAGATCTAAGCTTGGACAAACTACCTA
CAGAGATTTAAAGCTCTAAGGTAAATATAAAATTTAGTAGGTTGTGGAAT
TGTGAGCGCTCACAATTCCACAGTCGACCCTAGGTTGTGGAATTGTGAGC
GCTCACAATTCCACAGTCGACCCTAGGTTGTGGAATTGTGAGCGCTCACA
ATTCCACAGTCGACCCTAGTGTATAATGTGTTAAACTACGGATCCGTCTC
CCATTAGGCCTACAATGGTGAGACAAGTAGCCAACAGGGAAGGGTTGCAA
ATATCATTTGGGCACACCTATGATAATATTGATGAAGCAGACAGTATTCA
GCAAGTAACTGAGAGGTGGGAAGCTCAAAGCCAAAGTCCTAATGTGCAGT
CAGGTGAATTTATTGAAAAATTTGAGGCTCCTGGTGGTGCAAATCAAAGA
ACTGCTCCTCAGGGATCCTAATTGTTTGTGTATTTTAGATTCCAACCAAG
CTTGCGGCCGCTCAGGAGCTAAGGAATTGATCCTCTAGAGTCGACCTGCA
GCACAACCATGGTGAGCAAGGGCGAGGAGCTGTTCACCGGGGTGGTGCCC
ATCCTGGTCGAGCTGGACGGCGACGTAAACGGCCACAAGTTCAGCGTGTC
CGGCGAGGGCGAGGGCGATGCCACCTACGGCAAGCTGACCCTGAAGTTCA
TCTGCACCACCGGCAAGCTGCCCGTGCCCTGGCCCACCCTCGTGACCACC
CTGACCTACGGCGTGCAGTGCTTCAGCCGCTACCCCGAGCACATGAAGCA
GCACGACTTCTTCAAGTCCGCCATGCCCGAAGGCTACGTCCAGGAGGGCA
CCATCTTCTTCAAGGACGACGGCAACTACAAGACCCGCGCCGAGGTGAAG
TTCGAGGGCGACACCCTGGTGAACCGCATCGAGCTGAAGGGCATCGACTT
CAAGGAGGACGGCAAGATCCTGGGGCACAAGCTGGAGTACAACTACAACA
GCCACAACGTCTATATCATGGCCGACAAGCAGAAGAACGGCATCAAGGTG
AACTTCAAGATCCGCCACAACATCGAGGACGGCAGCGTGCAGCTCGCCGA
CCACTACCAGCAGAACACCCCGATCGGCGACGGCCCCGTGCTGCTGCCCG
ACAACCACTACCTGAGCACCCAGTCCGGCCTGAGCAAAGACCCCAACGAG
AAGCGCGATCACATGGTCCTGCTGGAGTTCGTGACCGCCGCGGGATCAC
TCTCGGGATGGAGGAGCTGTACAAGTAAAGCGGCCGCGACTCTAGATCAT
AATCAGCCATACCACATTTGTAGAGGTTTTACTTGCTTTAAAAAACCTCC
CACACCTCCCCCTGAACCTGAAACATAAAATGAATGCACTACACAAATCA
GCGATTTTAATGGTTACAAATAAAGCAATAGCATCACAAATTTCACAAAT
AAAGCATTTTTTTCACTGCAAGCTTGGCGTAATCATGGTCATAGCTGTTT
CGTGTGTGAAATTGTTATCCGCTCACAATTCCAGACAACATACGAGCCGG
AAGCATAAAGTGTAAAGCCTGGGGTGCCTAATGAGTGAGCTAACTCACAT
TAATTGCGTTGCGGTCACTGCCCGCTTTCCAGTCGGGAAACCTGTCGTGC
CAGCTGCATTAATGAATCGGCCAACGCGCGGGGAGAGGCGGTTTGCGTAT
TGGGCGCTGTTCCGCTGCAACTGTTGGGAAGGGCGATCGGTGCGGGCCTC
TTCGCTATTACGCGAGCTGGCGAAAGGGGGATGTGCTGCAAGGCGATTAA
GTTGGGTAACGCCAGGGTTTTCCCAGTCACGACGTTGTAAAACGACGGCC
AGTGAATTGTAATACGACTCACTATAGGGCGAATTGGGCCTTTTTCTACA
CAAATCAGCGATTTTCTCTTGAAAAATCGCTGATTTGTGTAGCGGTGTTT
CGTCCTTTCCACAAGATATATAACTGTATCAATGATAGAGTACTTTCAAG
TTAGGGTAAGCATATGATAGTCCATTTTAAAACATAATTTTAAAACTGCA
AACTACCCAAGAAATTATTACTTTCTACGTCACGTATTTTGTACTAATAT
CTTTGTGTTTACAGTCAAATTAATTCTAATTATCTCTCTAACAGCCTTGT
ATCGTATATGCAAATATGAAGGAATCATGGGAAATAGGCCCTCTTCCTGC
CCGACCTTGGCGCGCGCTCGGCGCGCGGTCACGCTCCGTCACGTGGTGCG
TTTTGCCTAATCACTAGTGAATTCTAGTTATTAATAGTAATCAATTACGG
GGTCATTAGTTCATAGCCCATATATGGAGTTCCGCGTTACATAACTTACG
GTAAATGGCCCGCCTGGCTGACCGCCCAACGACCCCCGCCCATTGACGTC
AATAATGACGTATGTTCCCATAGTAACGCCAATAGGGACTTTCCATTGAC
GTCAATGGGTGGAGTATTTACGGTAAACTGGCCACTTGGCAGTACATCAA
GTGTATCATATGCCAAGTACGCCGCCTATTGACGTCAATGACGGTAAATG
GCCCGCCTGGCATTATGCCCAGTACATGACCTTATGGGACTTTCCTACTT
GGCAGTACATCTACGTATTAGTCATCGCTATTACCATGGTGATGCGGTTT
TGGCAGTACATCAATGGGCGTGGATAGCGGTTTGACTCACGGGGATTTCC
AAGTGTCCACCCCATTGACGTCAATGGGAGTTTGTTTTGGCACCAAAATC
AACGGGACTTTCCAAAATGTCGTAACAACTCCGCCCCATTGACGCAAATG
GGCGGTAGGCGTGTACGGTGGGAGGTCTATATAAGCAGAGCTGGTTTAGT
GAACCGTCAGATCGGATCCTCTAGAGTCGACCATTGCCGCCACCATGAAA
GCAGTAACGTTATACGATGTCGCAGAGTATGCCGGTGTCTCTTATCAGAC
```

```
CGTTTCCCGCGTGGTGAACCAGGCCAGCCACGTTTCTGCGAAAACGCGGG
AAAAAGTGGAAGCGGCGATGGCGGAGCTGAATTACATTCCCAACCGCGTG
GCACAACAACTGGCGGGCAAACAGTCGTTGCTGATTGGCGTTGCCACCTC
CAGTCTGGCCCTGCACGCGCCGTCGCAAATTGTCGCGGCGATTAAATCTC
GCGCCGATCAACTGGGTGCCAGCGTGGTGGTGTCGATGGTAGAACGAAGC
GGCGTCGAAGGCTGTAAAGCGGCGGTGCACAATCTTCTCGCGCAACGCGT
CAGTGGGCTGATCATTAACTATCCGCTGGATGACCAGGATGCCATTGCTG
TGGAAGCTGCCTGGACTAATGTTCCGCGTTATTTCTTGATGTCTCTGAC
CAGACACCCATCAACAGTATTATTTTCTCCCATGAAGACGGTACGCGACT
GGGCGTGGAGGATCTGGTCGCATTGGGTCACCAGCAAATCGCGCTGTTAG
CGGGCCCATTAAGTTCTGTCTCGGCGCGTCTGCGTCTGGCTGGCTGGCAT
AAATATCTCACTCGCAATCAAATTCAGCCGATAGCGGAACGGGAAGGCGA
CTGGAGTGCCATGTCCGGTTTTCAACAAACCATGCAAATGCTGAATGAGG
GCATCGTTCCCACTGCGATGCTGGTTGCCAACGATCAGATGGCGCTGGGC
GCAATGCGCGCCATTACCGAGTCCGGGCTGCGCGTTGGTGCGGATATCTC
GGTAGTGGGATACGACGATACCGAAGACAGCTCATGTTATATCCCGCCGT
TAACCACCATCAAACAGGATTTTCGCCTGCTGGGGCAAACCAGCGTGGAC
CGCTTGCTGCAACTCTCTCAGGGCGAGGCGGTGAAGGGCAATCAGCTGTT
GCCCGTCTCACTGGTGAAAAGAAAAACCACCCTGGCGCCCAATACGCAAA
CCGCCTCTCCCCGCGCGTTGGGCGATTCATTAATGCAGCTGGCACGACAG
GTTTCCCGACTGGAAAGCGGGCAGAGCAGCCTGAGGCCTCCTAAGAAGAA
GAGGAAGGTTTGAGGGCAACGCAATTAATGTAAGTTAGCTCACTCATTAG
GCACCCCAGGCTTTACACTTTATGCTTCCGAGCTGCAGCCCCTTGGATCT
TTGTGAAGGAACCTTACTTCTGTGGTGTGACATAATTGGACAAACTACCT
ACAGAGATTTAAAGCTCTAAGGTAAATATAAAATTTTTAAGTGTATAATG
TGTTAAACTACTGATTCTAATTGTTTGTGTATTTTAGATCACAGTCCCAA
GGCTCATTTCAGGCCCCTCAGTCCTCACAGTCTGTTCATGATCATAATCA
GCCATACCACATTTGTAGAGGTTTTACTTGCTTTAAAAAACCTCCCACAC
CTCCCCCTGAACCTGAAACATAAAATGAATGCAATTGTTGTTGTTAACTT
GTTTATTGCAGCTTATAATGGTTACAAATAAAGCAATAGCATCACAAATT
TCACAAATAAAGCATTTTTTTCACTGCATTCTAGTTGTGGTTTGTCCAAA
CTCATCAATGTATCTTATCATGTCTGGGCCCAAGCTTGGCGTAATCATGG
TCATAGCTGTTTCCTGTGTGAAATTGTTATCCCCTCAGAATTCCACACAA
CATACGAGCCGGAAGCATAAAGTGTAAAGCCTGGGGTGCCTAATGAGTGA
GCTAACTCACATTAATTGCGTTGCGCTCACTGCCCGCTTTCCAGTCGGGA
AACCTGTCGTGCCAGCTGCATTAATGAATCGGCCAACGCGCGGGGAGAGG
CGGTTTGCGTATTGGGCGCTCTTCCGCTTCCTCGCTCACTGACTCGCTGC
GCTCGGTCGTTCGGCTGCGGCGAGCGGTATCAGCTCACTCAAAGGCGGTA
ATACGGTTATCCACAGAATCAGGGGATAACGCAGGAAAGAACATGACATG
TGGCCCTCTAGACTCGACACGTTTTGGCCGAAGTTCCTATTCTCTAGAAA
GTATAGGAACTTCGCGGCCAATTCTACCGGGTAGGGGAGGCGCTTTTCCC
AAGGCAGTCTGGAGCATGCGCTTTAGCAGCCCCGCTGGGCACTTGGCGCT
ACACAAGTGGCCTCTGGCCTCGCACACATTCCACATCCACCGGTAGGCGC
CAACCGGCTCCGTTCTTTGGTGGCCCCTTCGCGCCACCTTCTACTCCTCC
CCTAGTCAGGAAGTTCCCCCCCGCCCCGCAGCTCGCGTCGTGCAGGACGT
GACAAATGGAAGTAGCACGTCTCACTAGTCTCGTGCAGATGGACAGCACC
GCTGAGCAATGGAAGCGGGTAGGCGTTTGGGGCAGCGGCCAATAGCAGCT
TTGCTCCTTCGCTTTCTGGGCTCAGAGGCTGGGAAGGGGTGGGTCCGGGG
GCGGGCTCAGGGGCGGGCTGAGGGGCGGGGCGGGCGCCCGAAGGTCCTCC
GGAGGCCCGGCATTCTGCACGCTTCAAAAGCGCACGTCTGCCGCGCTGTT
CTCCTCTTCCTCATCTCCGGGCCTTTCGACCTGCAGCCAATATGGGATCG
GCCATTGAACAAGATGGATTGCACGCAGGTTCTCCGGCCGCTTGGGTGGA
GAGGCTATTCGGCTATGACTGGGCACAACAGACAATCGGCTGCTCTGATG
CCGCCGTGTTCCGGCTGTGAGCGCAGGGGCGCCCGGTTCTTTTTGTCAAG
ACCGACCTGTCCGGTGCCCTGAATGAACTGCAGGACGAGGCAGCGCGGCT
ATCGTGGCTGGCCACGACGGGCGTTCCTTGCGCAGCTGTGCTCGACGTTG
TCACTGAAGCGGGAAGGGACTGGCTGCTATTGGGCGAAGTGCCGGGGCAG
GATCTCCTGTGATCTCACCTTGCTCCTGCCGAGAAAGTATCCATCATGGC
TGATGCAATGCGGCGGCTGCATACGCTTGATCCGGCTACCTGCCCATTCG
ACCACCAAGCGAAACATCGCATCGAGCGAGCACGTACTCGGATGGAAGGC
GGTCTTGTCGATCAGGATGATCTGGACGAAGAGCATCAGGGGCTCGCGCC
AGCCGAACTGTTCGCCAGGCTCAAGGCGCGCATGCCCGACGGGGAGGATC
TCGTCGTGACCCATGGCGATGCCTGCTTGCCGAATATCATGGTGGAAAAT
GGCCGCTTTTCTGGATTCATCGACTGTGGCCGGCTGGGTGTGGCGGACCG
GTATCAGGACATAGCGTTGGCTACCCGTGATATTGCTGAAGAGCTTGGCG
GCGAATGGGCTGACCGCTTCCTCGTGCTTTACGGTATCGCCGCTCCCGAT
TCGCAGCGCATCGCCTTCTATCGCCTTCTTGACGAGTTCTTCTGAGGGGA
TCCGCTGTAAGTCTGCAGAAATTGATGATCTATTAAACAATAAAGATGTC
CACTAAAATGGAAGTTTTTCCTGTCATACTTTGTTAAGAAGGGTGAGAAC
AGAGTACCTACATTTTGAATGGAAGGATTGGAGCTACGGGGGTGGGGGTG
GGGTGGGATTAGATAAATGCCTGCTCTTTACTGAAGGCTCTTTACTATTG
CTTTATGATAATGTTTCATAGTTGGATATCATAATTTAAACAAGGAAAAC
CAAATTAAGGGCCAGCTCATTCCTGCCACTCATGATCTATAGATCTATAG
ATCTCTCGTGGGATCATTGTTTTTCTCTTGATTCCCACTTTGTGGTTCTA
AGTACTGTGKTTYCCAAATGTGTCAGTTTCATAGCCTGAAGAACGAGATC
AGCAGCGTGTGTTCCAACATACACTTCATTCTNCAGTATTGTTTTGCCAA
GTTCTAATTCCATCAGAAGCTTATCGATACCCGTCGAGGGAAGTTGCTAT
TCTCTAGAAAGTATAGGAACTTCGTCGAGCGGCCGCCAGTGTGATGGATT
CGACCAGACATGATAAGATACATTGATGAGTTTGGACAAACCACAACTAG
AATGCAGTGAAAAAAATGCTTTATTTGTGAAATTTGTGATGCTATTGCTT
TATTTGTAACCATTATAAGCTGCAATAAACAAGTTCTGCTTTAATAAGAT
```

```
CTGAATTCCCGGGATCCGCTGTACGCGGACCCACTTTCACATTTAAGTTG
TTTTTCTAATCCGCATATGATCAATTCAAGGCCGAATAAGAAGGCTGGCT
CTGCACCTTGGTGATCAAATAATTCGATAGCTTGTCGTAATAATGGCGGC
ATACTATCAGTAGTAGGTGTTTCCCTTTCTTCTTTAGCGACTTGATGCTC
TTGATCTTCCAATACGCAACCTAAAGTAAAATGCCCCACAGCGCTGAGTG
CATATAATGCATTCTCTAGTGAAAAACCTTGTTGGCATAAAAAGGCTAAT
TGATTTTCGAGAGTTTCATACTGTTTTTCTGTAGGCCGTGTACCTAAATG
TACTTTTGCTCCATCGGGATGACTTAGTAAAGCACATCTAAAACTTTTAG
CGTTATTACGTAAAAAATGTTGCCAGCTTTCGCCTTCTAAAGGGCAAAAG
TGAGTATGGTGCCTATCTAACATCTCAATGGGTAAGGGGTCGAGCAAAGC
CCGCTTATTTTTTACATGCGAATACAATGTAGGCTGCTCTACACCTAGCT
TCTGGGCGAGTTTACGGGTTGTTAAACCTTCGATTCCGACCTCATTAAGC
AGCTCTAATGCGCTGTTAATCACTTTACTTTTATCTAATCTAGACATATC
AATTCGCCCTATAGTGAGTCGTATTACAATTCTTTGCCAAAATGATGAGA
CAGCACAATAACCAGCACGTTGCCCAGGAGCTGTAGGAAAAAGAAGAAGG
CATGAACATGGTTAGCAGAGGGGCCCGTTCTTTACGATGCCATTGGGATA
TATCAACGGTGGTATATCCAGTGATTTTTTCTCCATTTTAGCTTCCTTA
GCTCCTGAGCGGCCGCAAGCTTGGTTGGAATCTAAAATACACAAACAATT
AGGATCCCTGAGGAGCAGTTCTTTGATTTGCACCACCAGGAGCCTCAAAT
TTTTCAATAAATTCACCTGACTGCACATTAGGAGTTTGGCTTTGAGCTTC
CCACCTCTCAGTTACTTGCTGAATACTGTCTGCTTCATCAATATTATCAT
AGGTGTGCCCAAATGATATTTGCAACCCTTCCCTGTTGGCTACTTGTGTC
ACCATTGTAGGCCTAATGGGAGACGGATCCGTAGTTTAACACATTATACA
CTAGGGTCGACTGTGGAATTGTGAGCGCTCACAATTCCACAACCTAGGGT
CGACTGTGGAATTGTGAGCGCTCACAATTCCACAACCTAGGGTCGACTGT
GGAATTGTGAGCGCTCACAATTCCACAACCTAGTAAATTTTATATTTACC
TTAGAGCTTTAAATCTCTGTAGGTAGTTTGTCCAAGCTTAGATCGTGCAG
GTCGACTCTAGAGGATCCGATCTGACGGTTCACTAAACCAGCTCTGCTTA
TATAGACCTCCCACCGTACACGCCTACCGCCCATTTGCGTCAATGGGGCG
GAGTTGTTACGACATTTTGGAAAGTCCCGTTGATTTTGGTGCCAAAACAA
ACTCCCATTGACGTCAATGGGGTGGAGACTTGGAAATCGCCGTGAGTCAA
ACCGCTATCCACGCCCATTGATGTACTGCCAAAACCGCATCACCATGGTA
ATAGCGATGACTAATACGTAGATGTACTGCCAAGTAGGAAAGTCCCATAA
GGTCATGTACTGGGCATAATGCCAGGCGGGCCATTTACCGTCATTGACGT
CAATAGGGGCGTACTTGGCATATGATACACTTGATGTACTGCCAAGTGG
GCAGTTTACCGTAAATACTCCACCCATTGACGTCAATGGAAAGTCCCTAT
TGGCGTTACTATGGGAACATACGTCATTATTGACGTCAATGGGCGGGGT
CGTTGGGCGGTCAGCCAGGCGGGCCATTTACCGTAAGTTATGTAACGGG
AACTCCATATATGGGCTATGAACTAATGACCCCGTAATTGATTACTATTA
ATAACTAGAATTCACTGGCCGTCGTTTTACAACGTCGTGACTGGGAAAAC
CCTGGCGTTACCCAACTTAATCGCCTTGCAGCACATCCCCCTTTCGCCAG
CTGGCGTAATAGCGAAGAGGCCCGCACCGATTAAGCCGGCGATGTGAGCA
AAAGGCCAGCAAAAGGCCAGGAACCGTAAAAAGGCCGCGTTGCTGGCGTT
TTTCCATAGGCTCCGCCCCCCTGACGAGCATCACAAAAATCGACGCTCAA
GTCAGAGGTGGCGAAACCCGACAGGACTATAAAGATACCAGGCGTTTCCC
CCTGGAAGCTCCCTCGTGCGCTCTCCTGTTCCGACCCTGCCGCTTACCGG
ATACCTGTCCGCCTTTCTCCGTTCGGGAAGCGTGGCGCTTTCTCATAGCT
CACGCTGTAGGTATCTCAGTTCGGTGTAGGTCGTTCGCTCCAAGCTGGGC
TGTGTGCACGAACCCCCCGTTCAGCCCGACCGCTGCGCCTTATCCGGTAA
CTATCGTCTTGAGTCCAACCCGGTAAGACACGACTTATCGCCACTGGCAG
CAGCCAGTGGTAACAGGATTAGCAGAGCGAGGTATGTAGGCGGTGCTACA
GAGTTCTTGAAGTGGTGGCCTAACTACGGCTACACTAGAAGAACAGTATT
TGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTT
TGCAAGCAGCAGATTACGCGCAGAAAAAAAGGATCTCAAGAAGATCCTTT
GATCTTTTCTACGGGGTCTGACGCTCAGTGGAACGAAAACTCACGTTAAG
GGATTTTGGTCATGAGATTATCAAAAAGGATCTTCACCTAGATCCTTTTA
AATTAAAAATGAAGTTTTAAATCAATCTAAAGTATATATGAGTAAACTTG
GTCTGACAGTTACCAATGCTTAATCAGTGAGGCACCTATCTCAGCGATCT
GTCTATTTCGTTCATCCATAGTTGCCTGACTCCCCGTCGTGTAGATAACT
ACGATACGGGAGGGCTTACCATCTGGCCCCAGTGCTGCAATGATACCGCG
AGACCCACGCTCACCGGCTCCAGATTTATCAGCAATAAACCAGCCAGCCG
GAAGGGCCGAGCGCAGAAGTGGTCCTGCAACTTTATCCGCCTCCATCCAG
TCTATTAATTGTTGCCGGGAAGCTAGAGTAAGTAGTTCGCCAGTTAATAG
TTTGCGGAACGTTGTTGCCATTGCTACAGGCATCGTGGTGTCACGCTCGT
CGTTTGGTATGGCTTCATTCAGCTGCGGTTCCCAACGATCAAGGCGAGTT
ACATGATCCCCCATGTTGTGCAAAAAAGCGGTTAGCTCCTTGGGTCCTCC
GATCGTTGTCAGAAGTAAGTTGGCCGCAGTGTTATCACTCATGGTTATGG
CAGCACTGCATAATTCTCTTACTGTCATGCCATCCGTAAGATGCTTTTCT
GTGACTGGTGAGTACTCAACCAAGTCATTCTGAGAATAGTGTATGCGGCG
ACCGAGTTGCTCTTGCCCGGCGTCAATACGGGATAATACCGCGCCACATA
GCAGAACTTTAAAAGTGCTCATCATTGGAAAACGTTCTTCGGGGCGAAAA
CTCTCAAGGATCTTACCGCTGTTGAGATCCAGTTCGATGTAACCCACTCG
TGCACCCAACTGATCTTCAGCATGTTTTACTTTCACCAGCGTTTCTGGGT
GAGCAAAAACAGGAAGGCAAAATGCCGCAAAAAAGGGAATAAGGGCGACA
CGGAAATGTTGAATACTCATACTCTTCCTTTTTCAATATTATTGAAGCAT
TTATCAGGGTTATTGTCTCATGAGCGGATACATATTTGAATGTATTTAGA
AAAATAAACAAATAGGGGTTCCGCGCACATTTGCCCGAAAAGTGCCACGT
GACGTCTAAGAAACGATTATTATCATGACATTAACCTATAAAAATAGGCG
TATCACGAGGCCCTTTCGTC
```

REFERENCES

The references cited herein and throughout the application are incorporated herein by reference.

Anderson, D. G., Peng, W., Akinc, A., Hossain, N., Kohn, A., Padera, R., Langer, R., and Sawicki, J. A. (2004). A polymer library approach to suicide gene therapy for cancer. Proc. Natl. Acad. Sci. USA 101, 16028-16033.

Aneja, R., Zhou, J., Zhou, B., Chandra, R., and Joshi, H. C. (2006). Treatment of hormone-refractory breast cancer: apoptosis and regression of human tumors implanted in mice, Mol. Cancer Ther. 5, 2366-2377.

Atkinson, M R., Savageau, M A., Myers, J. T., and Ninfa, A. J. (2003). Development of genetic circuitry exhibiting toggle switch or oscillatory behavior in Escherichia coli. Cell 1 13, 597-607.

Banaszynski, L. A., Chen, L. C., Maynard-Smith, L. A., Ooi, A G., and Wandless, T. J. (2006). A rapid, reversible, and tunable method to regulate protein function in living cells using synthetic small molecules. Cell 126, 995-1004.

Basu, S., Mehreja, R., Thiberge, S., Chen, M T., and Weiss, R. (2004). Spatiotemporal control of gene expression with pulse-generating networks. Proc. Natl. Acad. Sci. USA 101, 6355-6360.

Becskei, A., and Serrano, L. (2000). Engineering stability in gene networks by autoregulation. Nature 405, 590-593.

Blake, W. J., Kaern, M., Cantor, C R., and Collins, J. J. (2003). Noise in eukaryotic gene expression. Nature 422, 633-637.

Brown, M., Figge, J., Hansen, U., Wright, C., Jeang, K. T., Khoury, G., Livingston, D. M., and Roberts, T M. (1987). lac repressor can regulate expression from a hybrid SV4O early promoter containing a lac operator in animal cells. Cell 49, 603-612.

Danielian, P. S., Muccino, D., Rowitch, D. H., Michael, 5K., and McMahon, A. P. (1998). Modification of gene activity in mouse embryos in utero by a tamoxifen-inducible form of Cre recombinase. Curr. Biol. 8, 1323-1326.

Elowitz, M B., and Leibler, S. (2000). A synthetic oscillatory network of transcriptional regulators. Nature 403, 335-338.

Elowitz, M B., Levine, A. J., Siggia, E D., and Swain, P. S. (2002). Stochastic gene expression in a single cell. Science 297, 1183-1186.

Fire, A., Xu, S., Montgomery, M. K., Kostas, S. A., Driver, S E., and Mello, C C. (1998). Potent and specific genetic interference by double-stranded RNA in Caenorhabditis elegans. Nature 391, 806-811.

Fung, E., Wong, W. W., Suen, J. K., Bulter, T., Lee, 5G., and Liao, J. C. (2005). A synthetic gene-metabolic oscillator. Nature 435, 118-122.

Gardner, T. S., Cantor, C R., and Collins, J. J. (2000). Construction of a genetic toggle switch in Escherichia coli. Nature 403, 339-342.

Gossen, M., and Bujard, H. (1992). Tight control of gene expression in mammalian cells by tetracycline-responsive promoters. Proc. Natl. Acad. Sci. USA 89, 5547-5551.

Greenfield, L., Bjorn, M. J., Horn, G., Fong, D., Buck, G A., Collier, R. J., and Kaplan, D. A. (1983). Nucleotide sequence of the structural gene for diphtheria toxin carried by corynebacteriophage beta. Proc. Natl. Acad. Sci. USA 80, 6853-6857.

Guet, C C., Elowitz, M B., Hsing, W., and Leibler, S. (2002). Combinatonal synthesis of genetic networks. Science 296, 1466-1470.

Guido, N. J., Wang, X., Adalsteinsson, D., McMillen, D., Hasty, J., Can-tor, C R, Elston, T. C., and Collins, J. J. (2006). A bottom-up approach to gene regulation. Nature 439, 856-860.

Guo, S., and Kemphues, K. J. (1995). par-i, a gene required for establishing polarity in C. elegans embryos, encodes a putative Ser/Thr kinase that is asymmetrically distributed. Cell 81, 611-620.

Hooshangi, S., Thiberge, S., and Weiss, R. (2005). Ultrasensitivity and noise propagation in a synthetic transcriptional cascade. Proc. Natl. Acad. Sci. USA 102, 3581-3586.

Hu, M C., and Davidson, N. (1987). The inducible lac operator-repressor system is functional in mammalian cells. Cell 48, 555-566.

Imai, T., Jiang, M., Chambon, P., and Metzger, D. (2001). Impaired adipogenesis and lipolysis in the mouse upon selective ablation of the retinoid X receptor alpha mediated by a tamoxifen-inducible chimeric Cre recombinase (Cre-ERT2) in adipocytes. Proc. Natl. Acad. Sci. USA 98, 224-228.

Isaacs, F. J., Hasty, J., Cantor, C R., and Collins, J. J. (2003). Prediction and measurement of an autoregulatory genetic module. Proc. Natl. Acad. Sci. USA 100, 771 4-771 9.

Isaacs, F. J., Dwyer, D. J., Ding, C., Pervouchine, D. D., Cantor, C R., and Collins, J. J. (2004). Engineered riboregulators enable post-transcriptional control of gene expression. Nat. Biotechnol. 22, 841-847.

Isalan, M., Lemerle, C., and Serrano, L. (2005). Engineering gene networks to emulate Drosophila embryonic pattern formation. PLoS Biol. 3, e64.

Katiyar, 5K., Roy, A M., and Baliga, M S. (2005). Silymarin induces apoptosis primarily through a p53-dependent pathway involving Bcl-2/Bax, cytochrome c release, and caspase activation. Mol. Cancer Ther. 4, 207-21 6.

Kobayashi, H., Kaern, M., Araki, M., Chung, K., Gardner, T. S., Cantor, C R., and Collins, J. J. (2004). Programmable cells: interfacing natural and engineered gene networks. Proc. Natl. Acad. Sci. USA 101, 8414-8419.

Kramer, B. P., and Fussenegger, M. (2005). Hysteresis in a synthetic mammalian gene network. Proc. Natl. Acad. Sci. USA 102, 951 7-9522.

Kramer, B. P., Viretta, A U., Daoud-El-Baba, M., Aubel, D., Weber, W., and Fussenegger, M. (2004). An engineered epigenetic transgene switch in mammalian cells. Nat. Biotechnol. 22, 867-870.

Kramer, B. P., Fischer, M., and Fussenegger, M. (2005). Semi-synthetic mammalian gene regulatory networks. Metab. Eng. 7, 24i-250. Malphettes, L., and Fussenegger, M. (2006). Improved transgene expression fine-tuning in mammalian cells using a novel transcription-translation network. J. Biotechnol. 124, 732-746.

Ornitz, D. M., Moreadith, R. W., and Leder, P. (1991). Binary system for regulating transgene expression in mice: targeting int-2 gene expression with yeast GAL4/UAS control elements. Proc. Natl. Acad, Sci. USA 88, 698-702.

Ozbudak, E M., Thattai, M., Kurtser, I., Grossman, A D., and van Oudenaarden, A. (2002). Regulation of noise in the expression of a sin-gle gene. Nat. Genet. 31, 69-73.

Paddison, P. J., Silva, J. M., Conklin, D. S., Schlabach, M., Li, M., Aruleba, S., Balija, V., O'Shaughnessy, A., Gnoj, L., Scobie, K., et al. (2004). A resource for large-scale RNA-interference-based screens in mammals. Nature 428, 427-43i.

Pastorino, J. G., Chen, S T., Tafani, M., Snyder, J. W., and Farber, J. L. (1998). The overexpression of Bax produces cell death upon induction of the mitochondrial permeability transition. J. Biol. Chem. 273, 7770-7775.

Pedraza, J. M., and van Oudenaarden, A. (2005). Noise propagation in gene networks. Science 307, 1965-1969.

Peng, W., Verbitsky, A., Bao, V., and Sawicki, J. (2002). Regulated expression of diphtheria toxin in prostate cancer cells. Mol. Ther. 6, 537-545.

Rosenfeld, N., Elowitz, M B., and Alon, U. (2002). Negative autoregulation speeds the response times of transcription networks. J. Mol. Biol. 323, 785-793.

Rosenfeld, N., Young, J. W., Alon, U., Swain, P. S., and Elowitz, M B. (2005). Gene regulation at the single-cell level. Science 307, 1962-1965.

Scrable, H. (2002). Say when: reversible control of gene expression in the mouse by lac. Semin. Cell Dev. Biol. 13, 109-119.

Shinoura, N., Yoshida, Y., Asai, A., Kirino, T., and Hamada, H. (1999). Relative level of expression of Bax and BcI-XL determines the cellular fate of apoptosis/necrosis induced by the overexpression of Bax. Oncogene 18, 5703-5713.

Soriano, P. (1999). Generalized IacZ expression with the ROSA26 Cre reporter strain. Nat. Genet. 21, 70-71.

Sternberg, N., and Hamilton, D. (1981). Bacteriophage P1 site-specific recombination. I. Recombination between IoxP sites. J. Mol, Biol. 150, 467-486

Szulc, J., Wiznerowicz, M., Sauvain, M O., Trono, D., and Aebischer, P. (2006). A versatile tool for conditional gene expression and knock-down. Nat. Methods 3, 109-116.

van Engeland, M., Nieland, L. J., Ramaekers, F. C., Schutte, B., and Reutelingsperger, C. P. (1998). Annexin V-affinity assay: a review on an apoptosis detection system based on phosphatidylserine exposure. Cytometry 31, 1-9.

Wolter, K G., Hsu, Y. T., Smith, C L., Nechushtan, A., Xi, X. G., and Youle, R. J. (1997). Movement of Bax from the cytosol to mitochondria during apoptosis. J. Cell Biol. 139, 1281-1292.

Yamaizumi, M., Mekada, E., Uchida, T., and Okada, Y. (1978). One molecule of diphtheria toxin fragment A introduced into a cell can kill the cell. Cell 15, 245-250.

You, L., Cox, R. S., 3rd, Weiss, R., and Arnold, F. H. (2004). Programmed population control by cell-cell communication and regulated killing. Nature 428, 868-871.

The invention claimed is:

1. A method of dose-dependent gene expression of a heterologous target gene in a biological process in a cell, the method comprising
    (a) providing a cell with a heterologous target gene for expression, wherein the heterologous target gene is inserted into the cell having a system comprising:
        a nucleic acid sequence encoding an RNA interference molecule (RNAi) agent and a nucleic acid RNAi target sequence, wherein the RNAi target sequence is not endogenous to the cell and is located within the 3'UTR or an intron sequence of the nucleic acid sequence encoding the heterologous target gene,
        wherein the RNAi molecule agent is substantially complementary to the RNAi target sequence such that gene silencing of the RNAi target sequence and the heterologous target gene occurs in the presence of, and upon complementation with the RNAi molecule agent;
        wherein a nucleotide sequence encoding the heterologous target gene is operatively linked to a first repressor promoter sequence,
        wherein the nucleotide sequence encoding the RNAi agent is operatively linked to a second repressor promoter sequence,
        wherein the second repressor promoter sequence is controlled by a second repressor molecule,
        wherein the nucleic acid sequence encoding the second repressor molecule is operatively linked to a second promoter and a first repressor promoter sequence,
        wherein the first repressor promoter sequence is controlled by a first repressor molecule,
        wherein the nucleic acid sequence encoding the first repressor molecule is operatively linked to a first promoter,
        wherein the first repressor molecule is inhibited by a small molecule inducer; and wherein the presence of the small molecule inducer relieves repression of the first repressor promoter sequence thereby inducing the expression of the second repressor molecule which represses the expression of the RNAi agent, thereby permitting dose-dependent gene expression of the heterologous target gene; and
    (b) contacting the cell with an effective amount of the small molecule inducer to induce the gene expression of the heterologous target gene in a dose-dependent manner.

2. The method of claim 1, wherein the first repressor promoter sequence comprises a Lac operator sequence (LacO) and the first repressor molecule is Lac Repressor (LacI).

3. The method of claim 1, wherein the second repressor promoter sequence comprises a Tet operator sequence (TetO) and the second repressor molecule is Tet Repressor (TerR).

4. The method of claim 1, wherein the small molecule inducer is IPTG.

5. The method of claim 1, wherein the first promoter and second promoters are selected from the group consisting of a constitutive promoter or a tissue-specific promoter.

6. The method of claim 1, wherein the first repressor molecule is LaI, or a variant or fragment thereof.

7. The method of claim 1, wherein the first repressor promoter sequence comprises a LacO site, or a variant or fragment thereof.

8. The method of claim 1, wherein the small molecule inducer is IPTG.

9. The method of claim 1, wherein the second repressor molecule is TetR, or a variant or fragment thereof.

10. The method of claim 1, wherein the target nucleotide sequence of the first repressor comprises a tet operator site (TetO) or a variant or fragment thereof.

11. The method of claim 1, wherein the RNA interference (RNAi) molecule is selected from the group consisting of; antisense oligonucleotide, oligonucleotide, siRNA, shRNA or double stranded RNA (dsRNA).

12. The method of claim 1, wherein the RNAi molecule corresponds to SEQ ID NO:1 or SEQ ID NO:2 or a variant or homologue thereof.

13. The method of claim 1, wherein the heterologous target gene is a marker gene or a fragment thereof.

14. The method of claim 1, further comprising a marker gene or a fragment thereof, operatively linked to the first repressor promoter sequence.

15. The method of claim 1, wherein the heterologous gene is selected from the group comprising: a cre recombinase (Cre) gene, a toxin molecule gene, an immunotoxin molecule gene, a gene encoding a molecule that sensitizes the cell to one or more secondary agents, an anti-apoptotic gene or a fragment thereof.

16. The method of claim 1, wherein the nucleotide construct optionally further comprises a nucleotide sequence encoding at least one marker gene which is operatively linked to the expression of the heterologous target gene or the first repressor promoter sequence, wherein gene expression of the marker gene identifies cells also expressing the target gene.

17. The method of claim 1, wherein the first or second promoter is selected from the group comprising of; 3' untranslated regions (3'UTR), repressor sequences; constitutive promoters, inducible promoter; tissue specific promoter or variants thereof.

18. The method of claim 1, wherein the first or second promoter is a selected from the group consisting of: albumin, lymphoid specific promoters, T-cell promoters, neurofilament promoter, pancreas specific promoters, milk whey promoter; hox promoters, α-fetoprotein promoter, human LIMK2 gene promoters, FAB promoter, insulin gene promoter, transphyretin promoter, alpha.1-antitrypsin promoter, plasminogen activator inhibitor type 1 (PAI-1) promoter, apolipoprotein myelin basic protein (MBP) promoter, GFAP promoter, OPSIN promoter, NSE promoter, tetracycline promoter, metallothionine promoter, ecdysone promoter, a mammalian virus promoter, steroid-responsive promoters, rapamycin responsive promoters and fragments thereof.

19. The method of claim 18, wherein the mammalian virus promoter is an adenovirus late promoter or a mouse mammary tumor virus long terminal repeat (MMTV-LTR).

* * * * *